(12) United States Patent
Drake et al.

(10) Patent No.: US 11,331,475 B2
(45) Date of Patent: *May 17, 2022

(54) TETHER ASSEMBLIES FOR MEDICAL DEVICE DELIVERY SYSTEMS

(71) Applicant: Medtronic, Inc., Minneapolis, MN (US)

(72) Inventors: Ronald A. Drake, St. Louis Park, MN (US); Lester O. Stener, Hudson, WI (US); Brian P. Colin, Anoka, MN (US)

(73) Assignee: Medtronic, Inc., Minneapolis, MN (US)

(*) Notice: Subject to any disclaimer, the term of this patent is extended or adjusted under 35 U.S.C. 154(b) by 115 days.

This patent is subject to a terminal disclaimer.

(21) Appl. No.: 16/847,315

(22) Filed: Apr. 13, 2020

(65) Prior Publication Data

US 2020/0353242 A1 Nov. 12, 2020

Related U.S. Application Data

(60) Provisional application No. 62/844,674, filed on May 7, 2019.

(51) Int. Cl.
*A61N 1/05* (2006.01)
*A61N 1/375* (2006.01)

(52) U.S. Cl.
CPC ............ *A61N 1/057* (2013.01); *A61N 1/3756* (2013.01); *A61N 1/37512* (2017.08); *A61N 1/37518* (2017.08)

(58) Field of Classification Search
CPC ................ A61N 1/057; A61N 1/37512; A61N 1/37518; A61N 1/3756
See application file for complete search history.

(56) References Cited

U.S. PATENT DOCUMENTS

| 4,035,909 A | 7/1977 | Dey |
| 4,103,690 A | 8/1978 | Harris |

(Continued)

FOREIGN PATENT DOCUMENTS

| EP | 3192559 | 7/2017 |
| WO | WO 00/59376 A1 | 10/2000 |

(Continued)

OTHER PUBLICATIONS

U.S. Appl. No. 16/847,344, naming inventors Drake et al., filed Apr. 13, 2020.

(Continued)

*Primary Examiner* — Catherine M Voorhees
*Assistant Examiner* — Roland Dinga
(74) *Attorney, Agent, or Firm* — Shumaker & Sieffert, P.A.

(57) ABSTRACT

In some examples, a tether head assembly of a delivery system includes an inner retainer and an outer retainer that defines an aperture comprising a receptacle configured to receive an attachment member of a medical device, a passageway, and a groove. The inner retainer is movable within the groove between a second position in which the passageway is dimensioned to receive the attachment member and a first position in which the passageway is dimensioned to prevent passage of the attachment member. In some examples, a tether handle assembly defines a channel, a force transmitter within the channel, a slidable member partially received within a first end of the channel and a button partially received within a second end of the channel. Distally-directed force applied to the button may cause the force transmitter to apply proximally-directed force to the slidable member, moving the slidable member and an attached pull wire proximally.

22 Claims, 34 Drawing Sheets

(56) References Cited

U.S. PATENT DOCUMENTS

| | | |
|---|---|---|
| 4,112,952 A | 9/1978 | Thomas et al. |
| 4,376,811 A | 3/1983 | Goebel |
| 4,494,531 A | 1/1985 | Gianturco |
| 4,727,873 A | 3/1988 | Mabin-Uddin |
| 4,731,305 A | 5/1988 | Goebel et al. |
| 5,002,067 A | 3/1991 | Berthelsen et al. |
| 5,024,239 A | 6/1991 | Rosenstein |
| 5,098,393 A | 3/1992 | Amplatz et al. |
| 5,249,574 A | 10/1993 | Bush et al. |
| 5,255,678 A | 10/1993 | Deslauriers et al. |
| 5,255,679 A | 10/1993 | Imran |
| 5,265,608 A | 11/1993 | Lee et al. |
| 5,282,845 A | 2/1994 | Bush et al. |
| 5,306,581 A | 4/1994 | Taylor et al. |
| 5,314,462 A | 5/1994 | Heil, Jr. et al. |
| 5,324,316 A | 6/1994 | Schulman et al. |
| 5,358,514 A | 10/1994 | Schulman et al. |
| 5,383,922 A | 1/1995 | Zipes et al. |
| 5,387,233 A | 2/1995 | Alfemess et al. |
| 5,492,119 A | 2/1996 | Abrams |
| 5,540,734 A | 7/1996 | Zabara |
| 5,545,219 A | 8/1996 | Kuzma |
| 5,562,723 A | 10/1996 | Rugland et al. |
| 5,766,234 A | 6/1998 | Chen et al. |
| 5,776,632 A | 7/1998 | Honegger |
| 5,814,089 A | 9/1998 | Stokes et al. |
| 5,824,041 A | 10/1998 | Lenker et al. |
| 5,840,076 A | 11/1998 | Swanson et al. |
| 5,860,974 A | 1/1999 | Abele |
| 5,895,391 A | 4/1999 | Farnholtz |
| 5,897,584 A | 4/1999 | Herman |
| 5,968,052 A | 10/1999 | Sullivan et al. |
| 5,984,944 A | 11/1999 | Forber |
| 6,024,752 A | 2/2000 | Horn et al. |
| 6,074,401 A | 6/2000 | Gardiner et al. |
| 6,113,593 A | 9/2000 | Tu et al. |
| 6,120,480 A | 9/2000 | Zhang et al. |
| 6,136,005 A | 10/2000 | Goode et al. |
| 6,149,658 A | 11/2000 | Gardiner et al. |
| 6,183,305 B1 | 2/2001 | Doan et al. |
| 6,238,813 B1 | 5/2001 | Maile et al. |
| 6,258,098 B1 | 7/2001 | Taylor et al. |
| 6,266,568 B1 | 7/2001 | Mann et al. |
| 6,270,489 B1 | 8/2001 | Wise et al. |
| 6,308,105 B1 | 10/2001 | Duysens et al. |
| 6,322,586 B1 | 11/2001 | Monroe et al. |
| 6,350,278 B1 | 2/2002 | Lenker et al. |
| 6,352,561 B1 | 3/2002 | Leopold et al. |
| 6,395,017 B1 | 5/2002 | Dwyer et al. |
| 6,434,431 B1 | 8/2002 | Camps et al. |
| 6,468,301 B1 | 10/2002 | Amplatz et al. |
| 6,477,423 B1 | 11/2002 | Jenkins |
| 6,498,951 B1 | 12/2002 | Larson et al. |
| 6,505,075 B1 | 1/2003 | Weiner |
| 6,510,332 B1 | 1/2003 | Greenstein |
| 6,514,265 B2 | 2/2003 | Ho et al. |
| 6,514,280 B1 | 2/2003 | Gilson |
| 6,529,777 B1 | 3/2003 | Holmstrom et al. |
| 6,551,332 B1 | 4/2003 | Nguyen et al. |
| 6,582,400 B1 | 6/2003 | Hawk et al. |
| 6,585,634 B1 | 7/2003 | Henckel et al. |
| 6,589,238 B2 | 7/2003 | Edwards et al. |
| 6,600,955 B1 | 7/2003 | Zierhofer |
| 6,607,541 B1 | 8/2003 | Gardiner et al. |
| 6,607,843 B2 | 8/2003 | Ruth, II et al. |
| 6,613,059 B2 | 9/2003 | Schaller et al. |
| 6,623,518 B2 | 9/2003 | Thompson et al. |
| 6,626,916 B1 | 9/2003 | Yeung et al. |
| 6,641,593 B1 | 11/2003 | Schaller et al. |
| 6,645,143 B2 | 11/2003 | VanTassel et al. |
| 6,679,902 B1 | 1/2004 | Boyle et al. |
| 6,689,056 B1 | 2/2004 | Kilcoyne et al. |
| 6,695,859 B1 | 2/2004 | Golden et al. |
| 6,840,956 B1 | 1/2005 | Wolinsky et al. |
| 6,866,650 B2 | 3/2005 | Stevens et al. |
| 6,876,885 B2 | 4/2005 | Swoyer et al. |
| 6,889,093 B1 | 5/2005 | Flammang |
| 6,895,283 B2 | 5/2005 | Erickson et al. |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,932,837 B2 | 8/2005 | Amplatz et al. |
| 6,960,221 B2 | 11/2005 | Ho et al. |
| 7,047,084 B2 | 5/2006 | Erickson et al. |
| 7,054,692 B1 | 5/2006 | Whitehurst et al. |
| 7,060,038 B2 | 6/2006 | Letort et al. |
| 7,070,881 B2 | 7/2006 | Kishiyama et al. |
| 7,072,703 B2 | 7/2006 | Zhang et al. |
| 7,099,718 B1 | 8/2006 | Thacker et al. |
| 7,128,765 B2 | 10/2006 | Paulot et al. |
| 7,147,604 B1 | 12/2006 | Allen et al. |
| 7,172,620 B2 | 2/2007 | Gilson |
| 7,177,702 B2 | 2/2007 | Wallace et al. |
| 7,181,288 B1 | 2/2007 | Rezai et al. |
| 7,236,821 B2 | 6/2007 | Cates et al. |
| 7,288,096 B2 | 10/2007 | Chin |
| 7,291,186 B2 | 11/2007 | Zhang |
| 7,294,334 B1 | 11/2007 | Michal et al. |
| 7,309,349 B2 | 12/2007 | Jackson et al. |
| 7,364,541 B2 | 4/2008 | Chu et al. |
| 7,410,512 B2 | 8/2008 | Tsukamoto et al. |
| 7,473,266 B2 | 1/2009 | Glaser et al. |
| 7,499,758 B2 | 3/2009 | Cates et al. |
| 7,572,228 B2 | 8/2009 | Wolinsky et al. |
| 7,699,059 B2 | 4/2010 | Fonseca et al. |
| 7,704,245 B2 | 4/2010 | Dittman et al. |
| 7,717,854 B2 | 5/2010 | Mann et al. |
| 7,740,655 B2 | 6/2010 | Birdsall |
| 7,765,014 B2 | 7/2010 | Eversull et al. |
| 7,769,420 B2 | 8/2010 | Silver et al. |
| 7,776,080 B2 | 8/2010 | Bei et al. |
| 7,783,338 B2 | 8/2010 | Ainsworth et al. |
| 7,785,360 B2 | 8/2010 | Freitag |
| 7,797,053 B2 | 9/2010 | Atkinson et al. |
| 7,801,626 B2 | 9/2010 | Moser |
| 7,871,430 B2 | 1/2011 | Pavcnik et al. |
| 7,963,952 B2 | 6/2011 | Wright et al. |
| 8,062,327 B2 | 11/2011 | Chaduszko et al. |
| 8,352,028 B2 | 1/2013 | Wenger |
| 8,532,790 B2 | 9/2013 | Griswold |
| 8,715,332 B2 | 5/2014 | Tan et al. |
| 9,186,501 B2 | 11/2015 | Brijmohansigngh et al. |
| 9,775,982 B2 | 10/2017 | Gmbac et al. |
| 9,844,659 B2 | 12/2017 | Grubac et al. |
| 10,052,127 B2 | 8/2018 | Wood |
| 10,071,243 B2 | 9/2018 | Kuhn et al. |
| 10,080,888 B2 | 9/2018 | Kelly et al. |
| 10,099,050 B2 | 10/2018 | Chen et al. |
| 10,112,045 B2 | 10/2018 | Anderson et al. |
| 10,118,026 B2 | 11/2018 | Grubac et al. |
| 10,173,050 B2 | 1/2019 | Grubac et al. |
| 2001/0002300 A1 | 5/2001 | Tinker et al. |
| 2001/0047181 A1 | 11/2001 | Ho et al. |
| 2002/0010490 A1 | 1/2002 | Schaller et al. |
| 2002/0082610 A1 | 6/2002 | Cioanta et al. |
| 2002/0103521 A1 | 8/2002 | Swoyer et al. |
| 2002/0111659 A1 | 8/2002 | Davis et al. |
| 2002/0120250 A1 | 8/2002 | Altman |
| 2002/0147485 A1 | 10/2002 | Mamo et al. |
| 2002/0156513 A1 | 10/2002 | Borkan |
| 2002/0195872 A1 | 12/2002 | Weiner |
| 2003/0004537 A1 | 1/2003 | Boyle et al. |
| 2003/0036790 A1 | 2/2003 | Corbett, III et al. |
| 2003/0045901 A1 | 3/2003 | Opolski |
| 2003/0069623 A1 | 4/2003 | Stypulkowski |
| 2003/0078603 A1 | 4/2003 | Schaller et al. |
| 2003/0088301 A1 | 5/2003 | King |
| 2003/0093118 A1 | 5/2003 | Ho et al. |
| 2003/0093130 A1 | 5/2003 | Stypulkowski |
| 2003/0120328 A1 | 6/2003 | Jenkins et al. |
| 2003/0199974 A1 | 10/2003 | Lee et al. |
| 2003/0236545 A1 | 12/2003 | Gilson |
| 2004/0059393 A1 | 3/2004 | Policker et al. |

(56) References Cited

U.S. PATENT DOCUMENTS

| | | |
|---|---|---|
| 2004/0093053 A1 | 5/2004 | Gerber et al. |
| 2004/0101746 A1 | 5/2004 | Ota et al. |
| 2004/0102797 A1 | 5/2004 | Golden et al. |
| 2004/0111099 A1 | 6/2004 | Nguyen et al. |
| 2004/0111139 A1 | 6/2004 | McCreery |
| 2004/0116878 A1 | 6/2004 | Byrd et al. |
| 2004/0116992 A1 | 6/2004 | Wardle et al. |
| 2004/0148007 A1 | 7/2004 | Jackson et al. |
| 2004/0176782 A1 | 9/2004 | Hanse et al. |
| 2004/0181206 A1 | 9/2004 | Chiu et al. |
| 2004/0185337 A1 | 9/2004 | Ishizaki |
| 2004/0193229 A1 | 9/2004 | Starkebaum et al. |
| 2004/0215230 A1 | 10/2004 | Frazier et al. |
| 2004/0230279 A1 | 11/2004 | Cates et al. |
| 2004/0243206 A1 | 12/2004 | Tadlock |
| 2004/0249433 A1 | 12/2004 | Freitag |
| 2005/0015129 A1 | 1/2005 | Mische |
| 2005/0021054 A1 | 1/2005 | Ainsworth et al. |
| 2005/0060014 A1 | 3/2005 | Swoyer et al. |
| 2005/0065601 A1 | 3/2005 | Lee et al. |
| 2005/0070924 A1 | 3/2005 | Schaller et al. |
| 2005/0090884 A1 | 4/2005 | Honeck |
| 2005/0096718 A1 | 5/2005 | Gerber et al. |
| 2005/0102006 A1 | 5/2005 | Whitehurst et al. |
| 2005/0107861 A1 | 5/2005 | Harris et al. |
| 2005/0107862 A1 | 5/2005 | Ohlenschlaeger |
| 2005/0149141 A1 | 7/2005 | Starkebaum |
| 2005/0149142 A1 | 7/2005 | Starkebaum |
| 2005/0154321 A1 | 7/2005 | Wolinsky et al. |
| 2005/0171479 A1 | 8/2005 | Hruska et al. |
| 2005/0209653 A1 | 9/2005 | Herbert et al. |
| 2005/0221054 A1 | 10/2005 | Kawano et al. |
| 2005/0222632 A1 | 10/2005 | Obino |
| 2005/0245840 A1 | 11/2005 | Christopherson et al. |
| 2005/0245986 A1 | 11/2005 | Starkebaum |
| 2005/0246004 A1 | 11/2005 | Cameron et al. |
| 2005/0267487 A1 | 12/2005 | Christensen et al. |
| 2005/0287859 A1 | 12/2005 | Komizo et al. |
| 2005/0288596 A1 | 12/2005 | Eigler et al. |
| 2006/0047205 A1 | 3/2006 | Ludomirsky et al. |
| 2006/0057458 A1 | 3/2006 | O'Dea et al. |
| 2006/0069422 A9 | 3/2006 | Bolduc et al. |
| 2006/0079943 A1 | 4/2006 | Narciso, Jr. |
| 2006/0079950 A1 | 4/2006 | Lehnhardt et al. |
| 2006/0085041 A1 | 4/2006 | Hastings et al. |
| 2006/0085042 A1 | 4/2006 | Hastings et al. |
| 2006/0085971 A1 | 4/2006 | Andrevvs et al. |
| 2006/0099238 A1 | 5/2006 | Khosravi et al. |
| 2006/0100686 A1 | 5/2006 | Bolduc et al. |
| 2006/0149324 A1 | 7/2006 | Mann et al. |
| 2006/0149330 A1 | 7/2006 | Mann et al. |
| 2006/0206163 A1 | 9/2006 | Wahlstrand et al. |
| 2006/0206165 A1 | 9/2006 | Jaax et al. |
| 2006/0206166 A1 | 9/2006 | Weiner |
| 2006/0212096 A1 | 9/2006 | Stevenson |
| 2006/0222942 A1 | 10/2006 | Zhao et al. |
| 2006/0241733 A1 | 10/2006 | Zhang et al. |
| 2006/0259128 A1 | 11/2006 | Pavcnik et al. |
| 2006/0271137 A1 | 11/2006 | Stanton-Hicks |
| 2006/0275659 A1 | 12/2006 | Kim et al. |
| 2007/0027514 A1 | 2/2007 | Gerber |
| 2007/0027515 A1 | 2/2007 | Gerber |
| 2007/0043414 A1 | 2/2007 | Fifer et al. |
| 2007/0043424 A1 | 2/2007 | Pryor |
| 2007/0073391 A1 | 3/2007 | Bourang et al. |
| 2007/0088230 A1 | 4/2007 | Terashi et al. |
| 2007/0088396 A1 | 4/2007 | Jacobson |
| 2007/0088418 A1 | 4/2007 | Jacobson |
| 2007/0129637 A1 | 6/2007 | Wolinksy et al. |
| 2007/0135826 A1 | 6/2007 | Zaver et al. |
| 2007/0150020 A1 | 6/2007 | Hokanson et al. |
| 2007/0154801 A1 | 7/2007 | Hyung et al. |
| 2007/0156126 A1 | 7/2007 | Flaherty |
| 2007/0179552 A1 | 8/2007 | Dennis et al. |
| 2007/0197939 A1 | 8/2007 | Wallace et al. |
| 2007/0219590 A1 | 9/2007 | Hastings et al. |
| 2007/0247786 A1 | 10/2007 | Aamodt et al. |
| 2007/0255295 A1 | 11/2007 | Starkebaum et al. |
| 2007/0255383 A1 | 11/2007 | Gerber et al. |
| 2007/0274565 A1 | 11/2007 | Penner et al. |
| 2007/0276461 A1 | 11/2007 | Andreas et al. |
| 2007/0293090 A1 | 12/2007 | Cowan et al. |
| 2007/0293909 A1 | 12/2007 | Cowan et al. |
| 2007/0293922 A1 | 12/2007 | Soltis et al. |
| 2007/0299498 A1 | 12/2007 | Perez et al. |
| 2008/0009750 A1 | 1/2008 | Aeby et al. |
| 2008/0051704 A1 | 2/2008 | Patel et al. |
| 2008/0071178 A1 | 3/2008 | Greenland et al. |
| 2008/0077227 A1 | 3/2008 | Ouellete et al. |
| 2008/0103578 A1 | 5/2008 | Gerber |
| 2008/0125844 A1 | 5/2008 | Swoyer et al. |
| 2008/0132981 A1 | 6/2008 | Gerber |
| 2008/0132982 A1 | 6/2008 | Gerber |
| 2008/0148554 A1 | 6/2008 | Merrill et al. |
| 2008/0172118 A1 | 7/2008 | Johnson et al. |
| 2008/0255475 A1 | 10/2008 | Kondrosky et al. |
| 2008/0262422 A1 | 10/2008 | Cahill |
| 2008/0269710 A1 | 10/2008 | Bonde et al. |
| 2008/0275350 A1 | 11/2008 | Liao et al. |
| 2008/0283066 A1 | 11/2008 | Delgado et al. |
| 2008/0300672 A1 | 12/2008 | Kassab et al. |
| 2009/0043367 A1 | 2/2009 | Zilberman et al. |
| 2009/0082828 A1 | 3/2009 | Ostroff |
| 2009/0082843 A1 | 3/2009 | Cox et al. |
| 2009/0099641 A1 | 4/2009 | Wu et al. |
| 2009/0105799 A1 | 4/2009 | Hekmat et al. |
| 2009/0131970 A1 | 5/2009 | Chanduszko et al. |
| 2009/0157092 A1 | 6/2009 | Blumenkranz et al. |
| 2009/0163969 A1 | 6/2009 | Donofrio |
| 2009/0177095 A1 | 7/2009 | Aeby et al. |
| 2009/0182412 A1 | 7/2009 | Tan et al. |
| 2009/0192514 A1 | 7/2009 | Feinberg et al. |
| 2009/0192585 A1 | 7/2009 | Bloom et al. |
| 2009/0192601 A1 | 7/2009 | Rafiee et al. |
| 2009/0234367 A1 | 9/2009 | Verma |
| 2009/0270741 A1 | 10/2009 | Vanney et al. |
| 2009/0275818 A1 | 11/2009 | Ran et al. |
| 2009/0299429 A1 | 12/2009 | Mayotte |
| 2009/0306539 A1 | 12/2009 | Woodruff et al. |
| 2009/0326346 A1 | 12/2009 | Kracker et al. |
| 2010/0004730 A1 | 1/2010 | Benjamin et al. |
| 2010/0030063 A1 | 2/2010 | Lee et al. |
| 2010/0030139 A1 | 2/2010 | Copa |
| 2010/0057009 A1 | 3/2010 | McQueen et al. |
| 2010/0063478 A1 | 3/2010 | Selkee |
| 2010/0076398 A1 | 3/2010 | Schemer et al. |
| 2010/0082087 A1 | 4/2010 | Silipo et al. |
| 2010/0094400 A1 | 4/2010 | Bolduc et al. |
| 2010/0168612 A1 | 7/2010 | Ducharme et al. |
| 2010/0179561 A1 | 7/2010 | Pilarski et al. |
| 2010/0185172 A1 | 7/2010 | Fabro |
| 2010/0234698 A1 | 9/2010 | Manstrom et al. |
| 2010/0274221 A1 | 10/2010 | Sigg et al. |
| 2010/0274227 A1 | 10/2010 | Khairkhahan et al. |
| 2010/0274345 A1 | 10/2010 | Rust |
| 2010/0304209 A1 | 12/2010 | Lund et al. |
| 2010/0305653 A1 | 12/2010 | Lund et al. |
| 2011/0160557 A1 | 6/2011 | Cinbis et al. |
| 2011/0190842 A1 | 8/2011 | Johnson et al. |
| 2011/0220274 A1 | 9/2011 | Erskine |
| 2011/0251662 A1 | 10/2011 | Griswold et al. |
| 2011/0264194 A1 | 10/2011 | Griswold |
| 2011/0270339 A1 | 11/2011 | Murray, III et al. |
| 2011/0313503 A1 | 12/2011 | Berra et al. |
| 2012/0029598 A1 | 2/2012 | Zhao |
| 2012/0095539 A1 | 4/2012 | Khairkhahan et al. |
| 2012/0172690 A1 | 7/2012 | Anderson et al. |
| 2012/0172691 A1 | 7/2012 | Brauker et al. |
| 2012/0172891 A1 | 7/2012 | Lee |
| 2012/0172892 A1 | 7/2012 | Grubac et al. |
| 2013/0253309 A1 | 9/2013 | Allan et al. |
| 2013/0253346 A1 | 9/2013 | Griswold et al. |
| 2014/0275991 A1 | 9/2014 | Potter et al. |
| 2015/0045868 A1 | 2/2015 | Boner et al. |

(56) References Cited

U.S. PATENT DOCUMENTS

| | | |
|---|---|---|
| 2015/0273207 A1 | 10/2015 | Tran et al. |
| 2016/0310703 A1* | 10/2016 | Drake ............... A61N 1/3756 |
| 2016/0310747 A1 | 10/2016 | Grubac et al. |
| 2017/0095662 A1 | 4/2017 | McDonnell et al. |
| 2017/0224997 A1 | 8/2017 | Shuros et al. |
| 2018/0028805 A1* | 2/2018 | Anderson .......... A61B 17/3468 |
| 2018/0318591 A1 | 11/2018 | Kabe et al. |
| 2019/0009078 A1 | 1/2019 | Kuhn et al. |

FOREIGN PATENT DOCUMENTS

| | | |
|---|---|---|
| WO | WO 200166151 A1 | 9/2001 |
| WO | WO 02/30295 A1 | 4/2002 |
| WO | WO 03/084398 A1 | 10/2003 |
| WO | WO 2004014456 A2 | 2/2004 |
| WO | WO 2005028023 A1 | 3/2005 |
| WO | WO 2007021340 A1 | 2/2007 |
| WO | WO 2007022180 A1 | 2/2007 |
| WO | WO 2009039400 A2 | 3/2009 |
| WO | WO 2009120636 A1 | 10/2009 |
| WO | WO 2009124287 A1 | 10/2009 |
| WO | WO 10/088687 A1 | 5/2010 |
| WO | 2015023486 A1 | 2/2015 |

OTHER PUBLICATIONS

International Search Report and Written Opinion of International Application No. PCT/US2020/031600, dated Jul. 22, 2020, 11 pp.

International Search Report and Written Opinion of International Application No. PCT/US2020/031601, dated Jul. 31, 2020, 9 pp.

Rozenman et al., "Wireless Acoustic Communication with a Miniature Pressure Sensor in the Pulmonary Artery for Disease Surveillance and Therapy of Patients With Congestive Heart Failure," J Am Coli Cardiol Feb. 2007; vol. 49, No. 7 pp. 784-790.

Medtronic, Inc., Cardiac Resynchronization Therapy for Heart Failure Management-Implant and Follow-up-Brief Overview 4 pages, 2002. (Applicant points out, in accordance with MPEP 609.04(a), that the year of publication, 2002, is sufficiently earlier than the effective U.S. filing date, so that the particular month of publication is not in issue.).

Luna Technologies, "About Distributed Sensing Technology", accessed on or about Dec. 28, 2010, 2 pp.

U.S. Appl. No. 16/146,391, filed Sep. 28, 2018, Drake et al.

U.S. Appl. No. 62/844,680, filed May 7, 2019, Drake et al.

\* cited by examiner

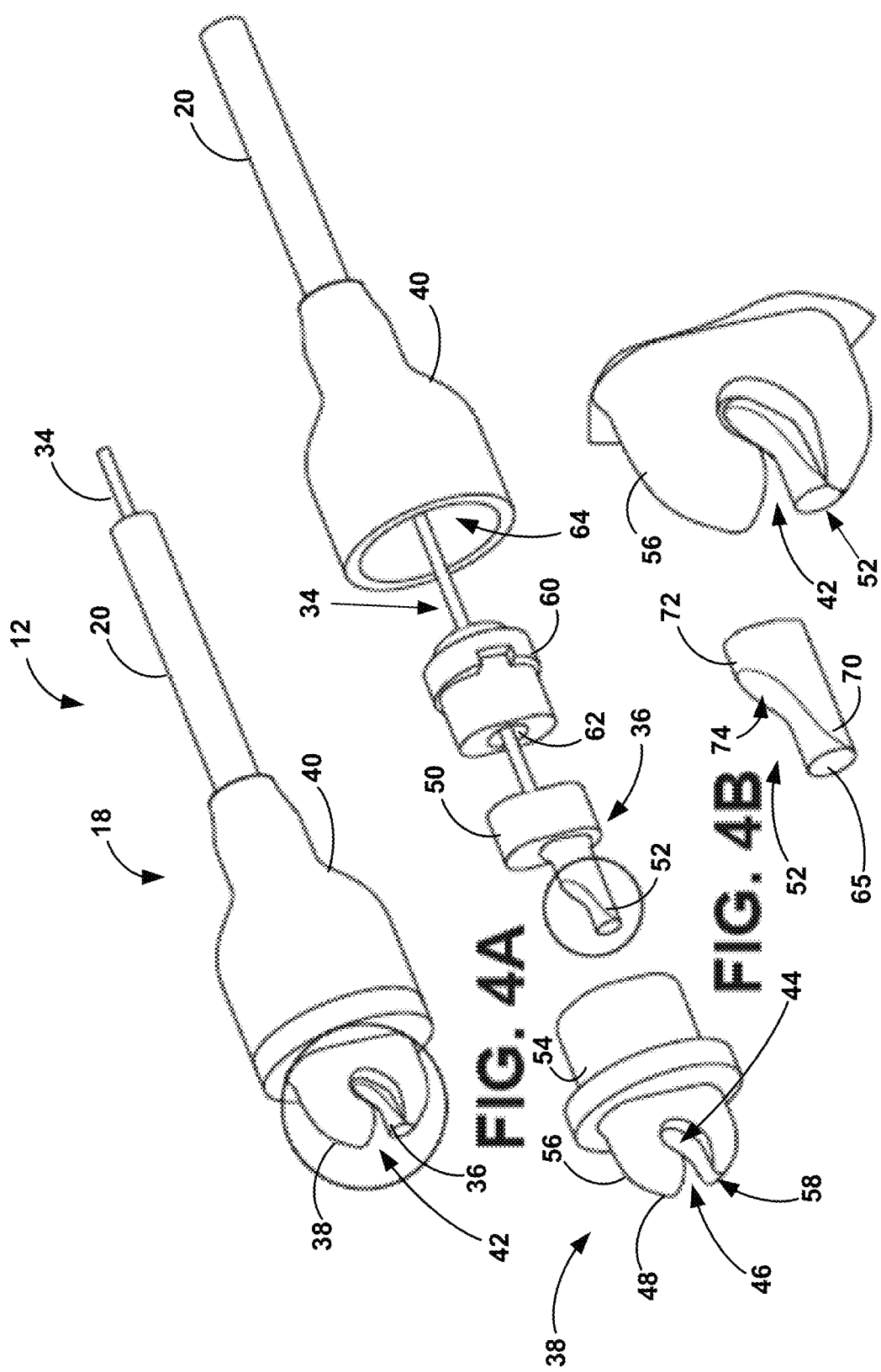

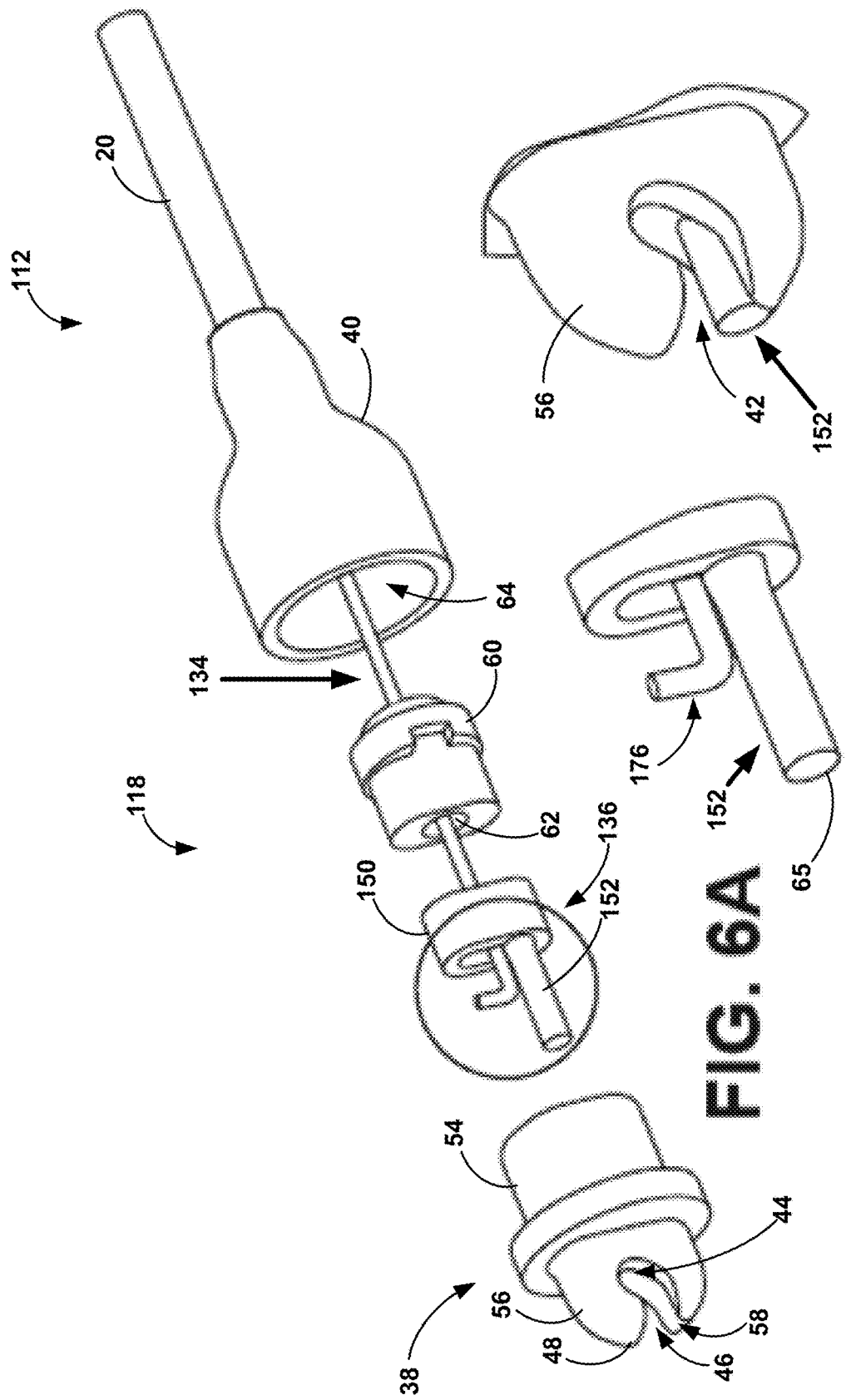

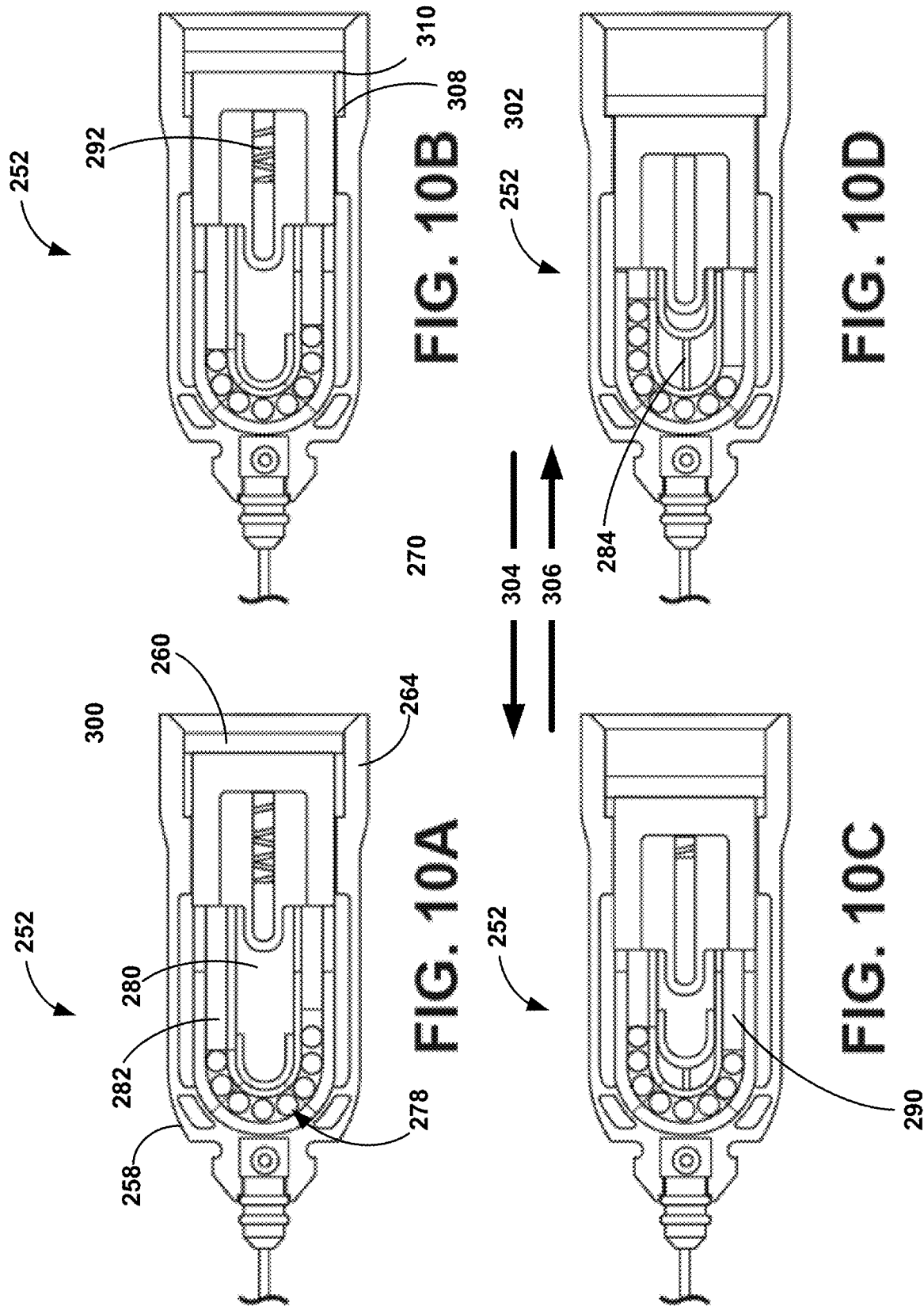

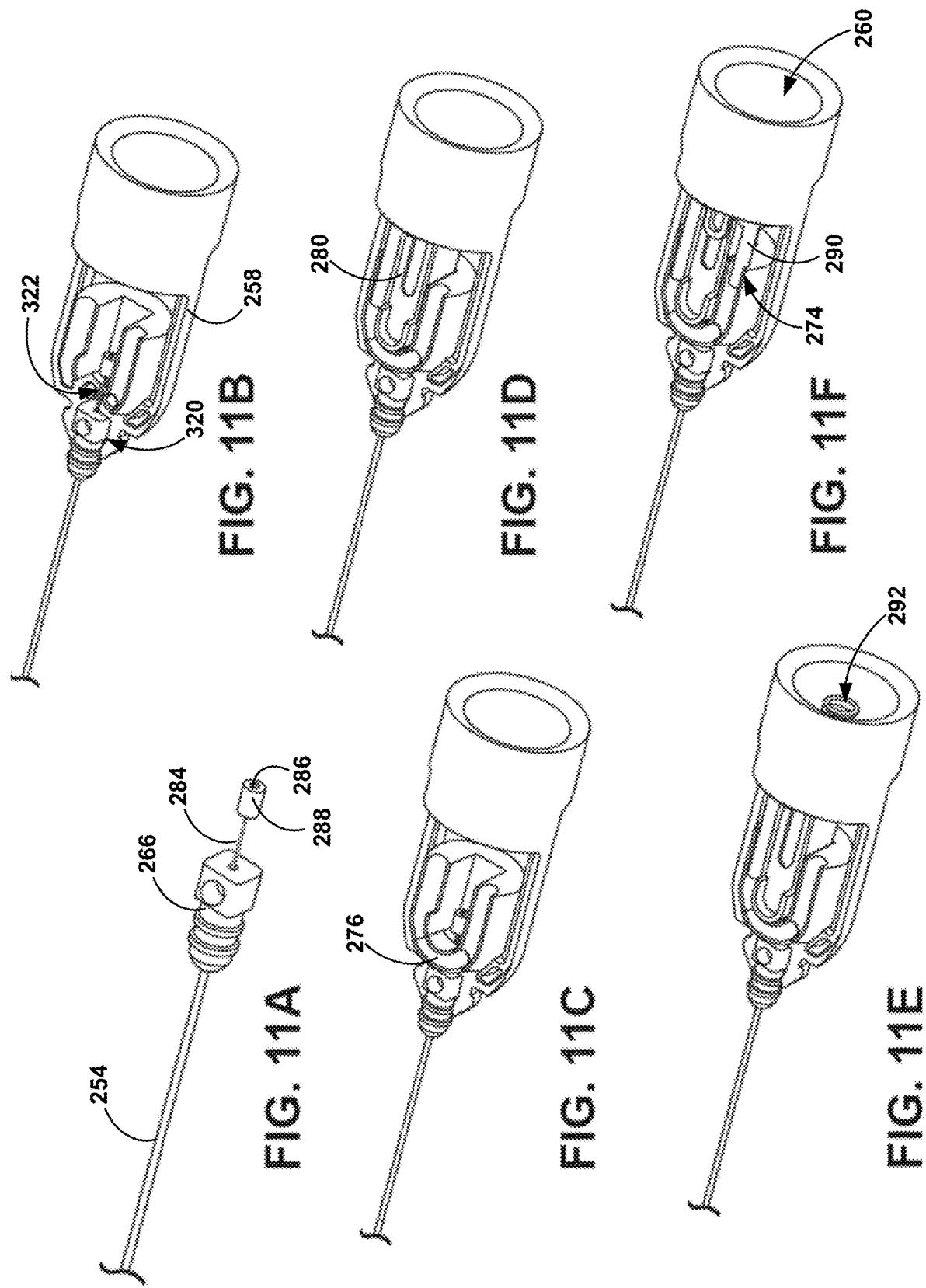

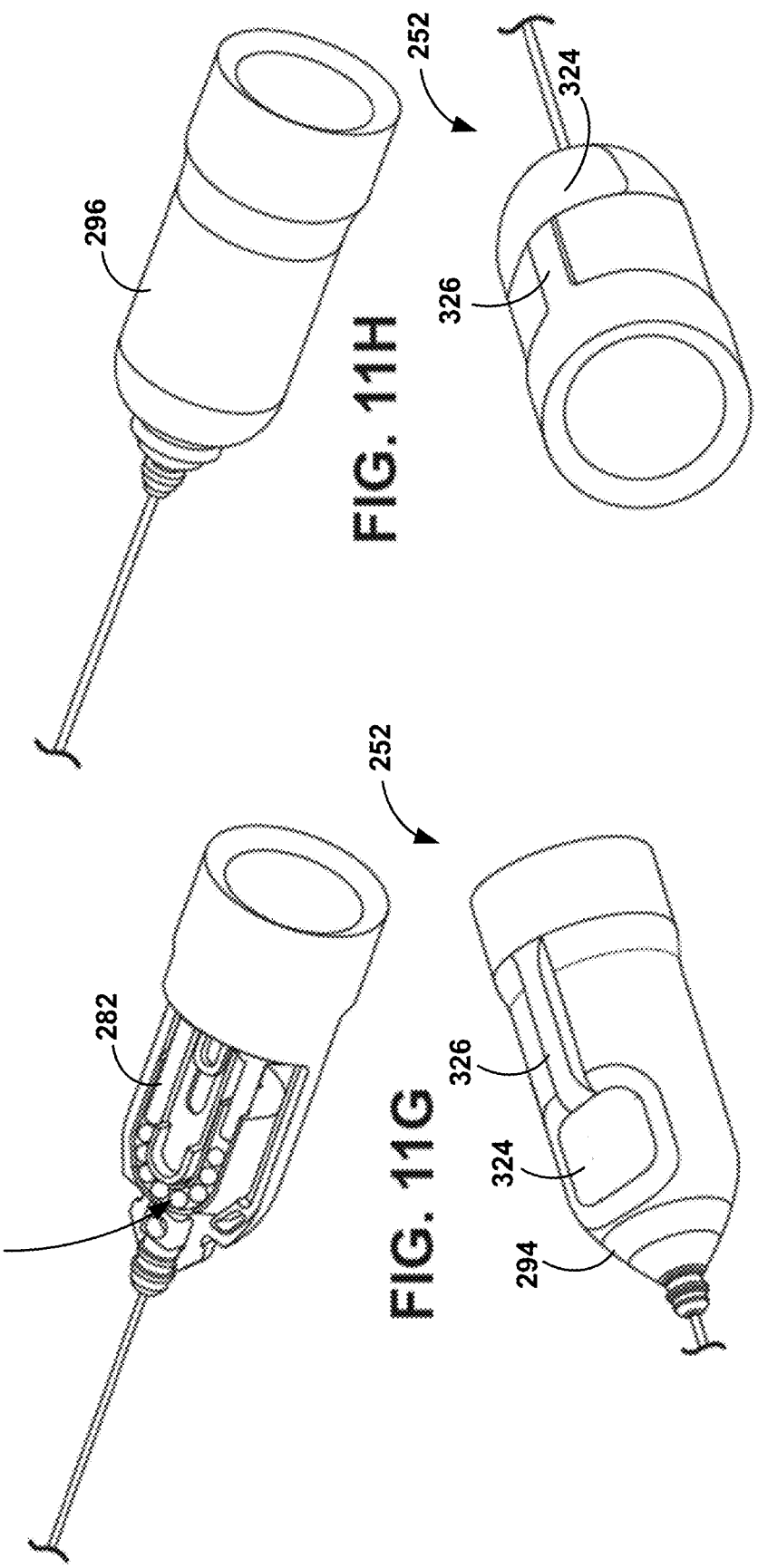

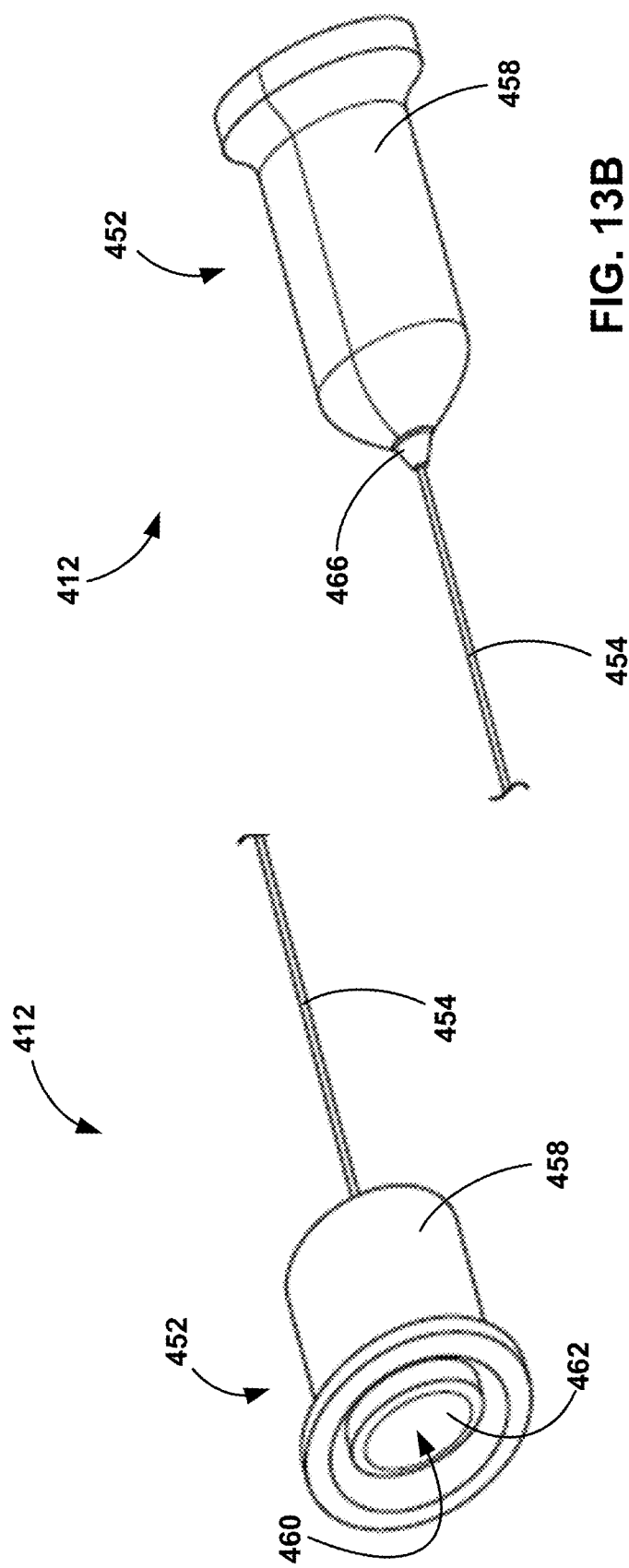

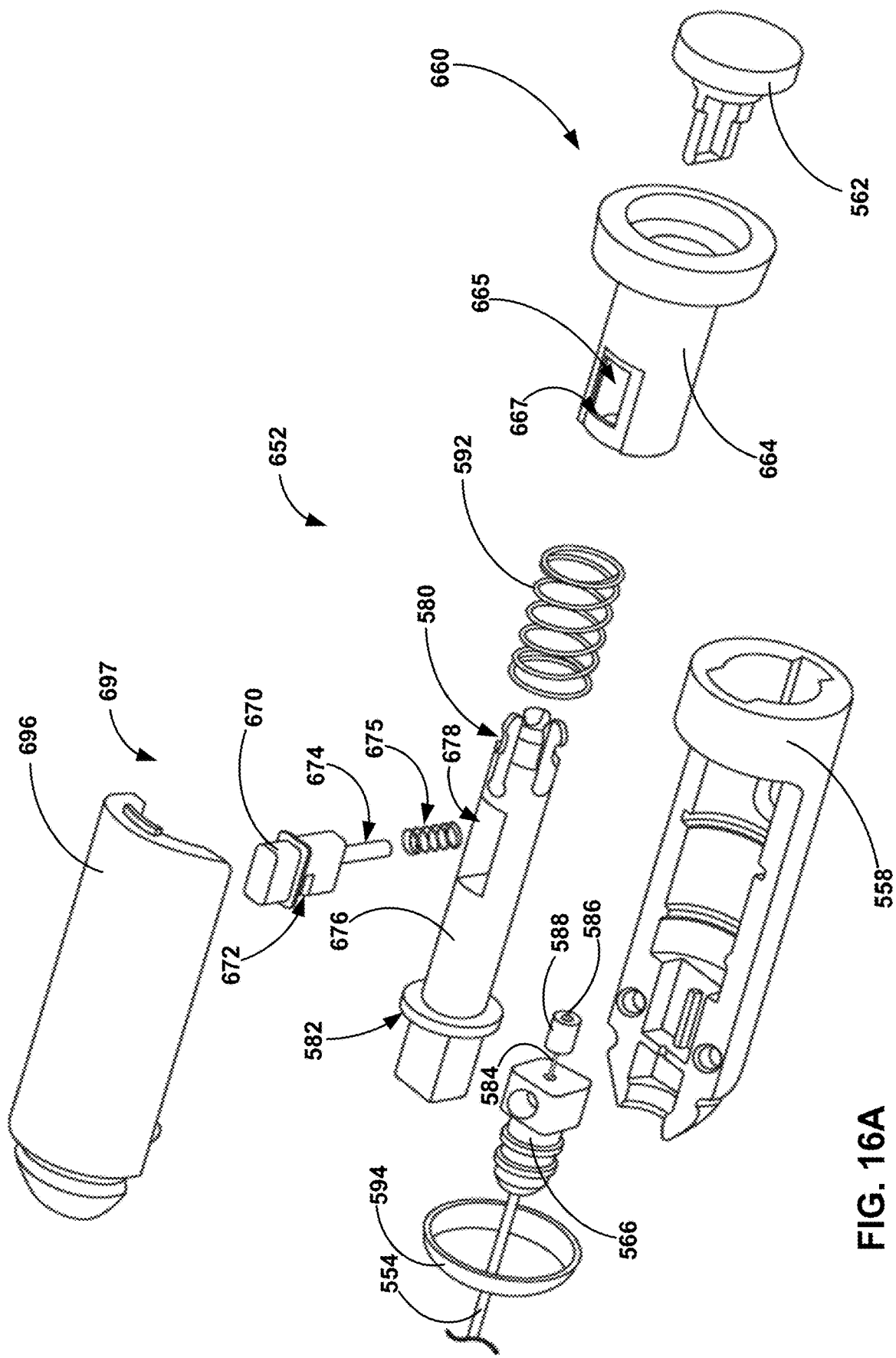

TETHER ASSEMBLIES FOR MEDICAL DEVICE DELIVERY SYSTEMS

This application claims the benefit of U.S. Provisional Application Ser. No. 62/844,674, filed May 7, 2019, the entire content of which is incorporated herein by reference.

TECHNICAL FIELD

This disclosure relates generally to medical devices, and, more particularly, to systems for delivering medical devices.

BACKGROUND

Some types of implantable medical devices (IMDs), such as cardiac pacemakers or implantable cardioverter defibrillators systems, may be used to provide cardiac sensing and therapy for a patient via one or more electrodes. Some IMDs include an implantable pulse generator that includes a housing that encloses electronic components, which may be configured to be implanted subcutaneously in the chest of the patient or within a chamber of a heart of the patient, as examples. IMDs having a pulse generator that is configured to be implanted within a chamber of the heart may be referred to as an intracardiac device or a leadless implantable medical device. A medical device delivery system including a delivery catheter may be used to deliver an intracardiac device transvenously to an implant site within a heart of a patient and release the device after the device has been fixed at the implant site. The medical device delivery system then may be withdrawn from the patient.

SUMMARY

In general, this disclosure is directed to examples of tether assemblies of medical device delivery systems and to techniques using such tether assemblies. Example tether assemblies may include a distal tether head assembly configured to releasably retain an attachment member of a medical device, e.g., an intracardiac device. Additionally, or alternatively, a tether assembly of a medical device delivery system may include a tether handle assembly configured to retain a proximal end of a pull wire of the tether assembly. The tether handle assembly includes one or more components (e.g., an actuator) configured to transmit force to a tether head assembly via the pull wire. The techniques may include applying a force to the actuator of the tether handle assembly move the pull wire, thereby enabling removal of the attachment member from the tether head assembly at a treatment site.

The tether head assembly may include an inner retainer and an outer retainer. The outer retainer may define an aperture including a receptacle configured to receive an attachment member of a medical device and a passageway extending from a distal end of the outer retainer proximally to the receptacle. The aperture further may include a groove extending from the distal end of the outer retainer proximally at least to the receptacle.

The inner retainer may be movable between a first position and a second position. When the inner retainer is in the first position, the distal portion of the inner retainer may be partially received in the groove and extend into the passageway, thereby narrowing the passageway. The passageway thus may be dimensioned to prevent passage of the attachment member therethrough when the inner retainer is in the first position, such as to prevent passage of the attachment member from the receptacle when the attachment member is loaded onto the tether assembly during a medical procedure to deliver the medical device. When the inner retainer is in the second position, the inner retainer does not narrow the passageway and the passageway thus may be dimensioned to receive the attachment member of the medical device, such as when the medical device is being loaded onto the tether assembly or released from the tether assembly.

The inner retainer may be biased to the first position. When the proximal movement of the pull wire is discontinued and/or when the attachment member has been passed through the passageway and is received within the receptacle defined by the outer member, an elastically-compressible member of the tether head assembly may expand and apply distally-directed force to the inner retainer, thereby moving the inner retainer from the second position to the first position.

In other examples, a tether head assembly configured to retain an attachment member of a medical device may include a retainer or other such component that is not biased to return to such a first position. The act of loading a medical device onto such other tether assemblies prior to delivery to a heart of a patient may require two people (e.g., clinicians). A first person may be required to hold the medical device in position while a second person opens the tether head assembly, such as by proximally moving a pull wire of the tether assembly to move the inner retainer from a first position in which the tether assembly is "closed" to a second position in which the tether assembly is "open." The first person then may load the attachment member of the medical device onto the tether head assembly (e.g., by placing the attachment member in a receptacle defined by the tether head assembly) and the second person may distally move the pull wire to return the tether head assembly to the first position and retain the attachment member within the receptacle. Loading a medical device onto a tether assembly using two people may add time and complexity to a medical procedure to deliver the medical device and/or may increase a possibility of contamination of the medical device or other objects within the surgical field.

Example tether head assemblies described herein may enable loading of a medical device onto a tether assembly by one person instead of two. For example, bias of the inner retainer to the first position may enable a clinician to hold the tether head assembly in one hand and simply press the attachment member into a passageway defined by an outer retainer, thereby moving the inner retainer to the second position as the attachment member moves through the passageway to the receptacle as an elastically-compressible member of the tether head assembly is compressed. The biasing of an inner retainer to a first position provided by the elastically-compressible member may enable the clinician to simply release his or her hold on the medical device once the attachment member is received within the receptacle allowing the inner retainer to return to the first position.

In this manner, the tether assemblies described herein may reduce the time and complexity associated with a procedure to deliver the medical device. In some examples, the tether assemblies described herein may reduce a possibility of contamination of the medical device or other objects within the surgical field by reducing the number of people that touch the medical device and the tether assembly. In some examples, the tether assemblies described herein may provide one or more advantages to the functionality, reliability, robustness, manufacturability, and cost associated with such tether assemblies.

In some examples, a tether handle assembly as described herein may be used in conjunction with a tether head assembly as described herein and a share pull wire. As an example, a tether assembly may include a tether head assembly, a pull wire, and a tether handle assembly attached to a proximal end of the pull wire. The tether handle assembly may include an actuator configured to cause a proximal movement of the pull wire that enables removal of the attachment member from the tether head assembly. Application of a force to the actuator may cause proximal movement of the pull wire, which may enable release of the medical device from the tether head assembly at a treatment site within a patient (e.g., within a heart of the patient). The force applied to the actuator may be a distally-directed force, e.g., a button push. In such examples, one or more components of the tether handle assembly may be configured to translate the distally-directed force applied to the actuator to a proximally-directed force applied to the pull wire.

Examples in which a tether handle assembly of a tether assembly of a medical device delivery system is configured to enable release of the medical device from the tether assembly by translating a distally-directed force into a proximally-directed force may provide one or more advantages. In some examples, a clinician may find applying a distally-directed force (i.e., a pushing force) to a button or slidable member to release the medical device to be intuitive and/or otherwise easier to use than some other tether handle assembly configurations. In some examples, a clinician may be less likely to accidentally release the medical device when using a tether handle assembly configured to enable release of the medical device from the tether assembly via distally-directed force relative to other actuator configurations.

Any such tether handle assemblies may include one or more components configured to reduce a possibility of accidental release of the medical device from the tether assembly, such as a lock member or a cover. Additionally, or alternatively, any of the handle assemblies described herein may enable sensing of electrical signals via an electrical path including the medical device and one or more components of a tether assembly including the tether handle assembly, which may help enable a clinician to determine positioning of the delivery and medical device relative to target tissue, attachment of the medical device to target tissue, and how much force to apply to an actuator of a tether handle assembly to enable release the medical device from the tether assembly.

In some other examples, a tether assembly of a medical device delivery system may not be re-usable, such as in other examples in which a tether assembly includes a string or other such component that is looped through the medical device and then cut after the medical device is fixed at a treatment site. In such other examples, a new tether assembly and/or medical device delivery system thus may be packaged with each medical device. Packaging a medical device delivery system and/or tether assembly with a medical device may be associated with shelf-life considerations, such as in examples in which the medical device includes a drug-eluting component that may have an expiration date.

The example tether assemblies described herein may be sterilizable and re-usable, at least in part because the tether assembly can be released from the medical device without being cut. In some examples, the tether assembly may be packaged separately from the medical device, such as examples in which the medical device may include a drug eluting component that has a finite shelf life. In such instances, packaging the tether assembly separately from medical device may mitigate shelf life considerations with respect to the tether assembly.

Thus, the example tether assemblies described herein may enable one-person loading of a medical device onto a tether assembly, may be more intuitive for a clinician to operate than some other example tether assemblies, may reduce a possibility of accidental deployment of a medical device, may enable a clinician to determine placement of the medical device at a treatment site within a patient (e.g., within a heart of the patient), and/or may enable a clinician to monitor electrical signals from the medical device and/or distal portion of the delivery system during an implantation procedure.

In one example, a tether assembly of a medical device delivery system comprises a pull wire defining a proximal end and a distal end, and a tether head assembly. The tether head assembly comprises an inner retainer comprising a proximal portion and a distal portion, wherein the inner retainer is coupled to and extends distally from the distal end of the pull wire, and an outer retainer comprising a proximal portion defining a channel configured to receive the inner retainer and a distal portion defining an aperture. The aperture comprises a receptacle configured to receive an attachment member of a medical device, a passageway extending from a distal end defined by the outer retainer proximally to the receptacle, wherein the passageway is narrower than the receptacle, and a groove extending from the distal end of the outer retainer proximally at least to the receptacle, wherein the groove has a depth that is less than a thickness of the distal portion of the inner retainer. The inner retainer is movable between a first position wherein the distal portion of the inner retainer is partially received in the groove and extends into the passageway, thereby narrowing the passageway, and a second position wherein the distal portion of the inner retainer is positioned proximal to the passageway.

In another example, a tether assembly of a medical device delivery system comprises a tether handle assembly comprising a housing defining a curved channel that defines a first end and a second end, a force transmitter received within the curved channel, a slidable member received within the housing such that a portion of the slidable member is received within the channel at the first end of the channel, and a button defining a proximal surface and comprising a distal portion received within the channel at the second end of the channel, wherein the button surrounds at least a proximal portion of the slidable member. The tether assembly further comprises a pull wire defining a proximal end and a distal end, wherein the proximal end of the pull wire is received within the housing and retained by the slidable member. The button is configured to move from a first position to a second position in response to application of a distally-directed force to the button, thereby moving the force transmitter toward the first end of the curved channel such that the force transmitter applies a proximally-directed force to the portion of the slidable member received within the channel that causes the slidable member and the pull wire to move proximally.

In another example, a method for using tether assembly of a medical device delivery system comprises positioning a tether head assembly of the tether assembly at a treatment site of a patient with an attachment member of a medical device received within a receptacle of the tether head assembly, the tether head assembly configured to releasably retain the attachment member of the medical device. The tether head assembly comprises an inner retainer comprising a proximal portion and a distal portion, wherein the inner retainer is coupled to and extends distally from the distal end of a pull wire of the medical device delivery system, an outer retainer comprising a proximal portion defining a channel configured to receive the inner retainer and a distal portion defining an aperture. The aperture comprises the receptacle configured to receive the tether member of the medical device, a passageway extending from a distal end of the outer retainer proximally to the receptacle, wherein the passageway is narrower than the receptacle, and a groove extending from the distal end of the outer retainer proximally at least to the receptacle, wherein the groove has a depth that is less than a thickness of the distal portion of the inner retainer. Positioning the tether head assembly comprises positioning the tether head assembly with the inner retainer in a first position wherein the distal portion of the inner retainer is partially received in the groove and extends into the passageway, thereby narrowing the passageway, wherein the passageway is dimensioned to prevent passage of the attachment member when the inner retainer is in the first position. The method further comprises applying a force to an actuator of the tether assembly to cause a proximal movement of the pull wire, the proximal movement of the pull wire moving the inner retainer from the first position to a second position wherein the distal portion of the inner retainer is positioned proximal to the passageway, wherein the passageway is dimensioned to receive the attachment member of the medical device when the inner retainer is in the second position, allowing the attachment member of the medical device to pass from the receptacle through the passageway. The method further comprises proximally moving the tether assembly with the inner retainer in the second position to remove the attachment member of the medical device from the tether head assembly, thereby delivering the medical device to the treatment site.

In another example, a tether assembly of a medical device delivery system comprises a tether handle assembly comprising a housing, a first slidable member defining a first aperture and received within the housing, a second slidable member received within the first aperture and defining a second aperture, and at least one gear received within the aperture defined by the first slidable member and configured to mechanically engage the first slidable member and the second slidable member. The tether assembly further comprises a pull wire defining a proximal end and a distal end, wherein the proximal end of the pull wire is received within the housing and is retained by the second slidable member. The first slidable member is configured to move distally in response to application of a distally-directed force to the first slidable member and, when the first slidable member moves distally, and the at least one gear moves the second slidable member and the pull wire proximally.

In another example, a tether assembly of a medical device delivery system comprises a tether handle assembly comprising a housing, a slidable member received within the housing, a plunger coupled to and extending distally from the slidable member. The tether assembly further comprises a pull wire defining a proximal end and a distal end, wherein the proximal end of the pull wire is received within the housing and is retained by the slidable member. The plunger is configured to move from a first position to a second position in response to application of a proximally-directed force to the plunger that causes the slidable member and the pull wire to move proximally.

In another example, a method for using a tether assembly of a medical device delivery system comprises positioning a tether head assembly of the tether assembly at a treatment site of a patient with an attachment member of a medical device received within a receptacle of the tether head assembly, the tether head assembly configured to releasably retain the attachment member of the medical device. The method further comprises applying a force in a distal direction to an actuator of a tether handle assembly of the tether assembly to cause a proximal movement of the pull wire, the proximal movement of the pull wire opening the tether head assembly, and proximally moving the tether assembly with the tether head assembly open to remove the attachment member of the medical device from the tether head assembly, thereby delivering the medical device to the treatment site.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF THE DRAWINGS

FIG. 4A is a plan view of a distal portion of an example tether assembly including a tether head assembly and pull wire, where a distal portion of the tether head assembly is outlined;

FIG. 4B is an exploded plan view of the distal portion of the example tether assembly of FIG. 4A, where a distal portion of an inner retainer of the tether head assembly is outlined;

FIG. 4C is a plan view of the distal portion of the inner retainer outlined in FIG. 4B;

FIG. 4D is a plan view of the distal portion of the tether head assembly outlined in FIG. 4A;

FIG. 6A is an exploded view of a distal portion of another example tether assembly including a tether head assembly and a pull wire, where a distal portion of an inner retainer of the tether head assembly of FIG. 6A is outlined;

FIG. 6B is a plan view of the distal portion of the inner retainer outlined in FIG. 6A;

FIG. 6C is a plan view of the distal portion of the inner retainer of FIG. 6B received within an outer retainer of the tether head assembly of FIG. 6A;

FIGS. 10A-10D are side views of the tether handle assembly of FIGS. 9A and 9B with a portion of a housing of the tether handle assembly removed, illustrating movement of a force transmitter, a slidable member, and a pull wire of the example tether assembly of FIGS. 9A and 9B in response to movement of a button of the tether handle assembly from a first position to a second position;

FIGS. 11A-11J are plan views of components of the tether handle assembly of the example tether assembly of FIGS. 9A and 9B, illustrating an example technique for assembling the tether handle assembly;

FIGS. 13A and 13B are plan views of a proximal end of another example tether assembly including another example tether handle assembly;

FIG. 16A is an exploded plan view of another example tether handle assembly;

DETAILED DESCRIPTION

In general, this disclosure describes example medical device delivery systems. Such medical device delivery systems may include a tether assembly comprising a tether head assembly, and tether handle assembly, and a pull wire. The tether head assembly is attached to the pull wire and configured to releasably retain an attachment member of a medical device (e.g., an intracardiac device). In some examples, a tether handle assembly is configured to retain the pull wire attached to the tether head assembly. The tether handle assembly may include an actuator configured to transmit force to the tether head assembly via the pull wire and enable removal of the attachment member of a medical device from the tether head assembly at a treatment site within a patient. Although the example tether assemblies are generally described herein as being configured for delivering an implantable medical device (IMD), it should be understood that any of the example tether assemblies described herein alternatively may be configured for delivering other types of medical devices.

Figure 1:
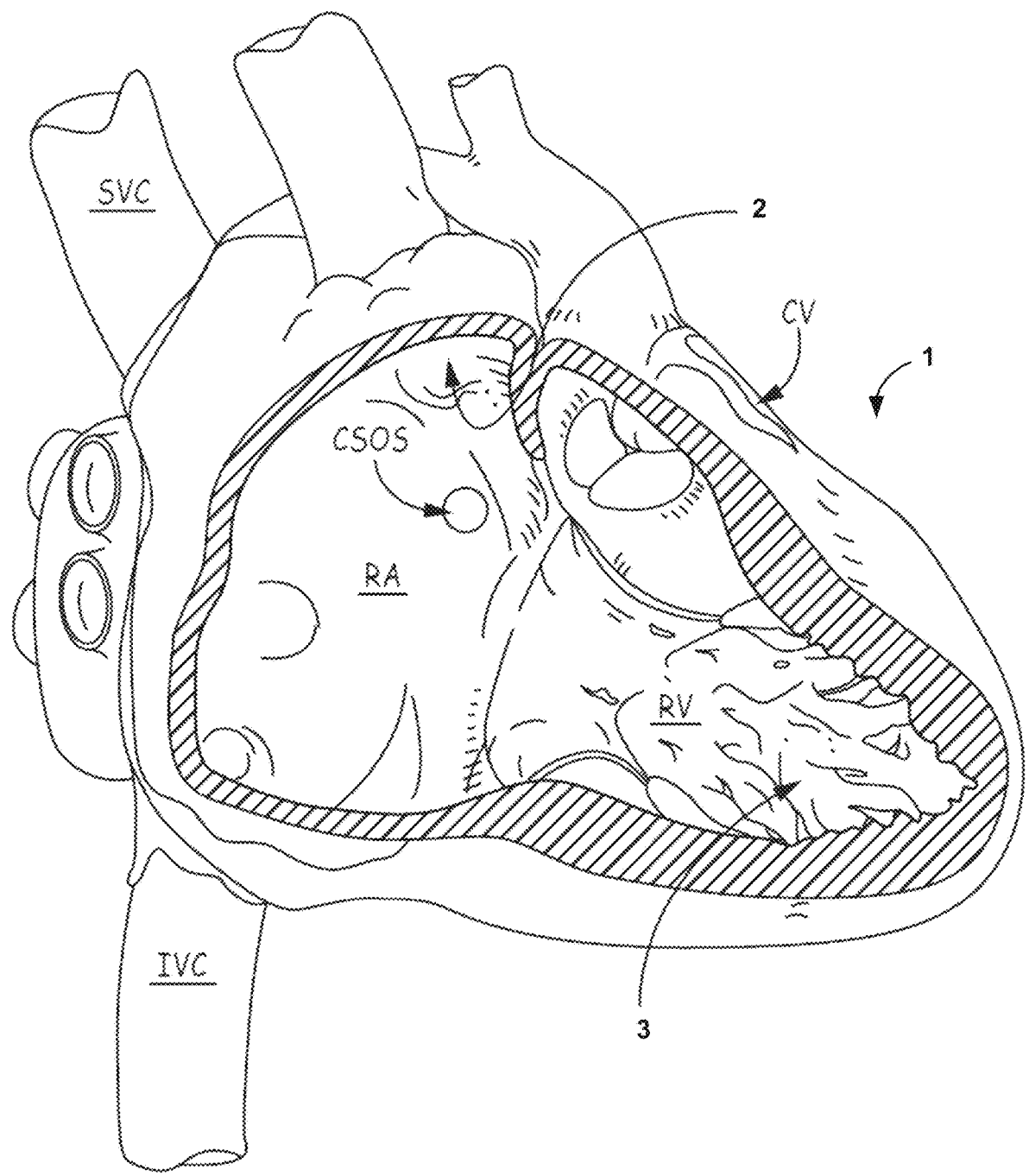
FIG. 1 is a conceptual drawing illustrating portions of patient anatomy including potential implant sites for an implantable medical device (IMD)

FIG. 1 is a conceptual drawing illustrating portions of patient anatomy including potential implant sites for an IMD. For example, an IMD may be implanted on or within heart 1 of a patient, such as within an appendage 2 of a right atrium (RA), within a coronary vein (CV) via a coronary sinus ostium (CSOS), or in proximity to an apex 3 of a right ventricle (RV). In other examples, an IMD may be implanted on other portions of heart 1 or implanted in locations other than heart 1, such as any suitable implant site in a body of the patient.

Figure 2:
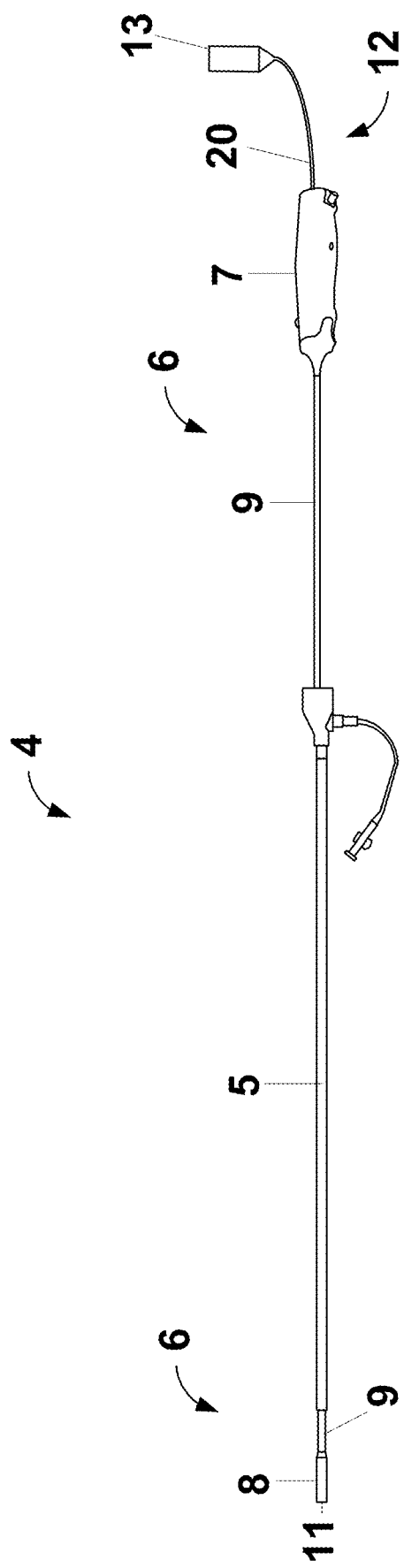
FIG. 2 is a plan drawing illustrating an example medical device delivery system for delivering an IMD to a location within a heart.

FIG. 2 is a plan drawing illustrating an example medical device delivery system 4 for delivering an IMD (not shown in FIG. 1) to a location within heart 1. Although described herein in the context of delivering an IMD into the vasculature, e.g., heart 1, the devices, systems, and techniques of this disclosure may be used to deliver an IMD to any anatomical location.

System 4 includes an introducer 5, a delivery catheter 6, and a tether assembly 12. Introducer 5 is an elongated member defining an interior lumen. Introducer 5 is configured to be inserted, such as by a physician, into a vasculature of a patient to provide a rigid channel, via the interior lumen, through which to insert a medical instrument, a device, or other therapy.

Delivery catheter 6 is configured to be inserted through the lumen of introducer 5 to deliver an IMD within the vasculature. Delivery catheter 6 includes an elongated shaft 9, a handle 7, and a device cup 8. Handle 7 is disposed at a proximal end of shaft 9, and may include one or more elements (such as buttons, switches, etc.) configured to control the motion of the distal end of shaft 9 and release of the IMD from device cup 8, as examples.

Device cup 8 is disposed at a distal end of shaft 9. Device cup 8 includes a hollow cylindrical body configured to house and support an IMD (e.g., IMD 10 described with respect to FIG. 3) while the IMD is being implanted within a vasculature of a patient. For example, a physician may insert the distal end of delivery catheter 6, including device cup 8, through the lumen of introducer 5, which is disposed within a vasculature of a patient. Once device cup 8 has extended through the distal end of introducer 5 and reached an implant site within the patient, the physician may release the IMD from a distal opening 11 of device cup 8 and withdraw delivery catheter 6 proximally through introducer 5.

Tether assembly 12 extends through a lumen defined delivery catheter, e.g., including handle 7 and shaft 9. Tether assembly 12 an elongate body 20, a tether handle assembly 13 at a proximal end of elongate body 20, and a tether head assembly 18 (FIG. 3) at a distal end of elongate body 20. A pull wire (not shown in FIG. 2) may extend from tether handle assembly 13 to tether head assembly 18 through a lumen defined by elongate body 20.

Tether assembly 12 may be of sufficient length that a clinician may manipulate tether handle assembly 13 to advance tether head assembly 18 out of distal opening 11 of cup 8. In some examples, with tether head assembly 18 outside of cup 8, a clinician may attach an IMD to tether head assembly 18 as described herein. The clinician may then load the IMD into cup 8 via distal opening 11, and advance delivery catheter 6, with tether assembly 12 and the IMD therein, through introducer 5 and into the vasculature.

Figure 3:
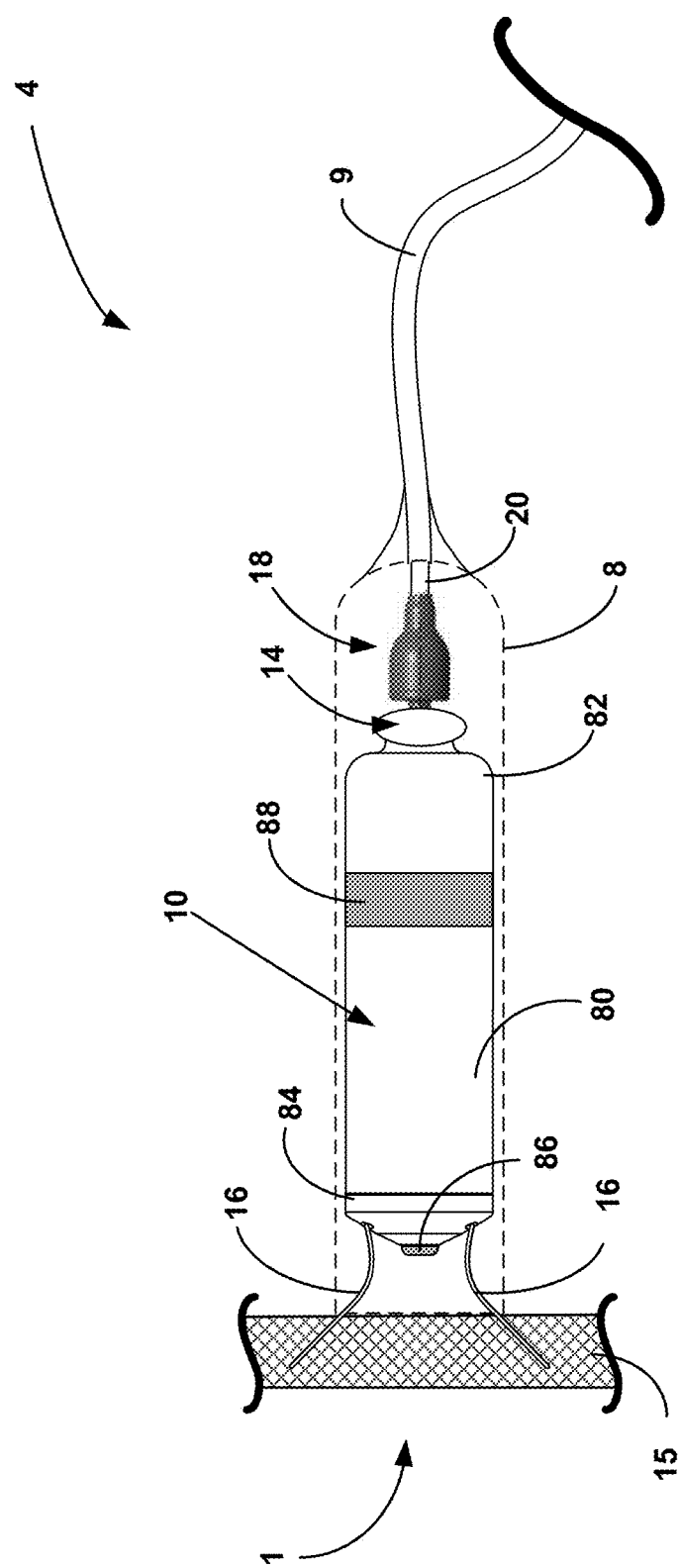
FIG. 3 is a conceptual drawing illustrating, in conjunction with tissue of a heart, a distal portion of the example medical device delivery system of FIG. 2 carrying an example IMD.

FIG. 3 is a conceptual drawing illustrating, in conjunction with tissue 15 of heart 1, a distal portion of medical device delivery system 4 carrying an example IMD 10. IMD 10 may be a pacemaker device having a housing 80 that contains electronic components suitable for performing a variety of pacing functions. However, IMDs configured to deliver other types of electrical therapy to a patient may be adapted for use with delivery system 4. IMD 10 may include an attachment member 14 at a proximal end thereof and fixation members 16 at a distal end thereof. Tether head assembly 18 may be configured to receive and retain attachment member 14, as further discussed below with respect to FIGS. 4A-5D.

In some examples, IMD 10 may include a hermetically sealed housing 80 defining a proximal end 82 and a distal end 84. Housing 80 may contain a pulse generator and an associated power supply (not shown) and an electrode 86, which may be positioned at distal end 84 of housing 80 and which may be electrically coupled to the pulse generator of IMD 10 via a hermetically sealed feedthrough assembly (not shown). Housing 80 may be formed from any suitable biocompatible and biostable metal. For example, housing 80 may be formed from titanium and may be overlaid with an insulative layer (e.g., a medical grade polyurethane, parylene, or silicone). In some examples, IMD 10 may include a housing electrode 88, which may be formed by removing a portion of the insulative layer to expose a metallic surface defined by housing 80. In such examples, housing electrode 88 of IMD 10 may function in conjunction with electrode 86, such as for bipolar pacing and sensing.

FIG. 3 illustrates the distal end cup 8 of delivery catheter 6 pressed against tissue 15 at the implant site of heart 1. When a clinician is satisfied with the positioning of cup 8 with respect to tissue 15, e.g., that a longitudinal axis of cup 8 is generally orthogonal to a plane defined by tissue 15, and that cup 8 pressed sufficiently against/into tissue 15 such that fixation members 16 of IMD 10 will deploy into the tissue, the clinician may advance IMD 10 towards distal opening using tether assembly 12, e.g., by using tether assembly handle 13 to advance tether assembly 12 distally relative to delivery catheter 6. Fixation members 16 may be configured to embed into tissue 15, and in some cases pull IMD 10 through distal opening 11 of cup, when advanced through the distal opening. While IMD 10 is shown having fixation members 16 that includes a plurality of tine structures, it should be understood that IMD 10 may include any other suitable fixation structure or structures, such as a screw-shaped fixation structure (helix) that may be rotated into tissue at an implant site.

IMD 10 may, for a time, remain attached to tether assembly 12 by attachment member 14 and tether head assembly 18 while fixed to tissue 15 by fixation members 16. Thus, the clinician may be able to test the fixation of IMD 10 at the implant site and/or remove IMD 10 from the implant site and back into cup 8 for repositioning at a more suitable site, if necessary. Once satisfied with the implantation of IMD 10, the clinician can separate tether head assembly 18 from attachment mechanism 14 and move tether assembly 12 proximally, as described in greater detail below, and then withdraw delivery catheter 6 and tether assembly 12 from the patient through introducer 5.

For example, tether assembly 12 may include a pull wire (not shown) as discussed in further detail with respect to FIGS. 4A-5D. Such a pull wire may be attached at a distal end thereof to tether head assembly 18 and attached at a proximal end thereof to tether handle assembly 13, examples of which are discussed below with respect to FIGS. 9A-17C. The clinician may apply force to an actuator of tether handle assembly to cause tether head assembly 18 to move from a closed position, in which attachment member 14 is retained within tether head assembly 18, to an open position in which attachment member 14 may be released from tether head assembly 18. With tether head assembly 18 in the open position, the clinician may proximally move tether assembly 12 to remove attachment member 14 from tether head assembly 18, leaving IMD 10 fixed at the treatment site.

A clinician may secure attachment member 14 of IMD 10 to tether head assembly 18 by pressing attachment member 14 into a passageway defined by tether head assembly 18, thereby opening tether head assembly 18 from a first (e.g., closed) position to a second (e.g., open) position and advancing attachment member 14 through the passageway until tether member 14 is received within a receptacle defined by tether head assembly 18, as further discussed below with respect to FIGS. 4A-5D. This may be accomplished by one clinician instead of the two clinicians that may be required to secure an attachment member of an IMD to a tether assembly in some other example medical device delivery systems. Thus, tether assembly 12 may reduce the time and complexity associated with a procedure to deliver IMD 10. In some examples, tether head assembly 18 may reduce a possibility of contamination of the medical device or other objects within the surgical field, relative to such other tether assemblies, by reducing the number of people that touch IMD 10 and tether head assembly 18.

As described herein, a clinician may secure attachment member 14 of IMD 10 to tether head assembly 18 at the time of a medical procedure to deliver IMD 10. In addition, the clinician may release IMD 10 from tether head assembly 18 without cutting a portion of tether assembly 12. In some examples, tether head assembly 18 thus may reduce or eliminate drawbacks that may be associated with other types of tether mechanisms, such as tension associated with pulling on such other tether mechanisms (e.g., a loop of string or similar material), potential twisting or binding of such other tether mechanisms, or the like. The re-usability of tether assembly 12 may mitigate shelf life considerations with respect to tether assembly 12, delivery system 4, and IMD 10, such as in examples in which IMD 10 includes a drug eluting component with a finite shelf life. For example, tether assembly 12 and/or delivery system 4 may not necessarily be associated with a finite shelf life when packaged separately from IMD 10.

During delivery of IMD 10 to the treatment site via delivery system 4, a clinician may advance cup 8 into contact with tissue 15 of heart 1 prior to engaging fixation members 16 with tissue 15 of heart 1. The clinician then may determine whether cup 8 and IMD 10 are properly positioned at the implant site prior to engaging fixation members 16 with the tissue 15 of heart 1. In some examples, the clinician may determine whether cup 8 and IMD 10 is properly positioned relative to heart 2 based on an impedance or other electrical signal sensed via an electrical path including IMD 10 (e.g., housing 80 or an electrode 88), attachment member 14, and one or more components of tether assembly 12 (e.g., one or more components of tether head assembly 18). In addition to the IMD, another electrode of the electrical path may be a reference electrode attached to the patient, or inside the patient but located outside of cup 8. In some examples, relatively higher impedance may be indicative of cup 8 being positioned flush against, and with adequate depth in, tissue 15 of heart 1, which may be desirable for proper fixation. After deployment of fixation members 16 and IMD 10 from cup 8, with IMD 10 fixed to tissue 15, an impedance or electrical signal may also indicate the quality of the fixation of IMD 10 to tissue, e.g., based on variations of the impedance during a "tug test" in which a clinician pulls on tether assembly 12 while attached to IMD 10 and while IMD 10 is fixed to tissue 15. Some examples may employ any of the techniques for testing the spatial relationship of a cup and/or IMD to tissue, and for testing fixation of an IMD to tissue, described in U.S. patent application Ser. No. 16/146,391, filed Sep. 28, 2018 by Medtronic, Inc., and titled "Impedance-Based Verification for Delivery of Implantable Medical Devices," which is incorporated herein by reference in its entirety.

FIGS. 4A-6D illustrate examples of distal portions of tether assemblies including example tether head assemblies. It should be noted that although FIGS. 4A-6D may be described with respect to IMD 10, delivery systems may be used to deliver other suitably configured medical devices.

FIG. 4A is a plan view of a distal portion of a tether assembly 12 with the components of tether assembly 12 in an assembled configuration, where a distal portion of a tether head assembly 18 is outlined. FIG. 4B is an exploded plan view of the distal portion tether assembly 12, where a distal portion of an inner retainer 36 of tether head assembly 18 is outlined. FIG. 4C is a plan view of the distal portion of the inner retainer 36 outlined in FIG. 4B. FIG. 4D is a plan view of the distal portion of the tether head assembly 18 outlined in FIG. 4A.

As illustrated in FIG. 4A, elongate body 20 may include a shaft defining a lumen (not shown) in which a portion of a pull wire 34 is received. Tether head assembly 18 may include inner retainer 36, an outer retainer 38, and a sheath 40. Components of tether assembly 12 may be separately formed of any suitable material. In some examples, one or more of pull wire 34, inner retainer 36, outer retainer 38, sheath 40, and/or one or more layers of elongate body 20 may be formed of an electrically conductive material, which may help enable testing of placement of IMD 10 during a procedure to deliver IMD 10, as discussed above with respect to FIG. 3. One or more components of tether assembly 12 may be manufactured via a technique such as metal injection molding or any other suitable technique.

Inner retainer 36 may be coupled to pull wire 34 and extends distally of from a distal end (not shown) of pull wire 34. A distal portion 56 of outer retainer 38 defines an aperture 42 that, as illustrated in FIG. 4B includes a receptacle 44 dimensioned to receive attachment member 14 of IMD 10 and a passageway 46. Passageway 46 may extend from a distal end 48 defined by outer retainer 38 proximally to receptacle 44 and may be narrower than receptacle 44.

A proximal portion 54 of outer retainer 38 may define a channel (not shown) configured to receive inner retainer 36. Inner retainer 36 may be received within outer retainer 38 in a first position in which a distal portion 52 of inner retainer 36 extends into passageway 46, as shown in FIGS. 4A and 4D. When inner retainer 36 is in the first position, passageway 46 may be dimensioned to prevent passage of attachment member 14 of IMD 10 (e.g., is too narrow to allow passage of attachment member 14).

Proximal movement of pull wire 34 may cause movement of inner retainer 36 from the first position to a second position in which inner retainer 36 does not extend into passageway 46. Additionally, or alternatively, an application of force to inner retainer 36, e.g., a distal end of inner retainer 36, by attachment member 14 of IMD 10 may cause inner retainer 36 to move from the first position to the second position. With inner retainer 36 in the second position, passageway 46 may be dimensioned to receive tether member 14. Inner retainer 36 and outer retainer 38 may be received within sheath 40, and more particularly a cavity 64 defined by sheath 40, which may help retain inner retainer 36 within outer retainer 38 and couple outer retainer 38 to elongate body 20.

In some examples, the configuration of inner retainer 36 and outer retainer 38 may substantially isolate the function of retaining attachment member 14 of IMD 10 to tether head assembly 18, rather than pull wire 34 or another element that extends to a handle assembly of tether assembly 12. For example, as tether assembly 12 is navigated through curved portions of patient vasculature, the path lengths of pull wire 34 and/or shaft 20 may change. In some other example medical device delivery systems in which the tether assembly relies on a pull wire to retain an attachment member within a tether head assembly, such changes in path lengths of a pull wire and/or shaft may cause a loss of contact between the pull wire and the attachment member, thereby adversely affecting retention of the attachment member during delivery.

In the example of tether assembly 12 and other tether assemblies described herein, changes in path length of pull wire 34 and/or shaft 20 of tether assembly 12 may not cause substantial proximal or distal movement of inner retainer 36. For example, sheath 40 and/or an elastically-compressible member 60 may help reduce or prevent proximal movement of inner retainer 36 as path lengths of pull wire 34 and/or shaft 20 change during navigation of curved vasculature. In this manner, the substantial isolation of the IMD retention function within tether head assembly 18 may help maintain retention of attachment member 14 as tether assembly 12 is navigated through curved vasculature.

In FIG. 4B a distal portion of inner retainer 36 is outlined, and that portion of inner retainer 36 is illustrated in greater detail in FIG. 4C. As shown in FIG. 4B, inner retainer 36 may include a proximal portion 50 and a distal portion 52. Outer retainer 38 may include a proximal portion 54 and a distal portion 56. Proximal portion 54 of outer retainer 38 may define a channel (not shown) dimensioned to receive proximal portion 50 of inner retainer 36. Distal portion 56 of outer retainer 38 may define aperture 42. In some examples, aperture 42 may further include a groove 58 extending from distal end 48 of outer retainer 38 proximally at least to receptacle 44. Groove 58 may be partially defined by distal portion 56 of outer retainer 38 and may have a depth that is less than a thickness of distal portion 52 of inner retainer 36. A value by which the thickness of distal portion 52 of inner retainer 36 exceeds the depth of groove 58 may correspond to a distance that inner retainer 36 extends, e.g., transverse to a longitudinal axis defined by inner retainer 36, into passageway 46.

FIG. 4B further illustrates elastically-compressible member 60, which is receivable within cavity 64 defined by sheath 40 proximal of, e.g., in an abutting relationship with, inner retainer 36. Elastically-compressible member 60 may be formed of a suitably elastically-compressible material, such as a polymer. Elastically-compressible member 60 may define a lumen 62 through which a distal portion of pull wire 34 may extend and be attached to more distally located inner retainer 36. In some examples, elastically-compressible member 60 may be configured to bias inner retainer 36 to the first position. For example, elastically-compressible member 60 may define a longitudinal axis, which may correspond to a longitudinal axis of tether assembly 18. Axial expansion of elastically-compressible member 60 relative to the longitudinal axis causes elastically-compressible member 60 to apply a distally-directed force to inner retainer 36, thereby causing inner retainer 36 to move from the second position to the first position.

In this manner, elastically-compressible member 60 may function as a spring that biases inner retainer 36 to the first position. Biasing of inner retainer 36 to the first position may provide one or more advantages, such as enabling a clinician to load IMD 10 onto tether head assembly 18 without necessarily requiring the assistance of another clinician. Elastically-compressible member 60 may be received within sheath 40 when tether assembly 12 is in an assembled configuration, e.g., shown in FIG. 4A. In this manner, sheath 40 may provide a backstop against which elastically-compressible member 60 may be compressed during movement of inner retainer 36 from the first position to the second position.

The form of elastically-compressible member 60 illustrated in FIG. 4B is an example. In other examples, other forms of elastically-compressible member may be used to provide the functionality described with respect to elastically-compressible member 60 herein. For example, an elastically-compressible member may take the form of a coil or spring. Additionally, elastically-compressible members may be formed from a variety of materials, such as polymers or metals.

FIG. 4C is a plan view of distal portion 52 of inner retainer 36 outlined in FIG. 4B. As illustrated in FIG. 4C, distal portion 52 of inner retainer 36 may define a first portion 70, a second portion 72, and a third portion 74. First portion 70 may include the distal end of inner retainer 36 and may have a first thickness. Second portion 72 may be proximal to first portion 70 and may have a second thickness that is greater than the first thickness of first portion 70. Third portion 74 may extend between first portion 70 and second portion 72 and may taper in thickness from the first thickness of first portion 70 to the second thickness of second portion 72. In this manner, the tapered thickness of third portion 74 may define a "ramp" surface from proximal portion 70 toward second portion 72 and receptacle 44.

When attachment member 14 of IMD 10 is received in receptacle 44 (e.g., when inner retainer 36 is in the first position), the ramp surface defined by third portion 74 may help ensure substantially constant physical contact between attachment member 14 and at least third portion 74 of inner retainer 36. The physical contact between attachment member 14 and inner retainer 36 enabled by third portion 74 is illustrated in FIG. 5D and further discussed with respect thereto.

In some examples, inner retainer 36 and attachment member 14 may be electrically conductive. In such examples, ensuring substantially constant physical contact between attachment member 14 and inner retainer 36 during a method of delivering IMD 10 may enable use as an electrical connection and/or may help reduce electrical noise that otherwise may be caused by intermittent contact between attachment member 14 and inner retainer 36. A reduction in such electrical noise may help enable determination of whether IMD 10 is properly positioned and/or affixed relative to tissue of heart 1 during electrical testing of IMD 10 prior to release of IMD 10 from tether head assembly 18 at the implant site.

FIG. 4D illustrates a manner in which distal portion 52 of inner retainer 36 may be received within groove 58 defined by distal portion 56 of outer retainer 38 when inner retainer 36 is in the first position. In some examples, groove 58 may extend proximally from distal end 48 of outer retainer 38 toward receptacle 44. In some examples, groove 58 may extend proximally past receptacle 44 toward proximal portion 54 of outer retainer 38. In any such examples, groove 58 may help provide support to distal portion 52 of inner retainer 36, such as by reducing a possibility of distal portion 52 being bent sideways during loading of attachment member 14 of IMD 10 into receptable 44, or other use of tether assembly 12. In this manner, groove 58 may help maintain the mechanical integrity and functionality of tether assembly 12 during one or more uses, thereby contributing to the durability of tether assembly 12.

Figure 5A:
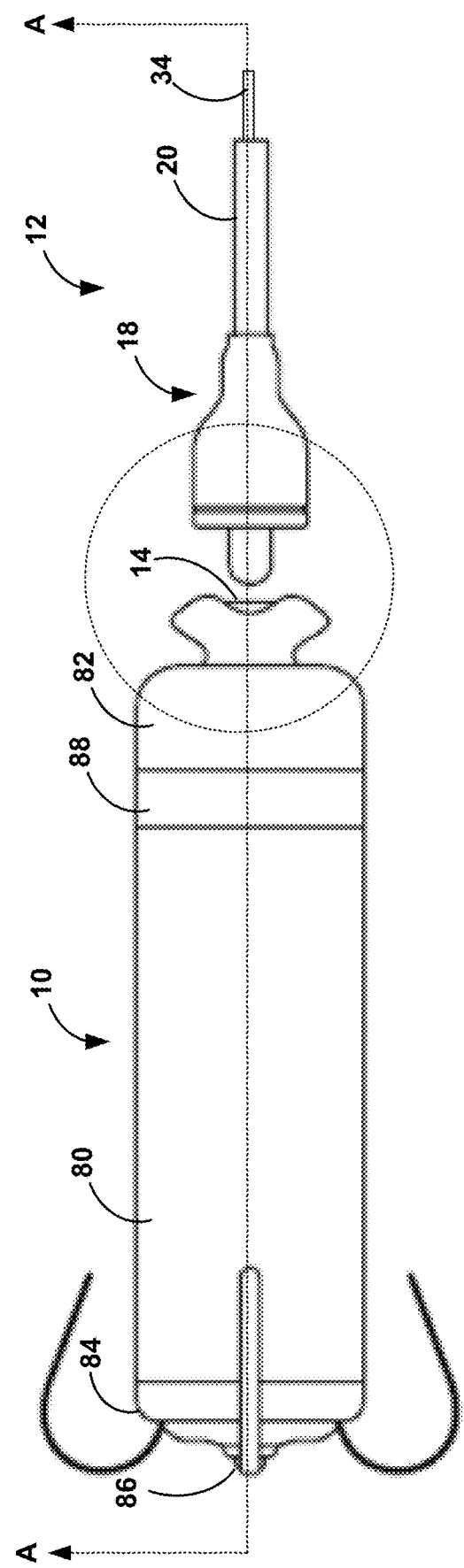
FIG. 5A is a side view of the distal portion of the example tether assembly of FIG. 4A-4D in conjunction with a side view of the IMD of FIG. 3, where the tether head assembly and the IMD are not connected.
Figure 5B:
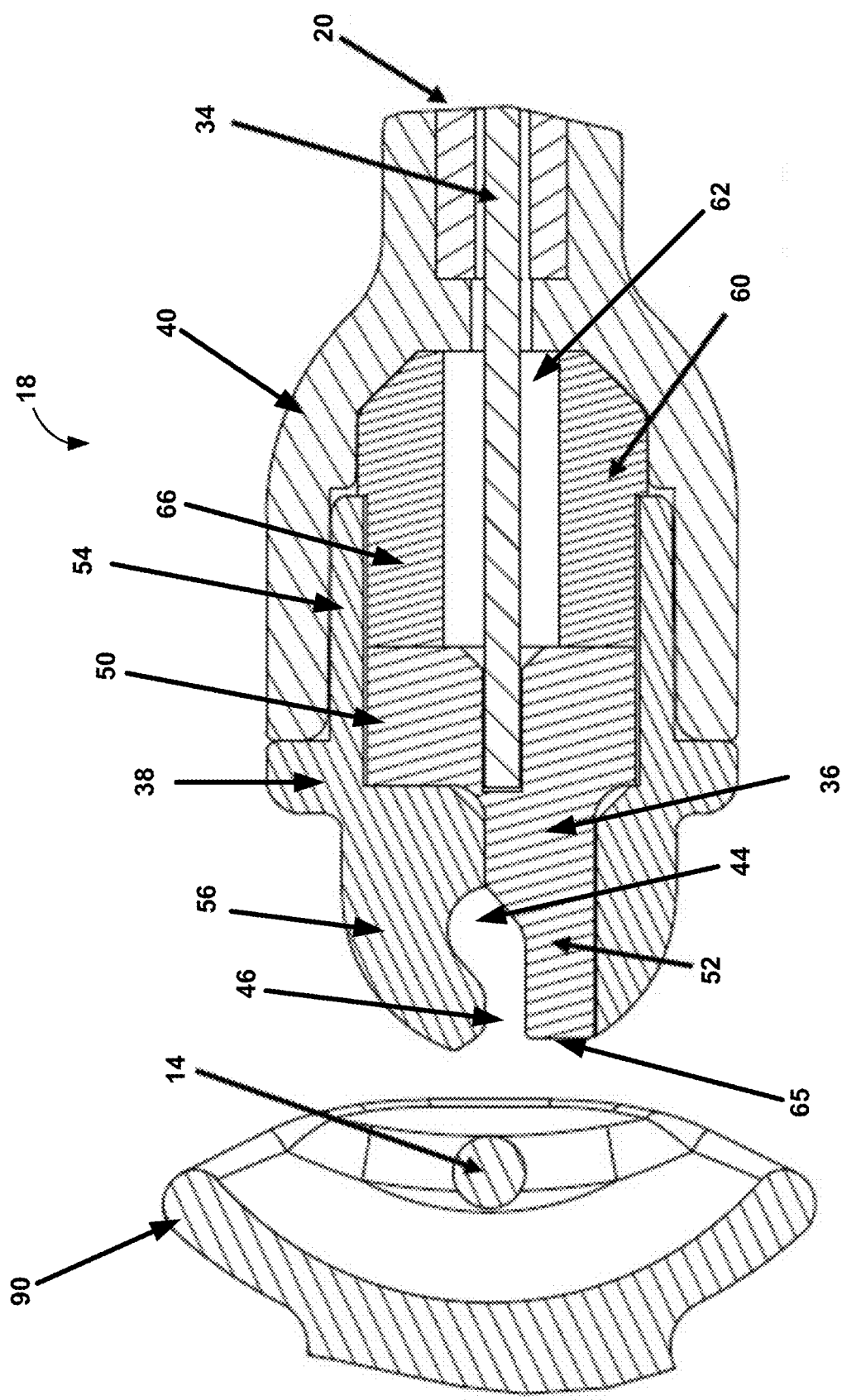
FIG. 5B is a cross-sectional view of the highlighted portion of FIG. 5A including the tether head assembly and a proximal portion of the IMD, where the cross-section is taken along line A-A of FIG. 5A in a plane parallel to a longitudinal axis of the tether head assembly a longitudinal axis of the IMD.
Figure 5C:
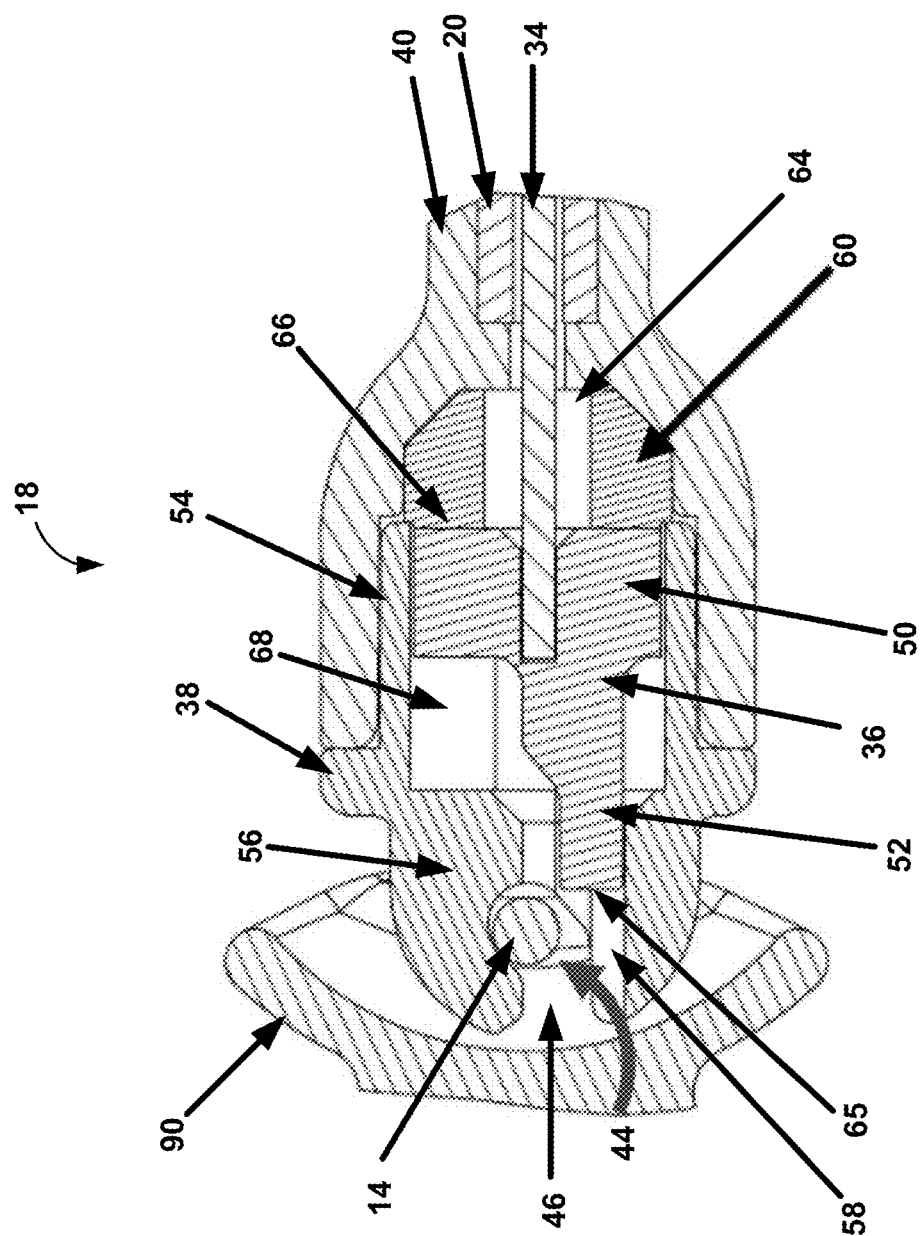
FIG. 5C is a cross-sectional view of the highlighted portion of FIG. 5A including the tether head assembly and the proximal portion of the IMD with the inner retainer in the second position and the attachment member of the IMD within the receptacle defined by the outer retainer.
Figure 5D:
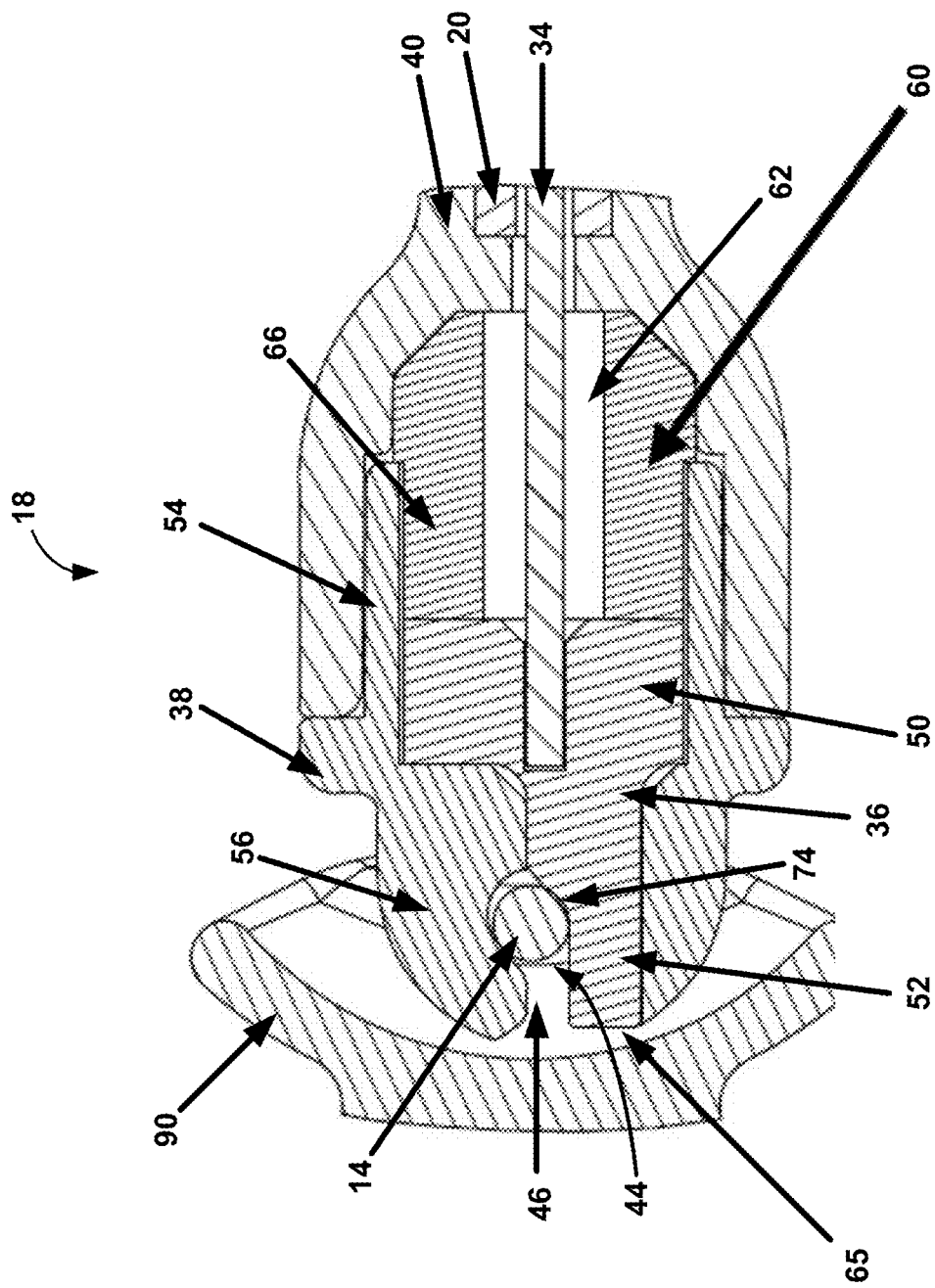
FIG. 5D is a cross-sectional view of the highlighted portion of FIG. 5A including the tether head assembly and the proximal portion of the IMD with the attachment member of the IMD held within the receptacle defined by the outer retainer by inner retainer in the first position.

FIG. 5A is a side view of the distal portion of tether assembly 12, including tether head assembly 18, in conjunction with a side view of IMD 10, where tether head assembly 18 and IMD 10 are not connected. FIG. 5B is a cross-sectional view of the portion of tether head assembly 18 and of the proximal portion of IMD 10 highlighted in FIG. 5A, where the cross-section is taken along line A-A of FIG. 5A in a plane parallel to a longitudinal axis of tether head assembly 18 and a longitudinal axis of the IMD 10. FIG. 5C is a cross-sectional view of the highlighted portion of FIG. 5A including the distal portion of tether head assembly 18 and the proximal portion of IMD 10, but with inner retainer 36 in the second position and attachment member 14 within receptacle 44 defined by the outer retainer 38. FIG. 5D is a cross-sectional view of the highlighted portion of FIG. 5A including the distal portion of tether head assembly 18 and the proximal portion of IMD 10, but with attachment member 14 held within receptacle 44 defined by outer retainer 38 by inner retainer 36 being in the first position.

FIGS. 5A and 5B illustrate IMD 10 detached from tether assembly 12, as may be the case prior to loading IMD 10 onto tether assembly 12 or after IMD 10 has been implanted at a desired tissue site. In particular, in FIGS. 5A and 5B, attachment member 14 of IMD 10 is not received within tether head assembly 18 of tether assembly 12.

FIG. 5B illustrates sheath 40 of tether head assembly 18 attached to the distal end of elongate member 20 of tether assembly 12. Pull wire 34 extends through a lumen defined by elongate member 20 and into cavity 64 (FIG. 4B) defined by sheath 40. Elastically-compressible member 60, proximal portion 50 of inner retainer 36, and proximal portion 54 of outer retainer 38 are disposed within cavity 64, with a distal portion 66 of elastically-compressible member 60 and proximal portion 50 of inner retainer 36 received within a channel 68 (FIG. 5C) defined by proximal portion 54 of outer retainer 38. Pull wire 34 extends through lumen 62 defined by elastically-compressible member 60, and is connected to inner retainer 36, e.g., fixedly received within proximal portion 50 of inner retainer 36. Various components of delivery system 12 and tether assembly 18 may be connected by any of a variety of techniques, such as welding, crimping, threading, reflowing, bonding, adhesives, or friction fits.

Distal portion 52 of inner retainer 36 extends into distal portion 56 of outer retainer 38 to contribute to the definition of receptacle 44. In the illustrated first position of inner retainer 36, distal portion 52 of inner retainer 36 also extends into passageway 46 to reduce the size of the passageway such that a thickness or depth of the passageway is smaller than a thickness of attachment member 14 of IMD 10. In the illustrated first position of inner retainer 36, distal portion 52 of inner retainer 36 may be disposed within groove 58 defined by distal portion 56 of outer retainer 38, as described herein. In the illustrated first position of inner retainer 36, elastically-compressible member 60 may be in a relaxed, or lower kinetic energy state.

As illustrated in FIG. 5B, attachment member 14 of IMD 10 may be included as part of a structure that provides a variety of features supporting a variety of functions related to delivery and retrieval of IMD 10. In the illustrated example, attachment member 14 is formed within, and joined to housing 80 of IMD 10, by a shroud structure 90. In the illustrated example, attachment member 14 comprises a pin (also referred to as a strut) that is welded or otherwise fixedly attached to shroud structure 90. Attachment member 14 provides an elongate holding surface that is spaced apart from housing proximal end 82 of housing 80 and that extends along a length substantially orthogonal to a longitudinal axis of IMD 10.

Shroud structure 90 may define a cavity with an opening and attachment member 14 may span and be exposed at the opening. Attachment member 14 may be welded at either end to opposing sides of shroud structure 90. Distal portion 56 of outer retainer 38 may be configured to enter or otherwise interact with shroud structure 90 when attachment member 14 is received within passageway 46 and receptacle 44. The configuration of shroud structure 90 and distal portion 56 of outer retainer 38 may selectively inhibit or allow relative motion of IMD 10 and tether assembly in a variety of directions. It should be understood that shroud structure 90 and attachment member 14 are provided for example only, and that a variety of other attachment members may be configured to be attached to tether assemblies as described herein.

FIG. 5C illustrates inner retainer 36 in the second position and attachment member 14 within receptacle 44 defined by the outer retainer 38. Inner retainer 36 may be moved to the second position by a proximally directed force. The proximally directed force may be provided by a pulling force from pull wire 34 or a pushing force on distal end 65 of inner retainer 36 as attachment member 14 is pushed through passageway 46 and into receptacle 44. As illustrated in FIG. 5C, movement of inner retainer 36 to the second position has compressed elastically-compressible member 60, e.g., such that distal portion 66 is no longer located within channel 68 defined by proximal portion 54 of external retainer 38.

When in this compressed state, elastically-compressible member 60 may have higher kinetic energy to be released by expanding in the direction of its longitudinal axis to the expanded or relaxed state illustrated in FIGS. 5B and 5D, thereby moving inner retainer 36 from the second position to the first position illustrated in FIGS. 5B and 5D. FIG. 5D illustrates attachment member 14 held within receptacle 44 defined by outer retainer 38 by inner retainer 36 being in the first position. Receptacle 44 is configured, e.g., sized and shaped, to retain attachment member 14 while allowing distal portion 52 of inner retainer 36 to move past the attachment member, e.g., through passageway 46. As illustrated in FIG. 5D, at least third portion 74 of distal portion 52 of inner retainer 36 may contact attachment member 14 of IMD 10 when the attachment member is positioned within receptable 44, e.g., when inner retainer 36 is in the first position. As described herein, third portion 74 may secure attachment member 14 within receptacle 44 and help ensure substantially constant physical contact between attachment member 14 and at least third portion 74 of inner retainer 36. The physical contact between attachment member 14 and inner retainer 36 enabled by third portion 74 may provide substantially constant electrical contact for conduction of electrical signals, e.g., for impedance monitoring, from IMD 10 to a proximal portion of tether assembly 12.

Figure 6D:
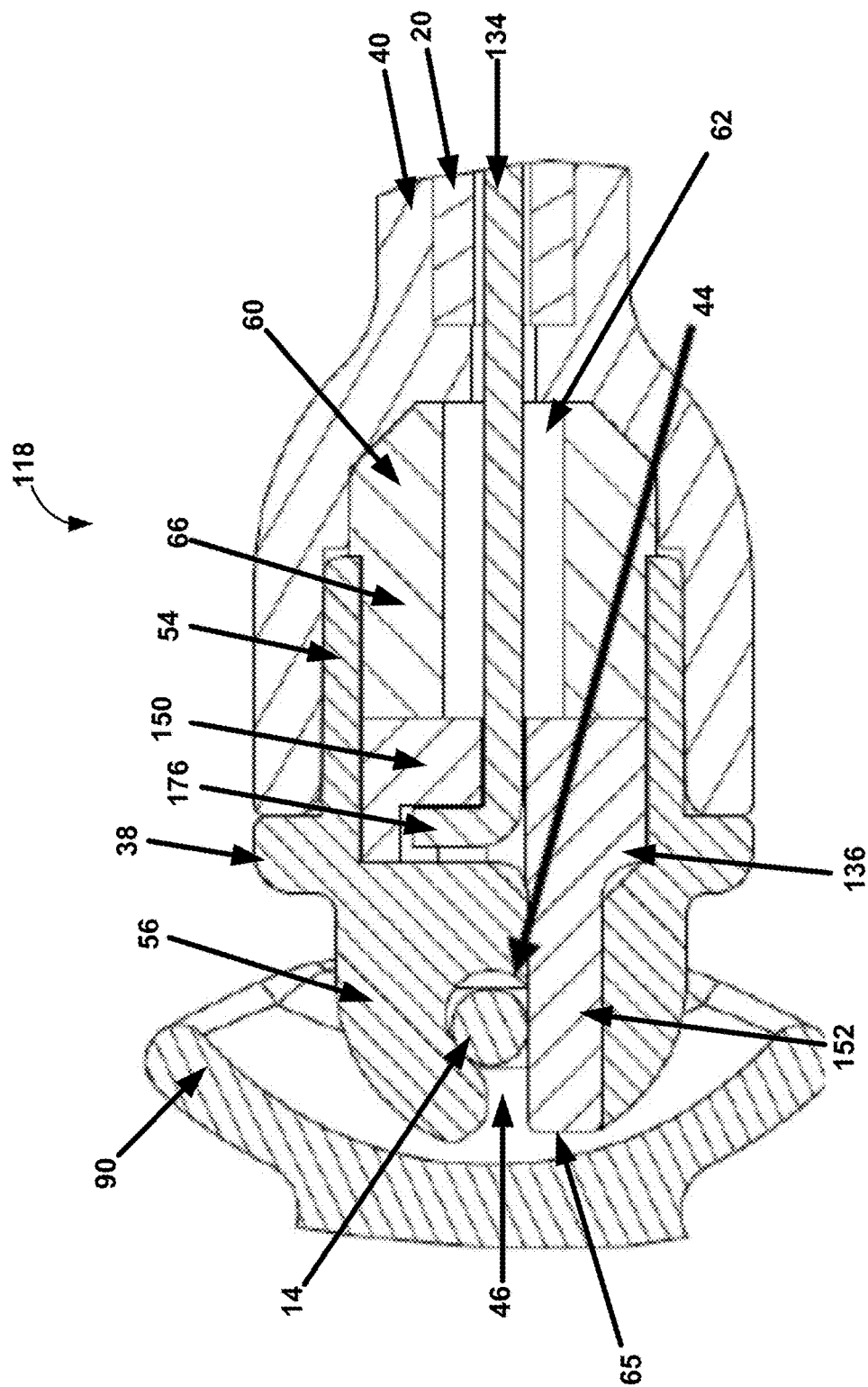
FIG. 6D is a cross-sectional view of the example tether head assembly of FIG. 6A and a proximal portion of the IMD of FIG. 3, where the cross-section is taken along a plane parallel to a longitudinal axis of the tether head assembly and a longitudinal axis of the IMD.

FIG. 6A is an exploded view of a distal portion of another example tether assembly 112 including another example tether assembly 118 and a pull wire 134, where a distal portion 152 of an inner retainer 136 of tether head assembly 118 is outlined. FIG. 6B is a plan view of the outlined portion of FIG. 6A, including distal portion 152 of inner retainer 136 in conjunction with a distal portion 176 of pull wire 134. FIG. 6C is a plan view of distal portion 152 of inner retainer 136 received within an outer retainer 38 of tether head assembly 118. FIG. 6D is a cross-sectional view of tether head assembly 118 and a proximal portion of IMD 10, where the cross-section is taken along a plane parallel to a longitudinal axis of the tether head assembly and a longitudinal axis of the IMD. Except as noted herein, tether assembly 112 and tether head assembly 118 may be substantially similar to tether assembly 12 and tether head assembly 18 described above with respect to FIGS. 4A-5D. For example, components of tether assembly 112 and tether head assembly 118 having the same reference numbers as components in tether assembly 12 and tether head assembly 18 may be configured and function as described with respect to FIGS. 4A-5D.

In the example of FIGS. 6A-6D, inner retainer 136 differs from inner retainer 36 described above with respect to FIGS. 4A-5D. Like inner retainer 36, inner retainer 136 includes a proximal portion 150 received in a channel defined by a proximal portion 54 of outer retainer 38. Inner retainer 136 also includes a distal portion 152 that is supported by groove 58 defined by However, distal portion 152 of inner retainer 136 does not include portions having different thickness, e.g., like portions 70, 72, and 74 of distal portion 52 of inner retainer 36. In some examples, distal portion 152 defines a substantially constant thickness along its length. Attachment member 14 may apply force to distal end 65 of inner retainer 136 and move inner retainer 136 to the second position as elastically-compressible member 60 is compressed, thereby allowing attachment member 14 to pass through passageway 46 and into receptacle 44. Inner retainer 136 may return to the first position, e.g., in response to longitudinal expansion of elastically-compressible member 60, to retain attachment member 14 in receptacle 44, as shown in FIG. 6D. However, distal portion 152 may not include a ramped or elevated surface to contact attachment member 14, e.g., as provided by portion 74 of distal portion 52 of inner retainer 36. distal portion 56 of outer retainer 38. Like inner retainer 36, distal portion 152 of inner retainer 136 extends into aperture 42 to reduce a size of passageway 46 when inner retainer 136 is in the first position and elastically-compressible member 60 is in its relaxed state FIGS. 6A-6D also illustrate a different coupling of pull wire 134 and inner retainer 136 then the coupling of pull wire 34 to inner retainer 36. In particular, pull wire 134 includes a bent distal portion 176. Proximal portion 150 of inner retainer 136 defines a notch or other corresponding feature (FIG. 6D) configured to receive bent distal portion 176. When pull wire 134 is actuated, distal portion 176 may bear against proximal portion 150 to move inner retainer 136 from the first position to the second position. In some examples, the coupling of pull wire 134 and inner retainer 136 illustrated in FIGS. 6A-6D may allow some relative movement between these structures, e.g., in response to bending and changes in length of pull wire 134 during an implant procedure.

Figure 7:
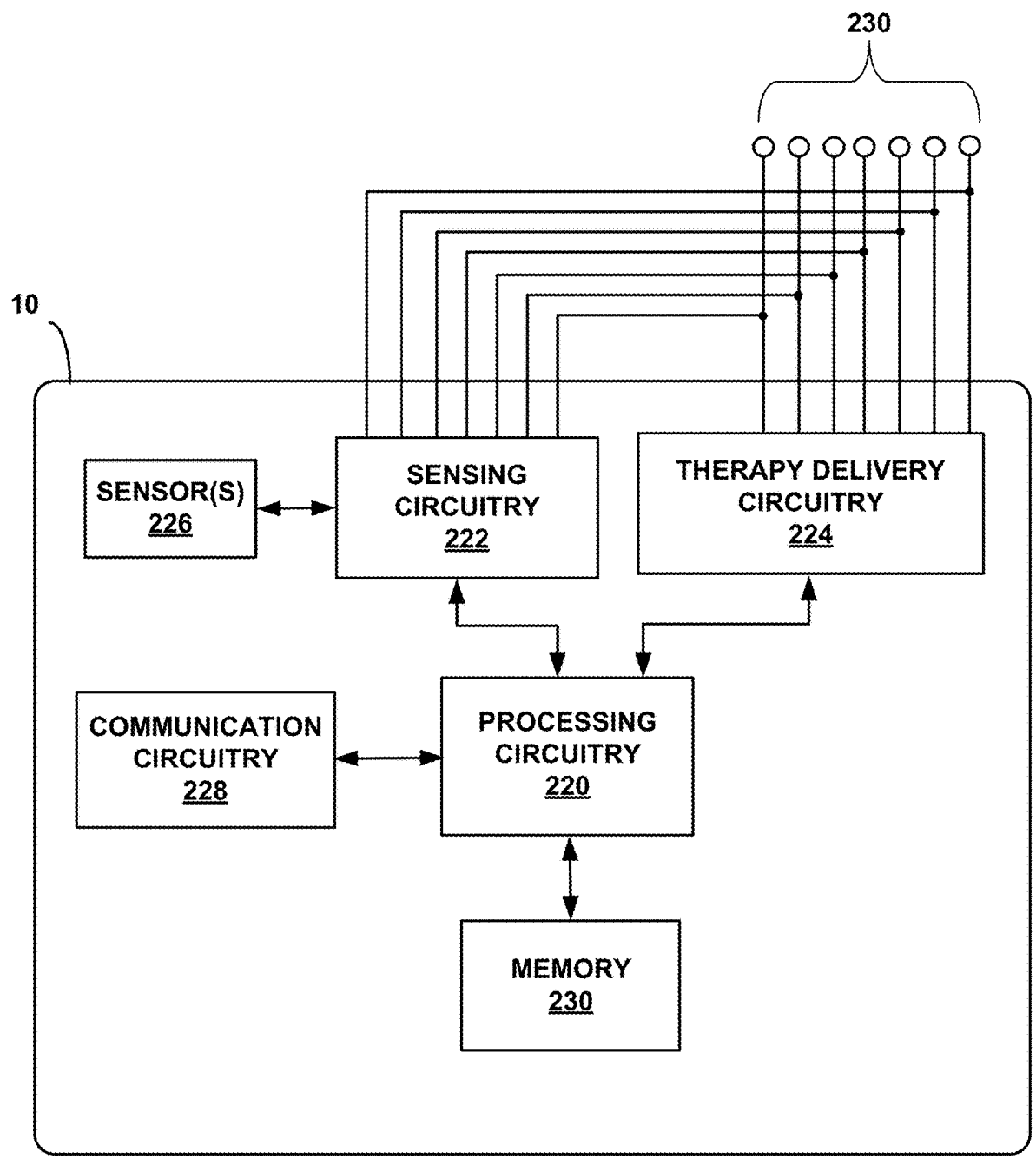
FIG. 7 is a functional block diagram illustrating an example configuration of an IMD.

FIG. 7 is a functional block diagram illustrating an example configuration of IMD 10. As shown in FIG. 7, IMD 10 includes processing circuitry 220, sensing circuitry 222, therapy delivery circuitry 224, sensors 226, communication circuitry 228, and memory 230. In some examples, memory 230 includes computer-readable instructions that, when executed by processing circuitry 220, cause IMD 10 and processing circuitry 220 to perform various functions attributed to IMD 10 and processing circuitry 220 herein. Memory 230 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processing circuitry 220 may include fixed function circuitry and/or programmable processing circuitry. Processing circuitry 220 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 220 may include multiple components, such as any combination of one or more microprocessors, one or more controllers, one or more DSPs, one or more ASICs, or one or more FPGAs, as well as other discrete or integrated logic circuitry. The functions attributed to processing circuitry 220 herein may be embodied as software, firmware, hardware or any combination thereof.

In some examples, processing circuitry 220 may receive (e.g., from an external device), via communication circuitry 228, a respective value for each of a plurality of cardiac sensing parameters, cardiac therapy parameters (e.g., cardiac pacing parameters), and/or electrode vectors. Processing circuitry 220 may store such parameters and/or electrode vectors in memory 130.

Therapy delivery circuitry 224 and sensing circuitry 222 are electrically coupled to electrodes 232, which may correspond to electrodes 86 and 88 (FIGS. 3 and 5A). Processing circuitry 220 is configured to control therapy delivery circuitry 224 to generate and deliver electrical therapy to heart 2 via electrodes 132. Electrical therapy may include, for example, pacing pulses, or any other suitable electrical stimulation. Processing circuitry 220 may control therapy delivery circuitry 224 to deliver electrical stimulation therapy via electrodes 232 according to one or more therapy parameter values, which may be stored in memory 230. Therapy delivery circuitry 224 may include capacitors, current sources, and/or regulators, in some examples.

In addition, processing circuitry 220 is configured to control sensing circuitry 222 to monitor signals from electrodes 232 in order to monitor electrical activity of heart 2. Sensing circuitry 222 may include circuits that acquire electrical signals, such as filters, amplifiers, and analog-to-digital circuitry. Electrical signals acquired by sensing circuitry 222 may include intrinsic and/or paced cardiac electrical activity, such as atrial depolarizations and/or ventricular depolarizations. Sensing circuitry 222 may filter, amplify, and digitize the acquired electrical signals to generate raw digital data. Processing circuitry 220 may receive the digitized data generated by sensing circuitry 222. In some examples, processing circuitry 120 may perform various digital signal processing operations on the raw data, such as digital filtering. In some examples, in addition to sensing circuitry 222, IMD 10 optionally may include sensors 226, which may one or more pressure sensors and/or one or more accelerometers, as examples. Communication circuitry 228 may include any suitable hardware (e.g., an antenna), firmware, software, or any combination thereof for communicating with another device, e.g., external to the patient.

Figure 8:
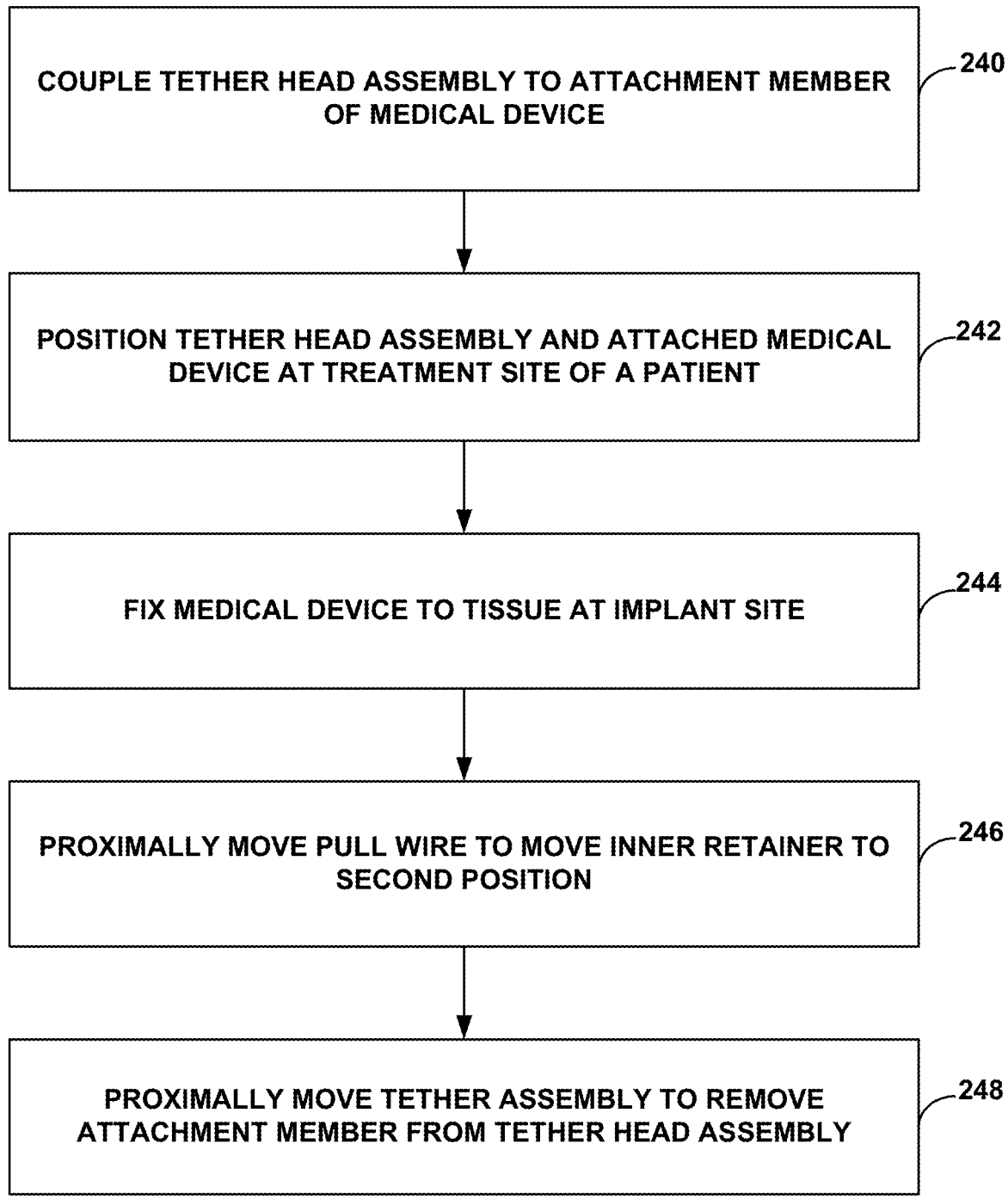
FIG. 8 is a flow diagram illustrating an example technique for using the example tether assemblies of FIGS. 4A-6D.

FIG. 8 is a flow diagram illustrating an example technique for using tether assembly 12 of FIGS. 4A-5D and tether assembly 112 of FIGS. 6A-6D. Although the example technique of FIG. 8 is described in the context of tether assembly 12 and tether head assembly 18 of FIGS. 4A-5D, the example technique should not be understood to be so limited, but instead may be applied to a method of using tether assembly 112 and tether head assembly 118 of FIGS. 6A-6D or any other tether assembly configured according to the techniques of this disclosure.

The example technique of FIG. 8 includes coupling tether head assembly 18 of tether assembly 12 to attachment member 14 of IMD 10 (240). For example, a clinician may hold tether head assembly 18 in one hand and press attachment member 14 into passageway 46 defined by outer member 38, e.g., against distal end 65 of inner retainer 36, thereby moving inner retainer 36 to the second position as attachment member 14 moves through passageway 46 to receptacle 44 and as elastically-compressible member 60 is compressed. The clinician then may release his or her hold on IMD 10 once attachment member 14 is received within receptacle 44 to allow inner retainer 36 to return to the first position via the biasing of inner retainer 36 to the first position provided by elastically-compressible member 60.

The clinician then may position IMD 10 attached to tether head assembly 18 at a treatment site of a patient (e.g., a treatment site within heart 1) with attachment member 14 received within receptacle 44 (242). In some examples, IMD 10 and tether assembly 12 may be carried within a delivery catheter 9 as it is advanced to the treatment site, e.g., as described above with respect to FIGS. 2 and 3. In some examples, the clinician may determine whether IMD 10 is properly positioned relative to heart 1 based on an impedance signal sensed via an electrical path including IMD 10, attachment member 14, and one or more components of tether member 12 (e.g., inner retainer 36 and/or or one or more other components of tether head assembly 18). The clinician then may advance fixation members 16 into the tissue of heart 1 to fix IMD 10 at the implant site (244).

Once satisfied with the positioning and fixation of IMD 10 to tissue of heart 1, the clinician may separate attachment member 14 of IMD 10 from tether head assembly 18. For example, the clinician may proximally move pull wire 34, such as by applying force to an actuator of a tether handle assembly attached at a proximal end of pull wire 34, to move inner retainer 36 from the first position to the second position (246). With inner retainer 36 in the second position, the clinician may proximally move tether assembly 12 to remove attachment member 14 from tether head assembly 18 (248). For example, proximal movement of tether assembly 12 when inner retainer 36 is in the second position may enable attachment member 14 to pass from receptacle 44, through passageway 46, and out from distal end 48 of outer retainer 38.

Figure 9A:
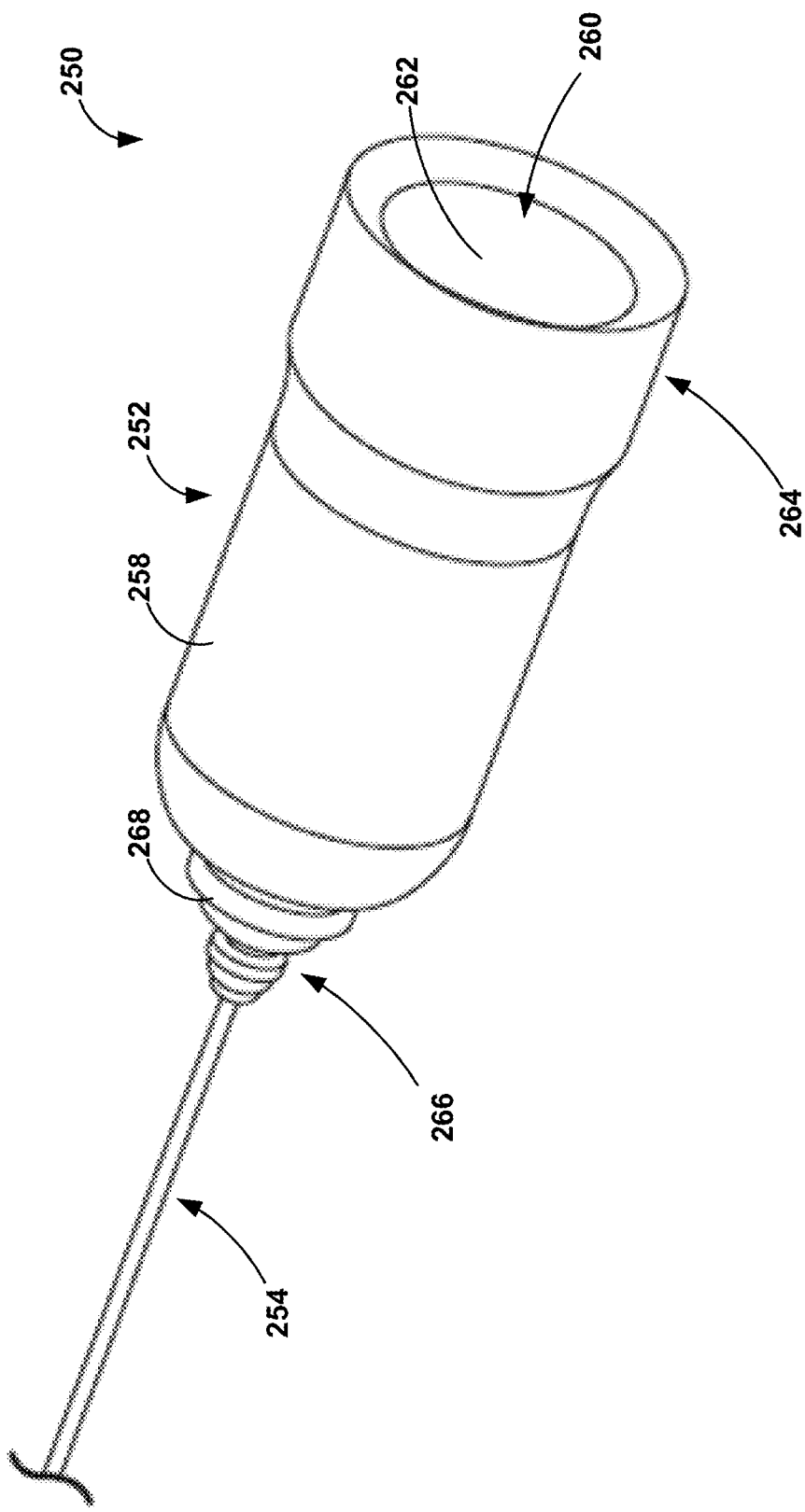
FIG. 9A is a plan view of an example tether handle assembly of a proximal portion of another example tether assembly.

FIGS. 9A-11J illustrate a proximal portion of another example tether assembly 250 including a tether handle assembly 252. FIG. 9A is a plan view of tether handle assembly 252, and FIG. 9B is an exploded plan view of tether handle assembly 252. As illustrated in FIG. 9A, tether handle assembly 252 may be coupled to a proximal end of an elongate member 254 of tether assembly 250, which may correspond with and be substantially similar to elongate member 20 illustrated in FIGS. 3-6D. In some examples, tether handle assembly 252 may be a handle assembly of a tether assembly including either of tether head assemblies 18 or 118. In some such examples, tether head assembly 18 or 118 may be coupled to elongate body 254 in a manner similar to a manner in which tether head assembly 18 or 118 may be coupled to elongate body 20 as described above. The tether head assemblies and tether handle assemblies described herein may be used in any suitable combination with one another as part of a tether assembly. Thus, example combinations of the tether head assemblies and tether handle assemblies described are exemplary and should not be understood to be limiting.

Tether handle assembly 252 includes a housing 258. A pull wire (not shown) may extend through elongate member 254, and may include a proximal end received within housing 258 of tether handle assembly 252. Tether handle assembly 252 further may include a button 260 defining a proximal surface 262. Button 260 may be configured to cause a proximal movement of the pull wire when a distally-directed force is applied to proximal surface 262 of button 260. Proximal movement of the pull wire may enable movement of an inner retainer 36 or 136 from a first position to a second position, e.g., for removal of attachment member 14 of IMD 10 from a tether head assembly 18 or 118, as described herein.

Housing 258 of tether handle assembly 252 may include a shroud 264 that extends proximally of proximal surface 262 of button 260 such that proximal surface 262 is recessed within housing 258. Shroud 264 thus may help reduce a possibility of accidental application of a distally-directed force to proximal surface 262, which may help reduce a possibility of accidental deployment of IMD 10 during a procedure for delivering IMD 10.

Tether handle assembly 252 further may include a strain relief member 266 attached to housing 258 at a distal end 268 defined by housing 258. The pull wire of tether assembly 250 may extend through elongate member 254 and be received within strain relief member 266. In addition to providing strain relief for elongate member 254 and a pull wire where the pull wire enters distal end 268 of housing 258, strain relief member 266 may help enable sensing of an impedance signal or enable electrical testing of IMD 10 during a procedure to deliver IMD 10 at a treatment site.

In some examples, strain relief member 266 may be electrically conductive, and electrically coupled to a conductive element of elongate body 254. In such examples, strain relief member 266 may enable sensing of an impedance signal or other electrical signal via an electrical path including IMD 10, attachment member 14, inner retainer 36 or 136, other conductive components of tether head assembly 18 or 118, elongate member 254, and strain relief member 266. For example, a clinician may couple an electrically conductive clip or similar connector from a device external to the patient during an implant procedure to strain relief member 266 to effectively electrically couple the external device to housing 80 of IMD 10. A return electrode may be attached to patient and coupled to the external device to provide the return path.

As discussed above with respect to FIG. 3, a clinician may determine whether cup 8 and/or IMD 10 is properly positioned relative to tissue 15 of heart 1, and/or whether IMD 10 is properly fixed to tissue by fixation members 16, based on an impedance signal sensed via such an electrical path. In this manner, strain relief member 266 may help enable a clinician to determine whether IMD 10 is properly placed at a treatment site.

Figure 9B:
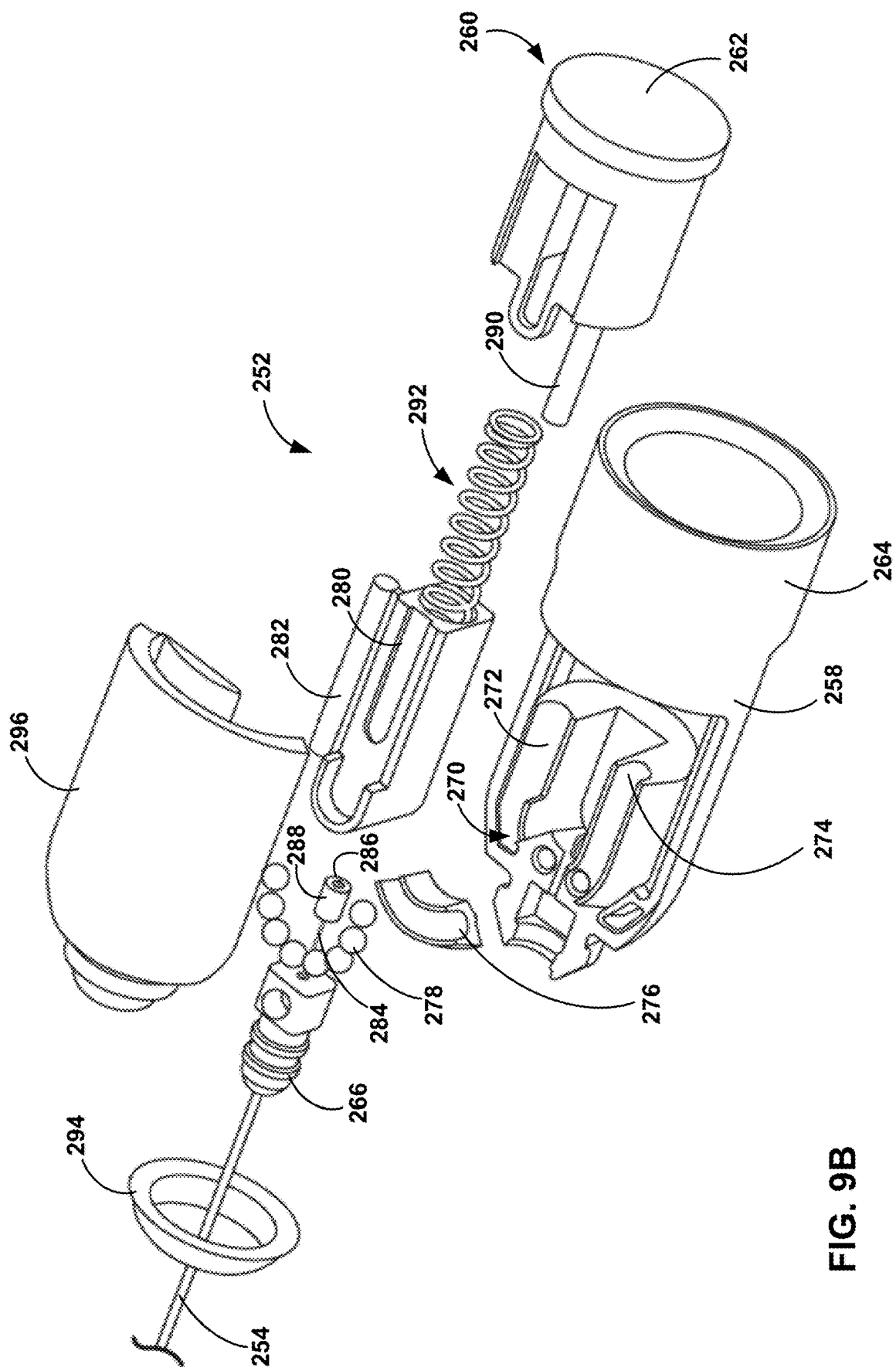
FIG. 9B is an exploded plan view of the tether handle assembly of FIG. 9A.

As illustrated in FIG. 9B, the interior of housing 258 may define at least a portion of a curved channel 270 that defines a first end 272 and a second end 274. In the illustrated example, an intermediate portion 276 of curved channel 270 between first end 272 and second end 274 may be separately formed and positioned within housing 258 during assembly of handle assembly 252, e.g., for each of manufacturing of curved channel 270. Tether handle assembly 252 further may include a force transmitter 278 received within curved channel 270. In the illustrated example, force transmitter 278 includes a plurality of balls (e.g., ball-bearings) or other similar objects that are movable through channel 270. However, other suitable objects configured to be received within channel 270 and movable therethrough may be used instead of or in addition to the plurality of balls.

Tether handle assembly 252 further may include a slidable member 280 received within housing 258 such that a channel portion 282 of slidable member 280 is received within channel 270 at first end 272 of channel 270. As illustrated in FIG. 9B, a proximal end 286 of pull wire 284 may extend from elongate member 254, through strain relief member 266, and be received within housing 258. Proximal end 286 of pull wire 284 is attached to slidable member 280. In the illustrated example, proximal end 286 of pull wire 284 is received within an anchor member 288, which may enable slidable member 280 to retain proximal end 286 of pull wire 284, thereby attaching proximal end 286 of pull wire 284 to slidable member 280.

Button 260 may include an elongate distal portion 290 received within channel 270 at second end 274. Distal portion 290 of button 260 may be configured to move force transmitter 278 within channel 270 toward first end 272 and into contact with channel portion 282 of slidable member 280. For example, when button 260 is moved from a first position to a second position in response to application of a distally-directed force to proximal surface 262 of button 260 (e.g., by a clinician pressing the button), distal portion 290 of button 260 may contact force transmitter 278 and move the force transmitter through channel 270 towards first end 272. Since force transmitter 278 is in contact with portion 282 of slidable member 280 received within channel 270, force transmitter 278 applies a proximally-directed force to channel portion 282, and thus to slidable member 280. This proximally-directed force causes slidable member 278 and pull wire 284 to move proximally. In this manner, channel 270 and force transmitter 278 may be configured to translate a distally-directed force applied to proximal surface 262 of button 260 to a proximally-directed force applied to slidable member 280 and pull wire 284. In some examples, a clinician may find applying a distally-directed force (i.e., a pushing force) to button 260 to release IMD 10 to be intuitive and/or otherwise easier to use than some other handle assembly configurations.

In some examples, tether handle assembly 252 may further include an elastically-compressible member 292, e.g., spring, positioned within housing 258 proximal to slidable member 280, which in some examples may help control movement of slidable member 280. When handle assembly 252 is in an assembled configuration, button 260 may surround at least a proximal portion of elastically-compressible member 292. Proximal movement of slidable member 280 may axially compresses elastically-compressible member 292 relative to its longitudinal axis. In some examples, elastically-compressible member 292 may help control proximal movement of slidable member 280 as slidable member 280 is moved proximally within housing 258. Additionally, or alternatively, elastically-compressible member 292 may be configured to bias slidable member 280 and/or button 260 to respective first positions thereof, e.g., their positions when button 260 is not pushed distally inward relative to housing 258, as illustrated and described with respect to FIGS. 10A-10D. Thus, when a physician releases button 260, pull wire 284 may be moved distally by elastically-compressible member 292 to aid in returning a tether head assembly 18 or 118 to a closed configuration, e.g., returning an inner retainer 36 or 136 to the first position, in some examples. Some example tether assemblies may include both an elastically-compressible member in the handle assembly, e.g., elastically compressible member 292, and an elastically-compressible member in the head assembly, e.g., elastically compressible member 60, while other tether assemblies may include only one of the elastically-compressible members to, for example, provide the functionality of returning a tether head assembly to a closed configuration, e.g., returning an inner retainer to the first position.

In some examples, as illustrated in FIG. 9B, housing 258 may comprise a removable cover portion 296, which may facilitate manufacture of tether handle assembly 252. Tether handle assembly 252 further may include an elastically-stretchable band 294, which may be configured to be placed over a distal portions of housing 258 and cover 296 to help retain components of handle assembly 252 in the assembled configuration illustrated in FIG. 9A.

FIGS. 10A-10D are side views of tether handle assembly 252 of FIGS. 9A and 9B with a portion of housing 258 removed, illustrating movement of force transmitter 278, slidable member 280, and a pull wire 284 in response to movement of button 260 from a first position 300 (FIG. 10A) to a second position 302 (FIG. 10D). First position 300 may be a "home" or uncompressed position of button 260. Second position 302 may be a compressed or depressed position of button 260. Elastically-compressible member 292 may bias button 260 to first position 300.

As shown in FIGS. 10B-10D, as button 260 is pushed inward into shroud 264 with distal force in the direction of arrow 304, distal portion 290 of button 260 moves distally in the direction of arrow 304 within channel 270. As distal portion 290 moves distally within channel 270, distal portion 290 pushes force transmitter 278 within channel toward first end 272 (FIG. 9B). In this manner, force transmitter 278 transmits the distally-directed force from button 260 to a proximally-directed force, in the direction of arrow 306, against channel portion 282 of slidable member 280. In response to the proximally-directed force, slidable member 280 and attached pull wire 284 may move proximally, in the direction of arrow 306, which may result in opening of a tether head member 18 or 118 at a distal end of a tether assembly, as described herein.

As illustrated in FIG. 10B, housing 258 and button 260 may include features configured to interact, e.g., abut, when button 260 is in second position 302. Such features may prevent further distal movement of button 260 beyond second position 302. In the illustrated example, housing 258 defines an internal ledge 308 and button 260 includes a distal overhang 310.

As button 260 moves from first position 300 to second position 302 in distal direction 304, and slidable member 280 correspondingly moves in proximal direction 306, elastically-compressible member 292 is compressed between button 260 and slidable member 280, storing potential energy. When a physician releases button 260, elastically-compressible member 292 may expand longitudinally, releasing the stored energy, and moving button 260 and slidable member 280 in directions 306 and 304, respectively, until button 260 is once again in first position 300. As slidable member 280 moves distally in direction 304, pull wire 284 may also move distally to aid in returning a tether head assembly 18 or 118 in a closed configuration, e.g., returning an inner retainer 36 or 136 to first position, in some examples.

FIGS. 11A-11J are plan views of components of tether handle assembly 252 of tether assembly 250 of FIGS. 9A and 9B, illustrating an example technique for assembling tether handle assembly 252. As illustrated in FIG. 11A pull wire 284 extends out of a proximal end of elongate member 254, and through a strain relief member 266 at the proximal end of elongate member 254. An anchor member 288 may be formed on or attached to proximal end 286 of pull wire 284.

As illustrated in FIG. 11B, housing 258 may define a receptacle 320 configured to receive strain relief member 266, and a channel 322 configured to receive pull wire 284. Anchor member 288 may be positioned on an opposite end of channel 322 from strain relief member 266. This configuration, including the fixation of strain relief member 266 in receptacle 320 of housing 258, may provide strain relief for the connection of elongate member 254 to handle assembly 252.

FIG. 11C illustrates the insertion of intermediate portion 276 to complete curved channel 270, which also closes channel 322. FIG. 11D illustrates slidable member 280 inserted into housing 258. Slidable member 280 may define a feature (not shown) configured to receive anchor member 288, thereby coupling pull wire 284 to slidable member 280.

FIG. 11E illustrates elastically-compressible member 292 inserted into housing 258, and FIG. 11F illustrates button 260 inserted into housing 258. Slidable member 280 and button 260 may include features to hold elastically-compressible member 292 between them. FIG. 11F also illustrates distal portion 290 of button 260 inserted at second end 274 of channel 270.

FIG. 11G illustrates force transmitter 278 inserted into channel 270 between distal portion 290 of button 260 and channel portion 282 of slidable member 280. FIG. 11H illustrates removable cover 296 attached to housing 258, and FIG. 11I illustrates elastically-stretchable band 294 placed over a distal portions of housing 258 and cover 296 to help retain components of tether handle assembly 252 in the assembled configuration. FIGS. 11I and 11J also illustrate that housing 258 may define features to aid the usability of handle assembly 252, such as depression 324 and ridge 326, which may aid a physician in orienting and gripping tether handle assembly 252.

FIGS. 12A-12E are plan views of another example tether handle assembly 352. Tether handle assembly 352 may be substantially similar to tether handle assembly 252 described with reference to FIGS. 9A-11J. For example, components of tether handle assembly 352 having the same reference numbers as components tether handle assembly 252 may be configured and function as described with respect to FIGS. 9A-11J.

Figure 12A:
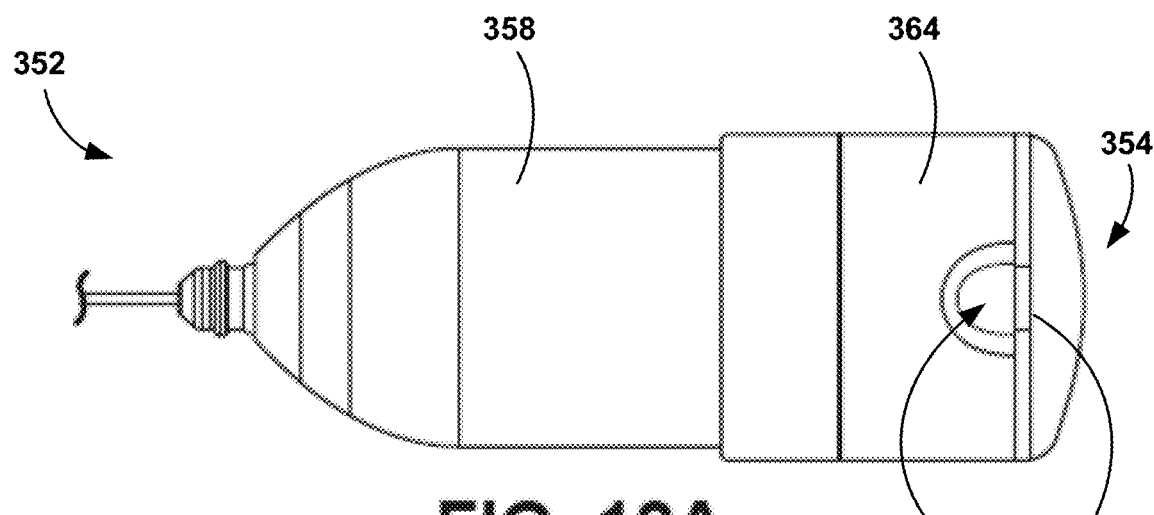
FIGS. 12A-12E are plan views of another example tether handle assembly of a tether assembly, the tether handle assembly including a cover for a button.
Figure 12B:
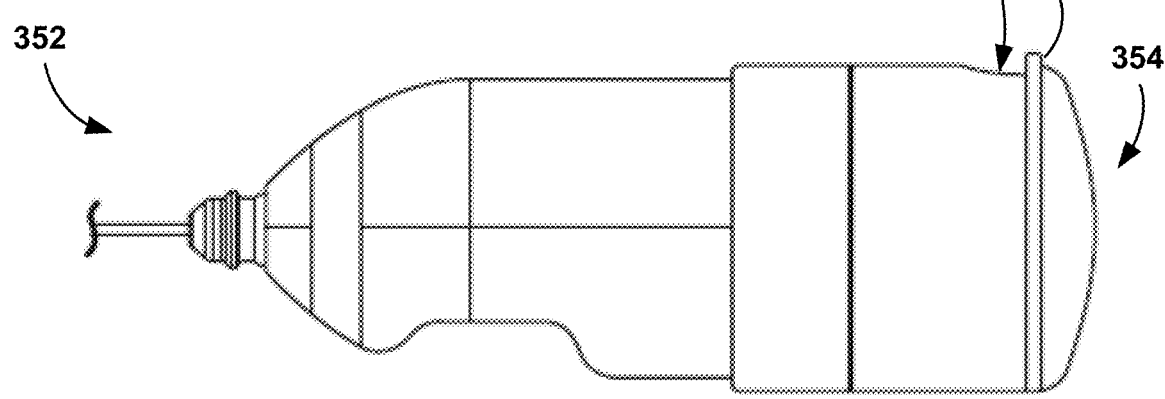
Figure 12C:
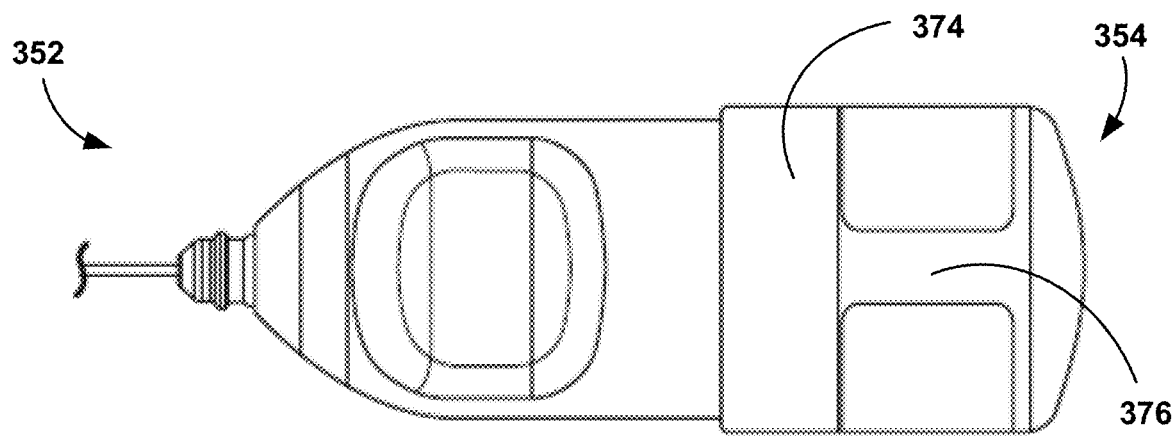
Figure 12D:
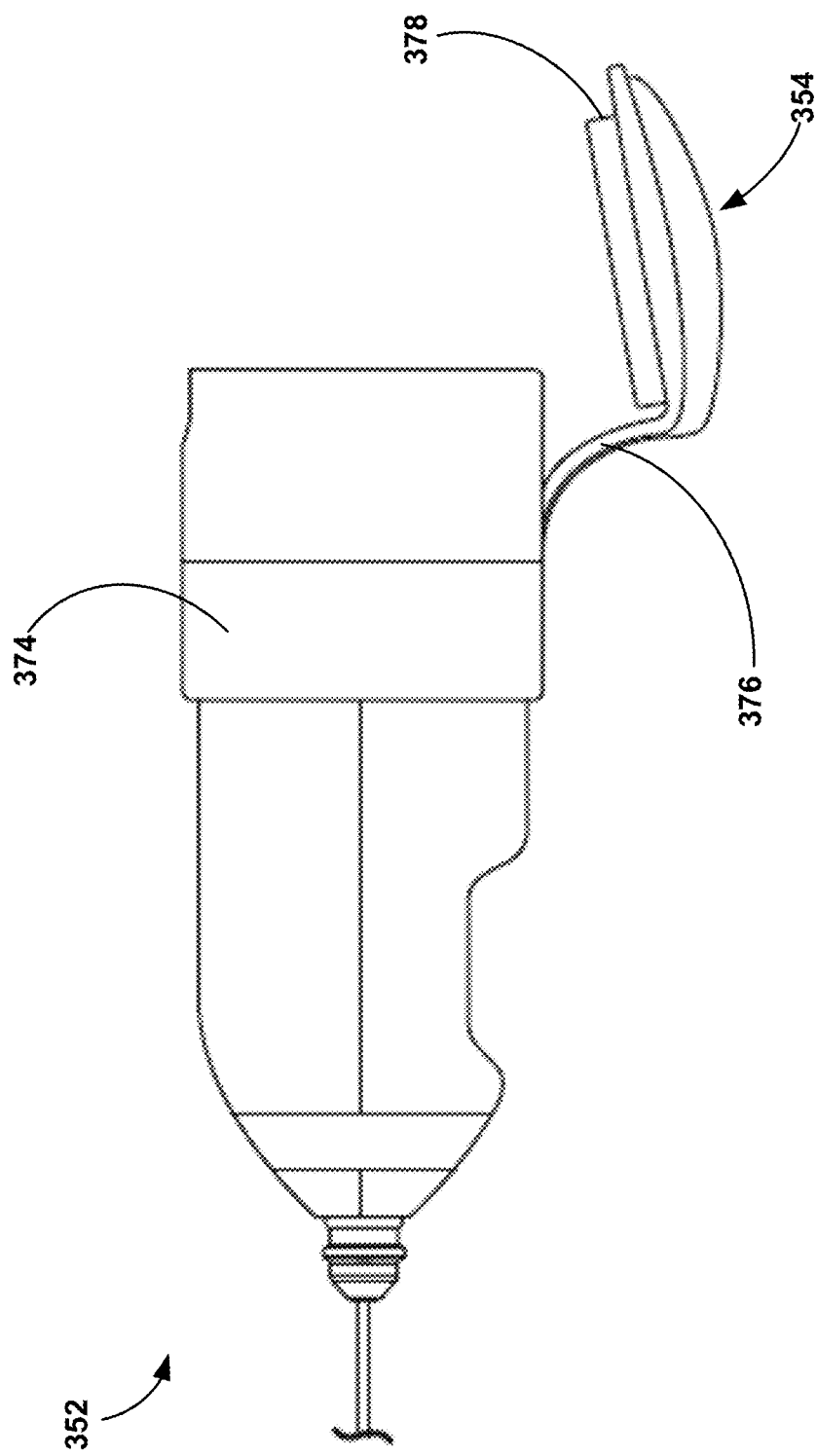
Figure 12E:
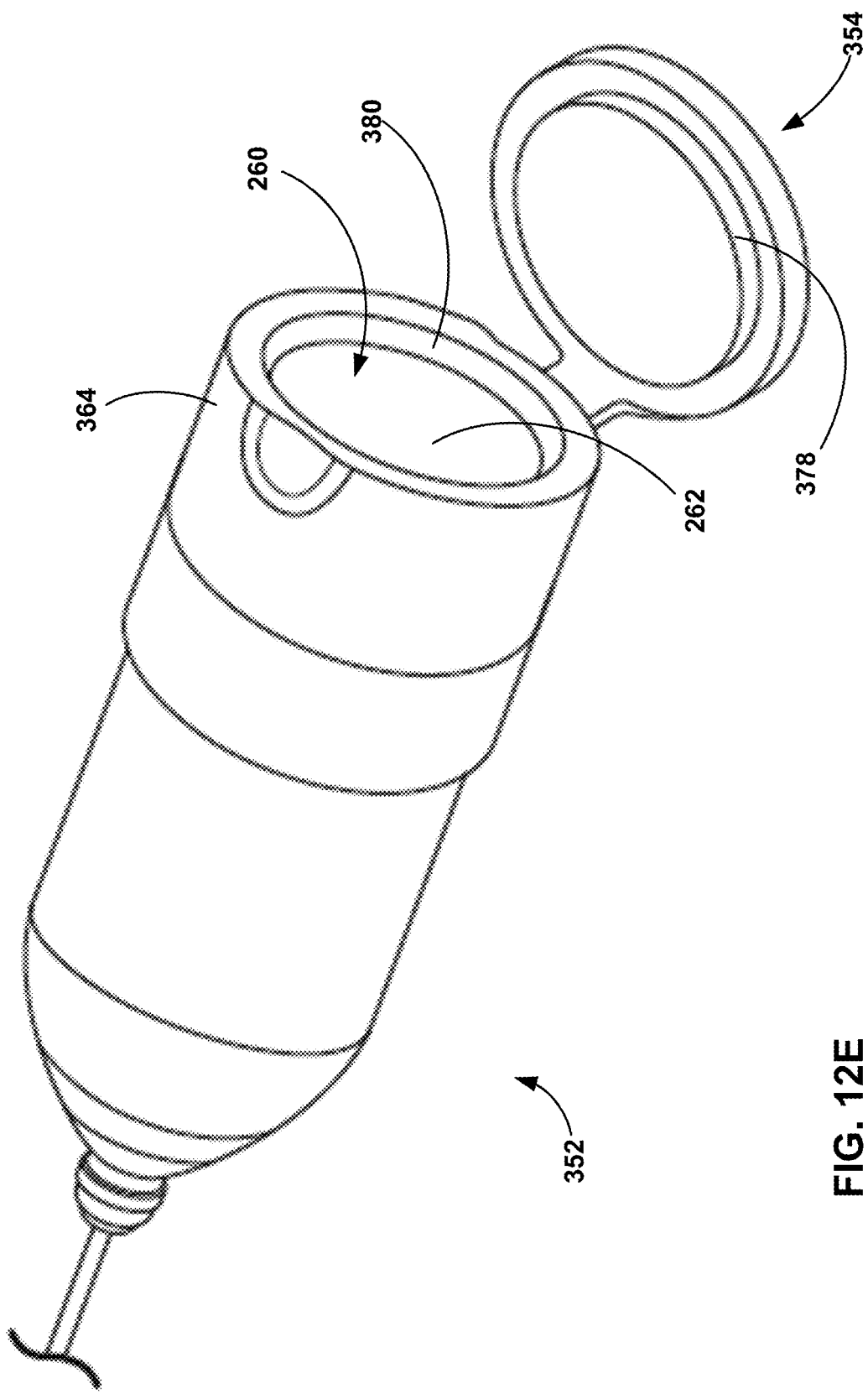

Unlike tether handle assembly 252, tether handle assembly 352 includes a cover 354 for button 260 (FIG. 12E). Housing 358 of tether handle assembly 352, e.g., shroud portion 364 of the housing, may define a depression 370 configured to allow a user's finger to access a tab 372 formed on cover 354 to move cover 354 away from button 260. Cover 354 may be included on tether handle assembly 352 to reduce the likelihood that button 260 is inadvertently pressed, and IMD 10 deployed, during an implantation procedure for IMD 10 using tether handle assembly 352.

A band 376 may connect cover 354 to a collar 374. Collar 374 and band 376 may be configured to keep cover 354 attached to tether handle assembly 352 when cover 354 is moved away from button 260, e.g., as shown in FIG. 12D. Band 376 may be configured to space cover 354 from away from a proximal opening of shroud portion 364 to facilitate ease of user access to proximal surface 262 of button 260 when cover 354 is moved, e.g., as shown in FIGS. 12D and 12E. Cover 354, collar 374, and band 376 may be formed of any material, such as a polymer, and may be formed from, e.g., molded as, a single piece of the material. Shroud portion 364 and/or other portions of housing 358 may be configured with corresponding features to receive collar 374 and band 376, e.g., to secure them to tether handle assembly 352 and provide a substantially even outer surface for tether handle assembly 352.

As illustrated in FIGS. 12D and 12E, cover 354 may include a reduced diameter plug portion 378. As illustrated in FIG. 12E, the proximal opening of shroud portion 364 may define an expanded diameter shelf 380 configured to receive plug portion 378. Plug portion 378 and shelf 380 may be configured to interact secure cover 354 within the proximal opening of shroud portion 364, e.g., via friction fit, threading, or other attachment mechanisms.

Figure 13C:
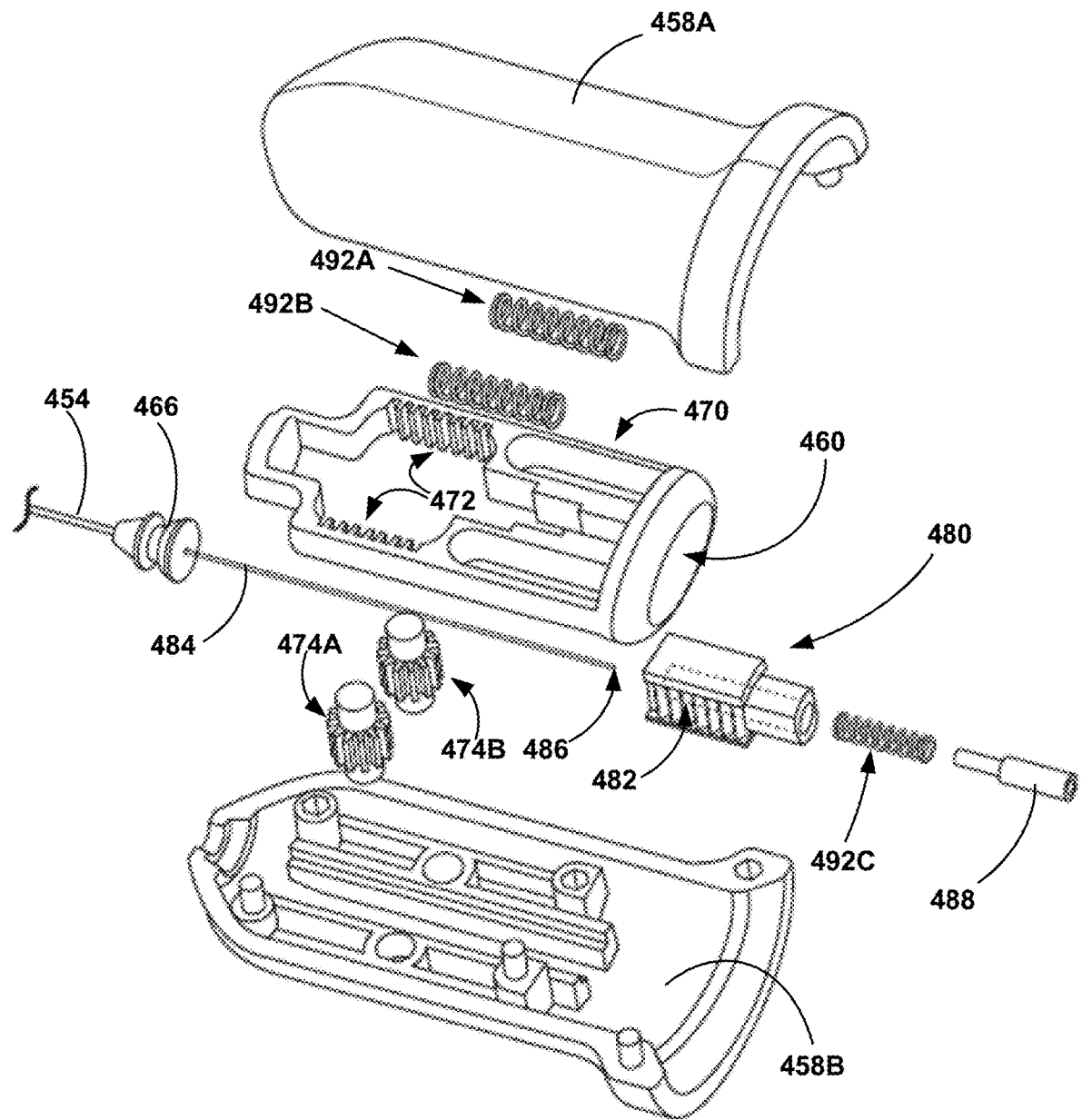
FIG. 13C is an exploded plan view of the example tether handle assembly of FIGS. 13A and 13B.
Figure 13D:
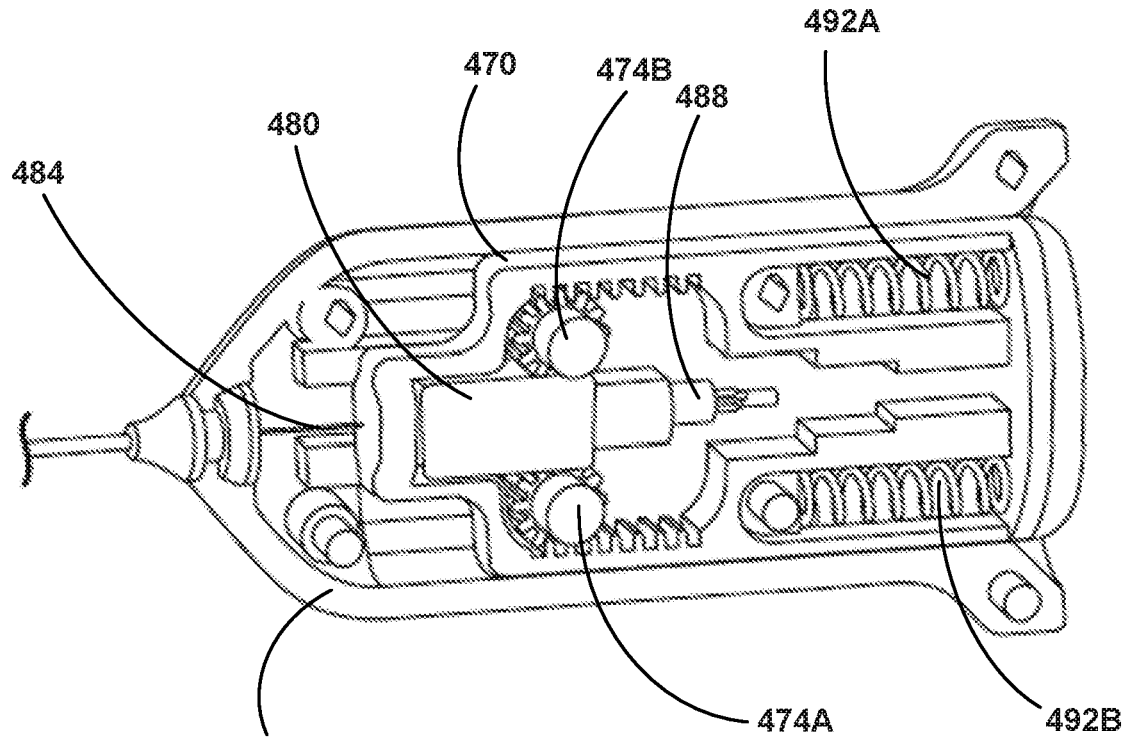
FIGS. 13D and 13E are plan views of the example tether handle assembly of FIGS. 13A-13C, with a portion of the housing removed, illustrating movement of a plurality of gears, a second slidable member, and a pull wire of the example tether handle assembly in response to movement of a first slidable member of the tether handle assembly from a first position to a second position.
Figure 13E:
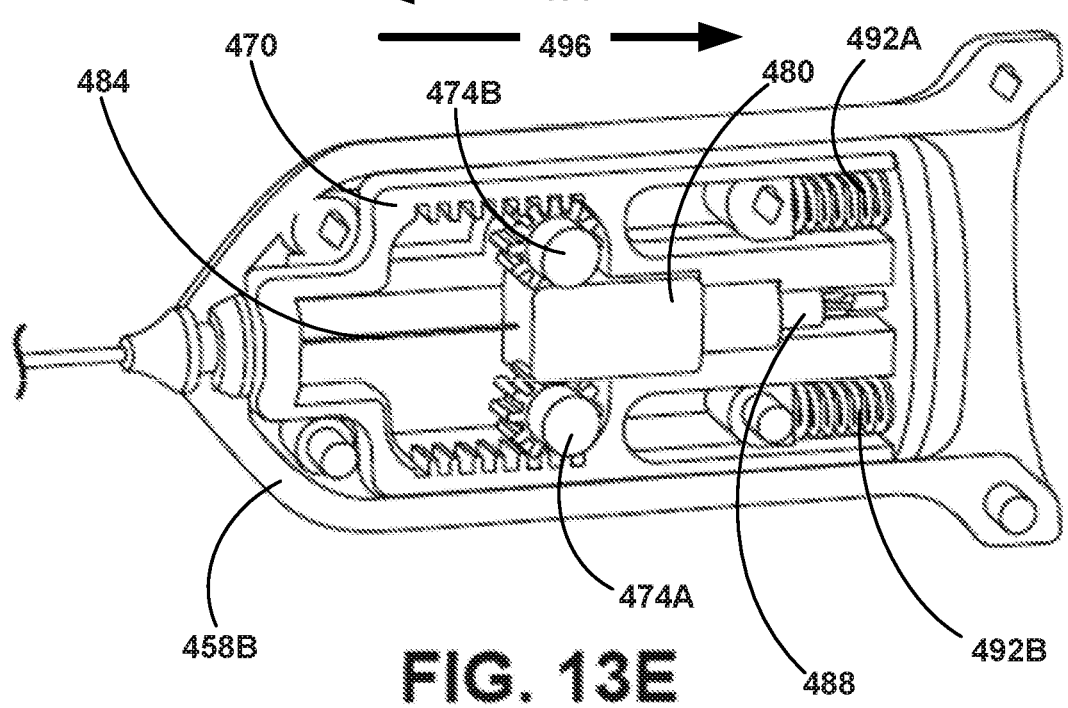

FIGS. 13A and 13B are plan views of a proximal end of another example tether assembly 412 including another example tether handle assembly 452 coupled to a proximal end of an elongate member 454. FIG. 13C is an exploded plan view of tether handle assembly 452. FIGS. 13D and 13E are plan views of tether handle assembly 452, with a portion of a housing 458 of tether handle assembly 452 removed to illustrate an example, arrangement, interaction, and movement of components of tether handle assembly 452 during use.

Elongate member 454 of tether assembly 412 may correspond with and be substantially similar to elongate member 20 illustrated in FIGS. 3-6D. In some examples, tether handle assembly 452 may be a handle assembly of tether assembly including either of tether head assemblies 18 or 118. In some such examples, tether head assembly 18 or 118 may be coupled to elongate body 454 in a manner similar to a manner in which tether head assembly 18 or 118 may be coupled to elongate body 20 as described above. The tether head assemblies and tether handle assemblies described herein may be used in any suitable combination with one another as part of a tether assembly. Thus, example combinations of the tether head assemblies and tether handle assemblies described are exemplary and should not be understood to be limiting.

In the example illustrated by FIG. 13C, housing 458 includes two housing portions 458A and 458B. Housing portions 458A and 458B may be press fit together or otherwise connected during assembly of tether handle assembly 452 to form housing 458, e.g., after the components of tether handle assembly 452 described herein are suitably arranged. Housing portions 458A and 458B may be molded components of plastic or another polymer in some examples.

A pull wire 484 (FIG. 13C) may extend through elongate member 454, and may include a proximal end 486 received within housing 458 of tether handle assembly 452. Tether handle assembly 452 further may include a button 460 defining a proximal surface 462, and configured to cause a proximal movement of pull wire 484 when a distally-directed force is applied to the proximal surface 462 of button 460. Proximal movement of the pull wire 484 may enable movement of an inner retainer 36 or 136 from a first position to a second position, e.g., for removal of attachment member 14 of IMD 10 from a tether head assembly 18 or 118, as described herein with respect to FIGS. 4A-6D.

Tether handle assembly 452 further may include a strain relief member 466 attached to housing 458 at a distal end of housing 458. Elongate member 454 may be attached to strain relief member 466 and pull wire 484 may be received within strain relief member 466. In addition to providing strain relief for elongate member 454 and pull wire 484 where the elongate member attaches to and the pull wire enters housing 458, strain relief member 466 may be electrically conductive and help enable sensing of an impedance signal or enable electrical testing of IMD 10 during a procedure to deliver IMD 10 at a treatment site, as described above with respect to strain relief member 266.

As illustrated in FIG. 13C, button 460 includes a carriage 470 within housing defining interior teeth 472 configured to interact with corresponding teeth of gears 474A and 474B (collectively, "gears 474"). Button 460 may be a machined and/or molded. Tether handle assembly 452 further includes a slidable member 480 comprising teeth 482 on opposing sides of the slidable member. Teeth 482 of slidable member 480 are configured to interact with the teeth of gears 474. Slidable member 480 defines a longitudinal lumen through which distal end 486 of pull wire 484 extends, and into which a distal portion of a sleeve 488 may be inserted. Sleeve 488 may serve to attach pull wire 484 to slidable member 480 by defining a lumen to receive proximal end 486 of pull wire 484. Proximal end 486 of pull wire 484 may be fixed to sleeve 488 by welding, crimping, capping, adhesive, and/or using an anchor member (e.g., anchor member 288 of FIG. 7B) as examples.

Tether handle assembly 452 further includes elastically-compressible members 492A, 492B, and 492C (collectively, "elastically-compressible members 492"), e.g., springs, within housing 458. The longitudinal lumen defined by slidable member 480 receives elastically-compressible member 492C, which dampens the proximal motion of pull wired 484 as button 460 is pushed distally.

FIGS. 13D and 13E are side views of tether handle assembly 452 with housing portion 458A removed, illustrating movement of carriage 470, gears 474, slidable member 480, and pull wire 484 in response to movement of button 460 from a first position (FIG. 13D) to a second position (FIG. 13E). The first position illustrated in FIG. 13D may be a "home" or uncompressed position of button 460. The second position illustrated in FIG. 13E may be a compressed or depressed position of button 460. Elastically-compressible members 492A and 492B may bias button 460 to the first position.

As shown in FIGS. 13D and 13E, as button 460 is pushed inward with distal force in the direction of arrow 494, carriage 470 moves distally in the direction of arrow 494 within housing 458. As carriage 470 moves distally, teeth 472 rotate gears 474. As gears 474 rotate against teeth 482 of slidable member 480, slidable member 480 is moved proximally in the direction of arrow 496, and pull wire 484 connected to slidable member 480 is pulled proximally in the direction of arrow 496. In this manner, gears 474 transfer the distally-directed force from button 460 to a proximally-directed force, in the direction of arrow 496, in response to which pull wire 484 may move proximally, in the direction of arrow 496, which may result in opening of a tether head member 18 or 118 at a distal end of tether assembly 412, in the manner described herein.

As button 460 moves from the first position (FIG. 13D) to the second position (FIG. 13E) in distal direction 494, elastically-compressible members 492A and 492B are compressed between button 460 and features of housing 458, storing potential energy. When a physician releases button 460, elastically-compressible members 492A and 492B may expand longitudinally, releasing the stored energy, and moving button 460 and slidable member 480 in directions 496 and 494, respectively, until button 460 is once again in the first position. As slidable member 480 moves distally in direction 494, pull wire 484 may also move distally to aid in returning a tether head assembly 18 or 118 in a closed configuration, e.g., returning an inner retainer 36 or 136 to first position, in some examples.

Figure 14:
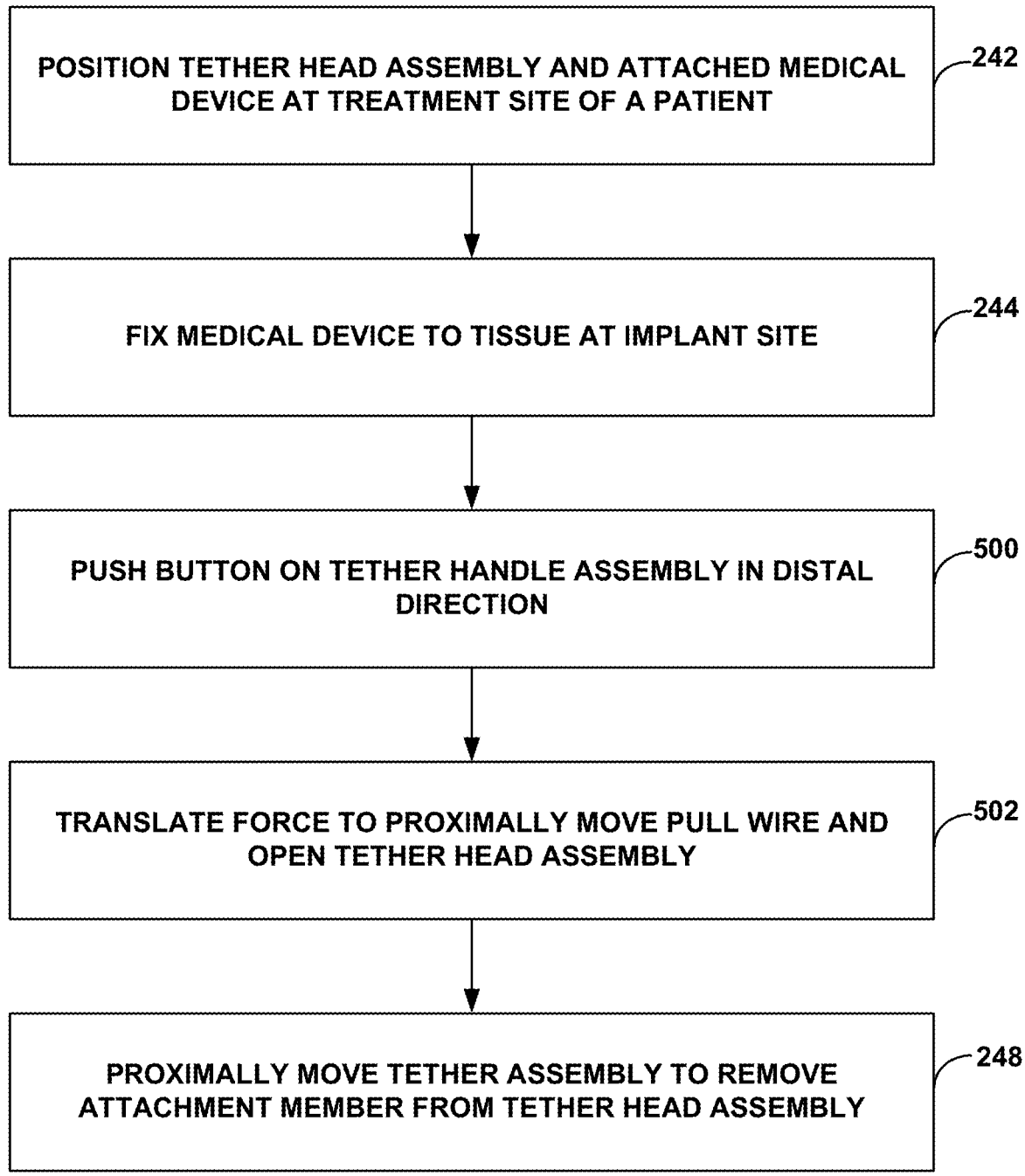
FIG. 14 is a flow diagram illustrating an example technique for using a medical device delivery system comprising a tether assembly that includes a tether handle assembly as described with respect to FIGS. 9A-13E and a tether head assembly as described with respect to FIGS. 4A-6D.

FIG. 14 is a flow diagram illustrating an example technique for using a tether assembly including a tether handle assembly as described with respect to FIGS. 9A-13E and a tether head assembly as described with respect to FIGS. 4A-6D. Although the example technique of FIG. 14 is described in the context tether head assembly 18 of FIGS. 4A-5D and tether handle assembly 252 of FIGS. 9A-11J, the example technique should not be understood to be so limited, but instead may be applied to a method of using tether head assembly 118 of FIGS. 6A-6D, handle assemblies 352 and 452 of FIGS. 12A-12E, or any other tether head assemblies or tether handle assemblies configured according to the techniques of this disclosure.

Like the example technique of FIG. 8, the example technique of FIG. 14 includes positioning IMD 10 attached to tether head assembly 18 at a treatment site of a patient (e.g., a treatment site within heart 1) with attachment member 14 received within receptacle 44 (242). In some examples, the clinician may determine whether IMD 10 is properly positioned relative to heart 1 based on an impedance signal sensed via an electrical path including IMD 10, attachment member 14, one or more components of tether head assembly 18, an elongate member, and strain relief member 266. The clinician then may advance fixation members 16 into the tissue of heart 1 to fix IMD 10 at the implant site (244).

Once satisfied with the positioning and fixation of IMD 10 to tissue of heart 1, the clinician may separate attachment member 14 of IMD 10 from tether head assembly 18. In the example of FIG. 14, the clinician pushes distally on proximal surface 262 of button 260 of tether handle assembly 252 (500). Tether handle assembly 252 translates the distal force to a proximal force, to proximally move pull wire 282 and open tether head assembly 18 (502). For example, distal portion 290 of handle 260 may move distally in channel 270 and push force transmitter 278 through channel 270 against channel portion 282 of slidable member 280, which may move slidable member 280 in a proximal direction. Pull wire 284, connected to slidable member 280, is thus moved in the proximal direction.

In other examples, distal movement of carriage 470 of button 460 rotates gears 474. The rotation of gears 474 moves slidable member 480, to which pull wire 484 is connected, proximally. In either case, with tether head assembly 18 open, the clinician may proximally move tether assembly 12 to remove attachment member 14 from tether head assembly 18 (248).

Figure 15A:
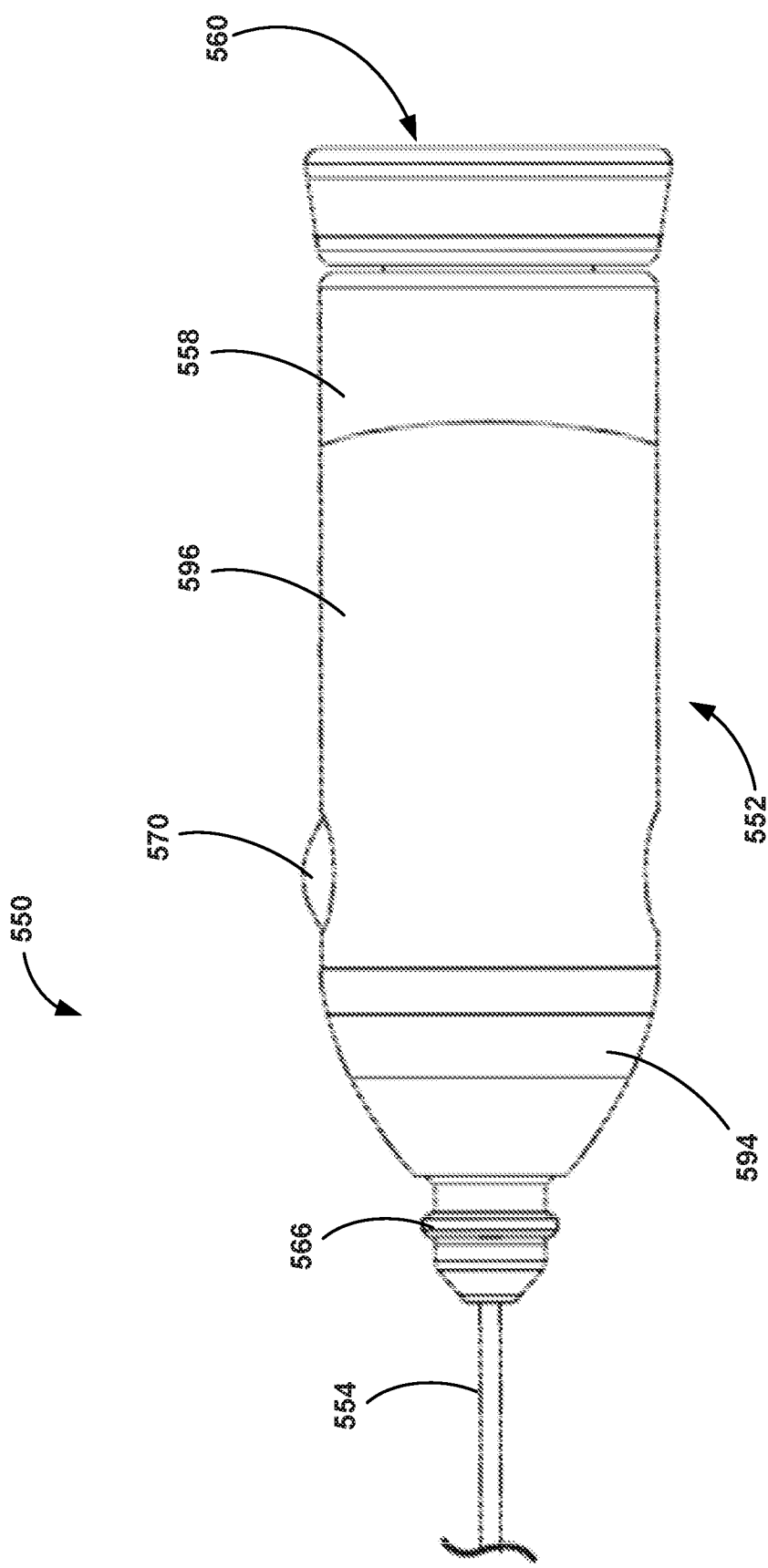
FIG. 15A is a side view of another example tether assembly including another example tether handle assembly.
Figure 15B:
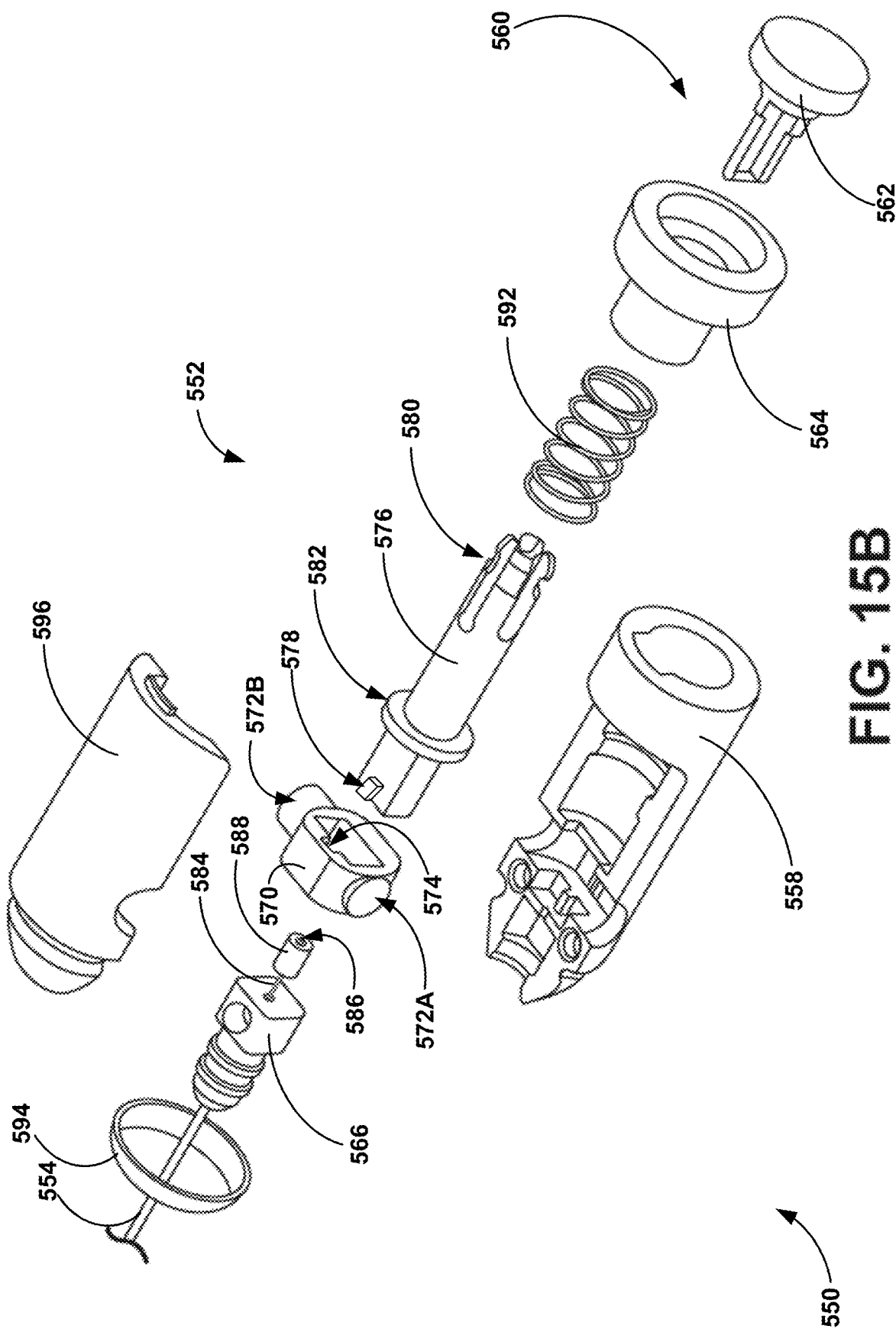
FIG. 15B is an exploded plan view of the tether handle assembly of FIG. 15A.
Figure 15C:
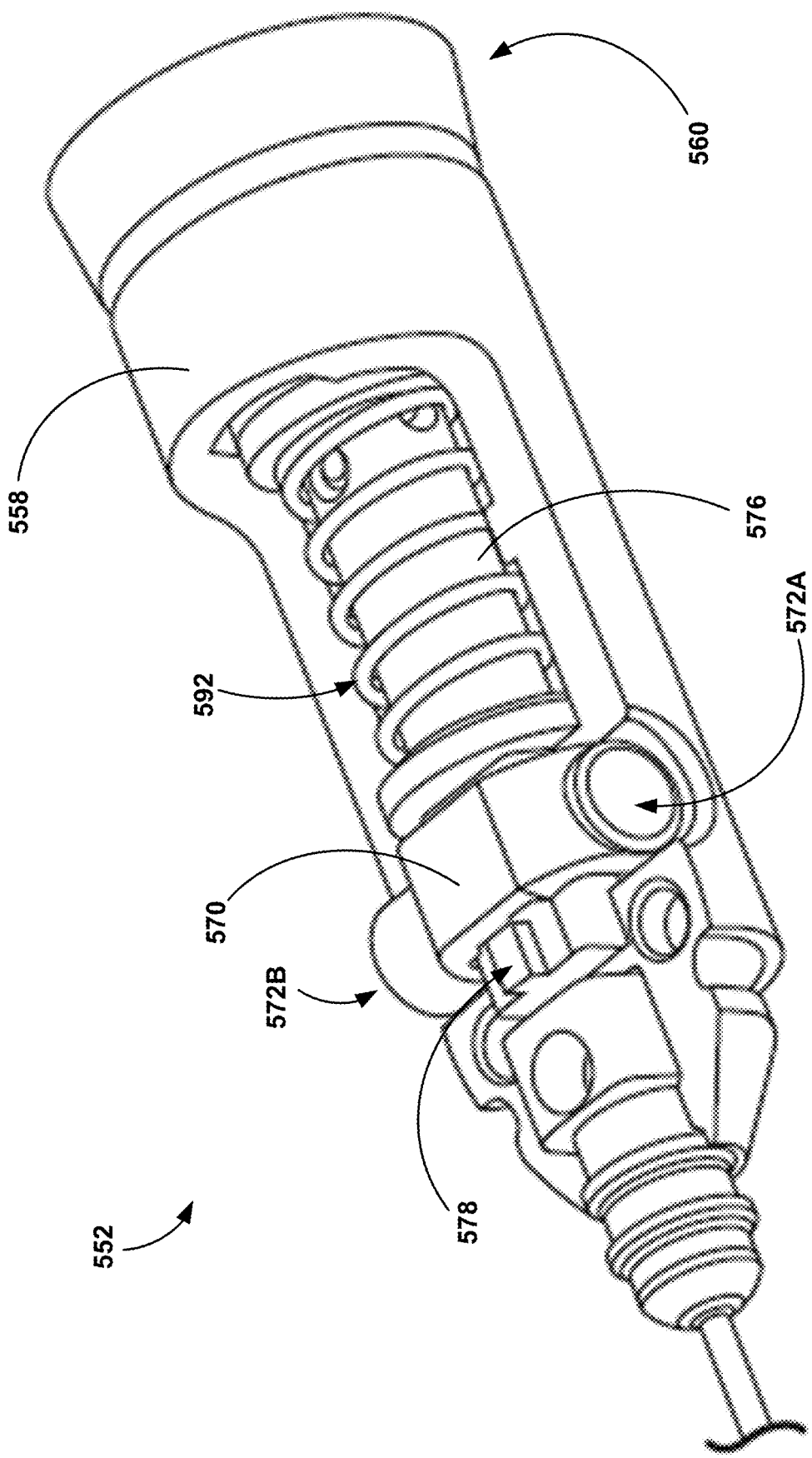
FIGS. 15C-15E are perspective views of the tether handle assembly of FIGS. 15A and 15B with a portion of the housing removed, illustrating different positions of a lock member and a plunger of the tether handle assembly.
Figure 15D:
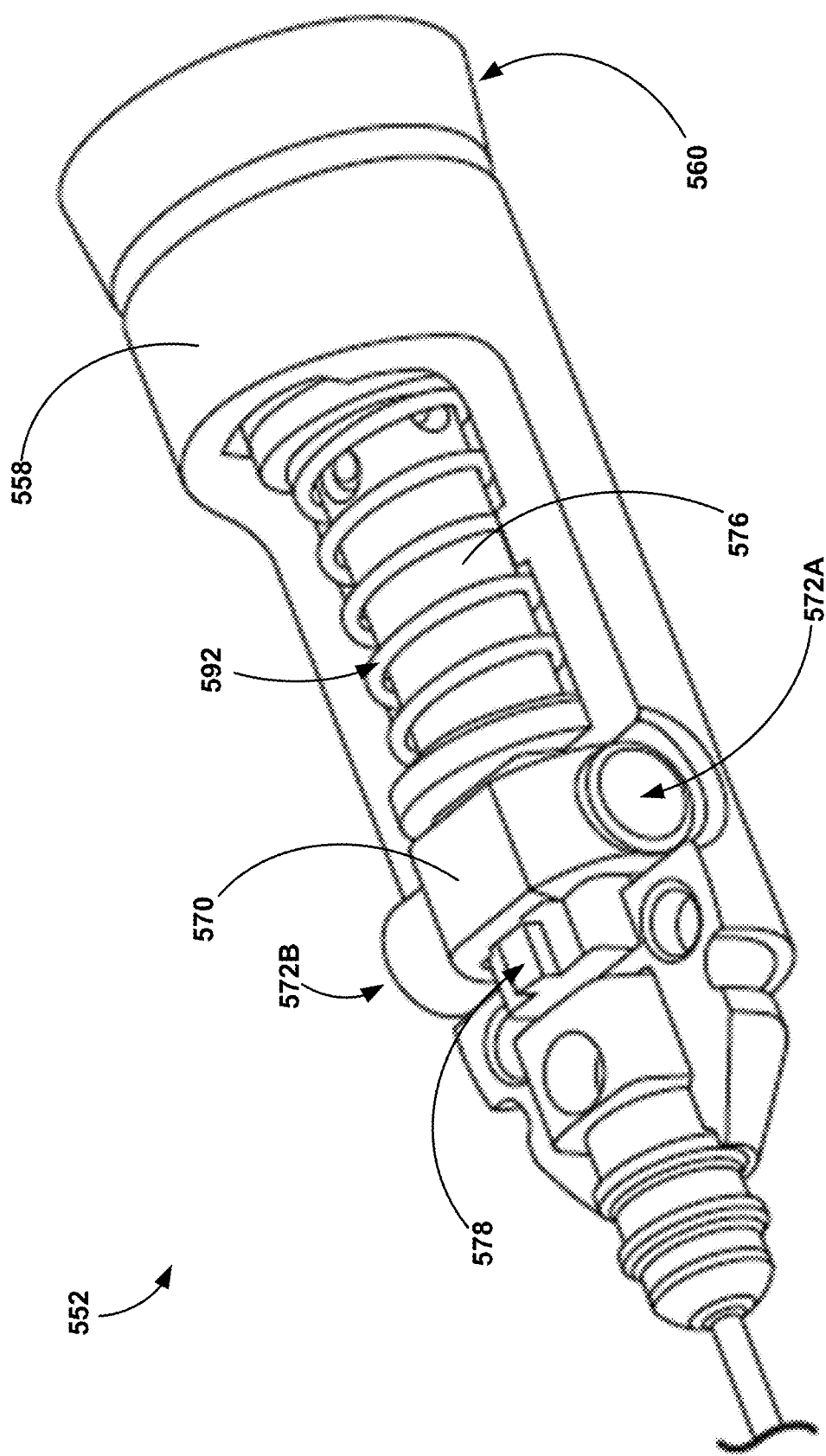
Figure 15E:
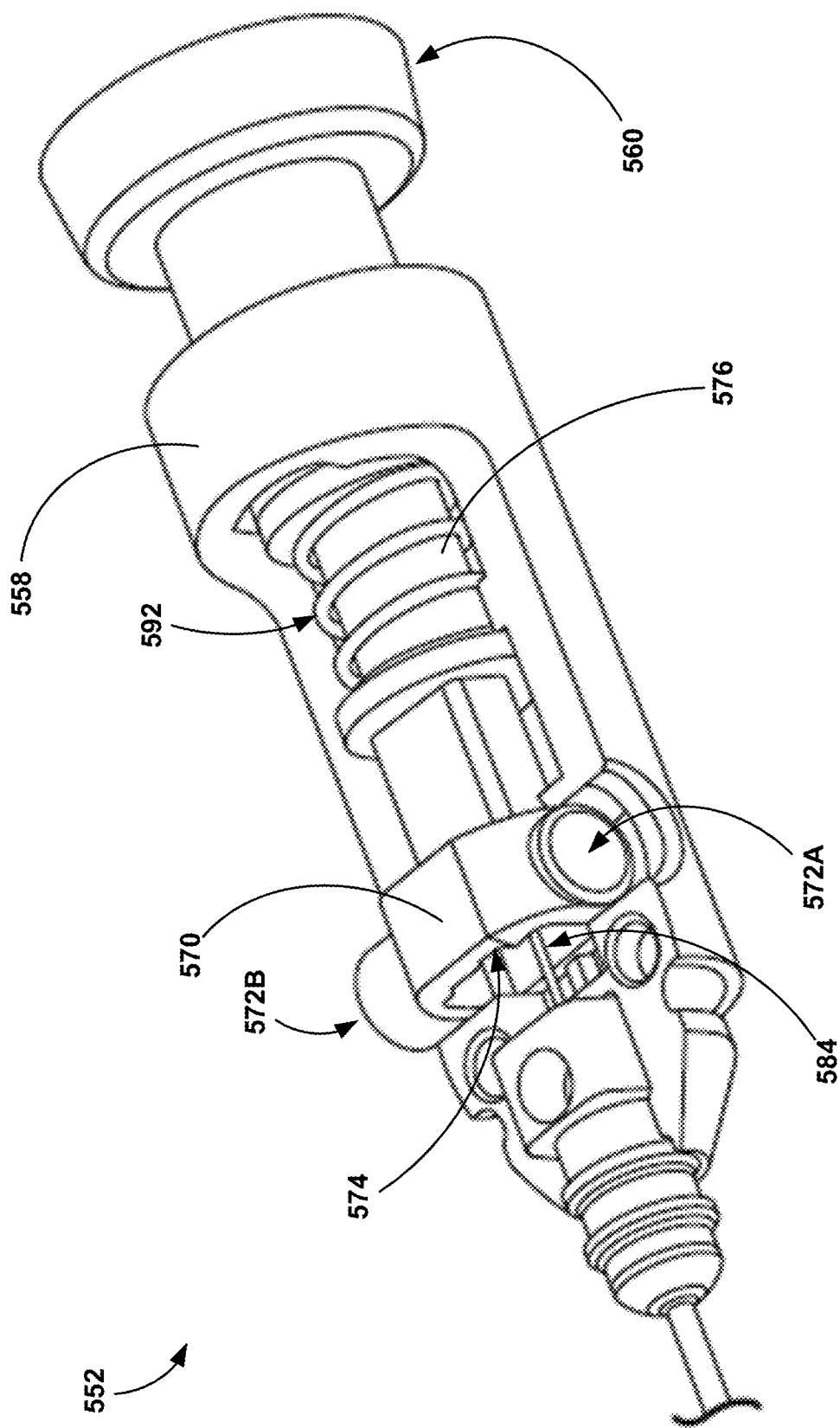

FIG. 15A is a side view of another example tether assembly 550 including another example tether handle assembly 552. FIG. 15B is an exploded plan view of tether assembly 550 and tether handle assembly 552. FIGS. 15C-15E are perspective views of tether handle assembly 552 with a portion 596 of the housing 558 removed, illustrating different positions of a lock member 570 and a plunger 560 of tether handle assembly 552 during use.

As illustrated in FIG. 15A, tether handle assembly 552 may be coupled to a proximal end of an elongate member 554 of tether assembly 550, which may correspond with and be substantially similar to elongate member 20 illustrated in FIGS. 3-6D. In some examples, tether handle assembly 552 may be a tether handle assembly of a tether assembly including either of tether head assemblies 18 or 118. In some such examples, tether head assembly 18 or 118 may be coupled to elongate body 554 in a manner similar to a manner in which tether head assembly 18 or 118 may be coupled to elongate body 20 as described above. The tether head assemblies and tether handle assemblies described herein may be used in any suitable combination with one another as part of a tether assembly. Thus, example combinations of the tether head assemblies and tether handle assemblies described are exemplary and should not be understood to be limiting.

Tether handle assembly 552 includes a housing 558. A pull wire 584 may extend through elongate member 554, and may include a proximal end received within housing 558 of tether handle assembly 552. Tether handle assembly 552 further may include a plunger 560 configured to cause a proximal movement of the pull wire when pulled by a user. Proximal movement of the pull wire may enable movement of an inner retainer 36 or 136 from a first position to a second position, e.g., for removal of attachment member 14 of IMD 10 from a tether head assembly 18 or 118, as described with respect to FIGS. 4A-6D.

Tether handle assembly 552 further may include a strain relief member 566 attached to housing 558 at a distal end of housing 558. Elongate member 554 may be attached to strain relief member 566, and pull wire 584 may be received within strain relief member 566. In addition to providing strain relief for elongate member 554 and pull wire 584 where the elongate member attaches to and the pull wire enters housing 558, strain relief member 566 be electrically conductive and may help enable sensing of an impedance signal or enable electrical testing of IMD 10 during a procedure to deliver IMD 10 at a treatment site, as described herein with respect to strain relief member 266.

In the illustrated example, housing 558 includes removable cover portion 596, which may facilitate manufacture of handle assembly 552. Handle assembly 552 further may include an elastically-stretchable band 594, which may be configured to be placed over a distal portions of housing 558 and cover 596 to help retain components of tether handle assembly 552 in the assembled configuration illustrated in FIG. 15A.

As illustrated in FIG. 15B, tether handle assembly 552 includes a lock member 570. Lock member 570 include opposing buttons 572A and 572B (collectively, "buttons 572"). Lock member 570 also defines a keyhole 574. Tether handle assembly 552 further comprises a slidable member 576 comprising a protrusion 578. Slidable member 576 is slidable through an inner channel defined by lock member 570 so long as protrusion 578 is aligned with keyhole 574 defined by lock member 570. As illustrated in FIG. 15B, a proximal end 586 of pull wire 584 may extend from elongate member 554, through strain relief member 566, and be received within housing 558. Proximal end 586 of pull wire 584 is attached to slidable member 576. In the illustrated example, proximal end 586 of pull wire 584 is received within an anchor member 588, which may enable slidable member 576 to retain proximal end 586, thereby attaching pull wire 584 to slidable member 576.

Plunger 560 may include a plug 562 received within a collar 564. Collar 564 defines an interior passageway configured to receive a proximal portion of slidable member 576, including bayonet locks 580. Plug 562 is insertable into the interior passageway of collar 564 between bayonet locks 580, to urge the bayonet locks outward and attach plunger 560 to slidable member 576.

In some examples, tether handle assembly 552 may further include an elastically-compressible member 592, e.g., spring, positioned between an interior surface of housing 558 on one end, and an enlarged diameter portion 582 of slidable member 576 on the opposite end. Proximal movement of slidable member 576 may axially compresses elastically-compressible member 592 relative to its longitudinal axis. In some examples, elastically-compressible member 592 may help control proximal movement of slidable member 576 as slidable member 576 is moved proximally in response to a user pulling plunger 560. Additionally, or alternatively, elastically-compressible member 592 may be configured to bias slidable member 576 and/or plunger 560 to respective first positions thereof, e.g., their positions when plunger 560 has not been pulled. Thus, when a physician releases plunger 560, pull wire 584 may be moved distally by elastically-compressible member 592 to aid in returning a tether head assembly 18 or 118 in a closed configuration, e.g., returning an inner retainer 36 or 136 to first position, in some examples.

FIGS. 15C-15E are perspective views of tether handle assembly 552 with a portion 596 of the housing 558 removed, illustrating different positions of a lock member 570 and a plunger 560 of tether handle assembly 552 during use. FIG. 15C illustrates both lock member 570 and plunger 560 in their first or "home" positions. In the first position, protrusion 578 of slidable member 576 is not aligned with keyhole 574 of lock member 570. Consequently, plunger 560 is prevented from being pulled distally to its second position.

FIG. 15D illustrates lock member 570 in its second position, such that protrusion 578 of slidable member 576 is not aligned with keyhole 574 of lock member 570. A user may move lock member 570 to the second position by pressing on button 572A of lock member 570 to move lock member 570 transverse to a longitudinal axis of tether handle assembly 552. A user may move lock member 570 back to the first position by pressing on button 572B, e.g., after deploying IMD 10. Notably, it is easier for a user to access button 572B than button 572A in both the first and second positions of lock member 570, e.g., to discourage accidental unlocking and IMD deployment.

FIG. 15E illustrates lock member 570 in its second position and plunger 560 having been pulled to its second position. Pulling plunger 560 to its second position moves pull wire 584 proximally and compresses elastically-compressible member 592, storing potential energy. When a physician releases plunger 560, elastically-compressible member 592 may expand longitudinally, releasing the stored energy, and moving plunger 560 and slidable member 576 distally. As slidable member 576 moves distally, pull wire 584 may also move distally to aid in returning a tether head assembly 18 or 118 in a closed configuration, e.g., returning an inner retainer 36 or 136 to first position, in some examples.

FIG. 16A is an exploded plan view of another example tether handle assembly 652. FIG. 14B is a cross-section view of tether handle assembly 652. Except as noted herein, tether handle assembly 652 may be substantially similar to tether handle assembly 552 described above with respect to FIGS. 15A-15E. For example, components of tether handle assembly 652 having the same reference numbers as components in tether handle assembly 552 may be configured and function as described with respect to FIGS. 15A-15E.

Figure 16B:
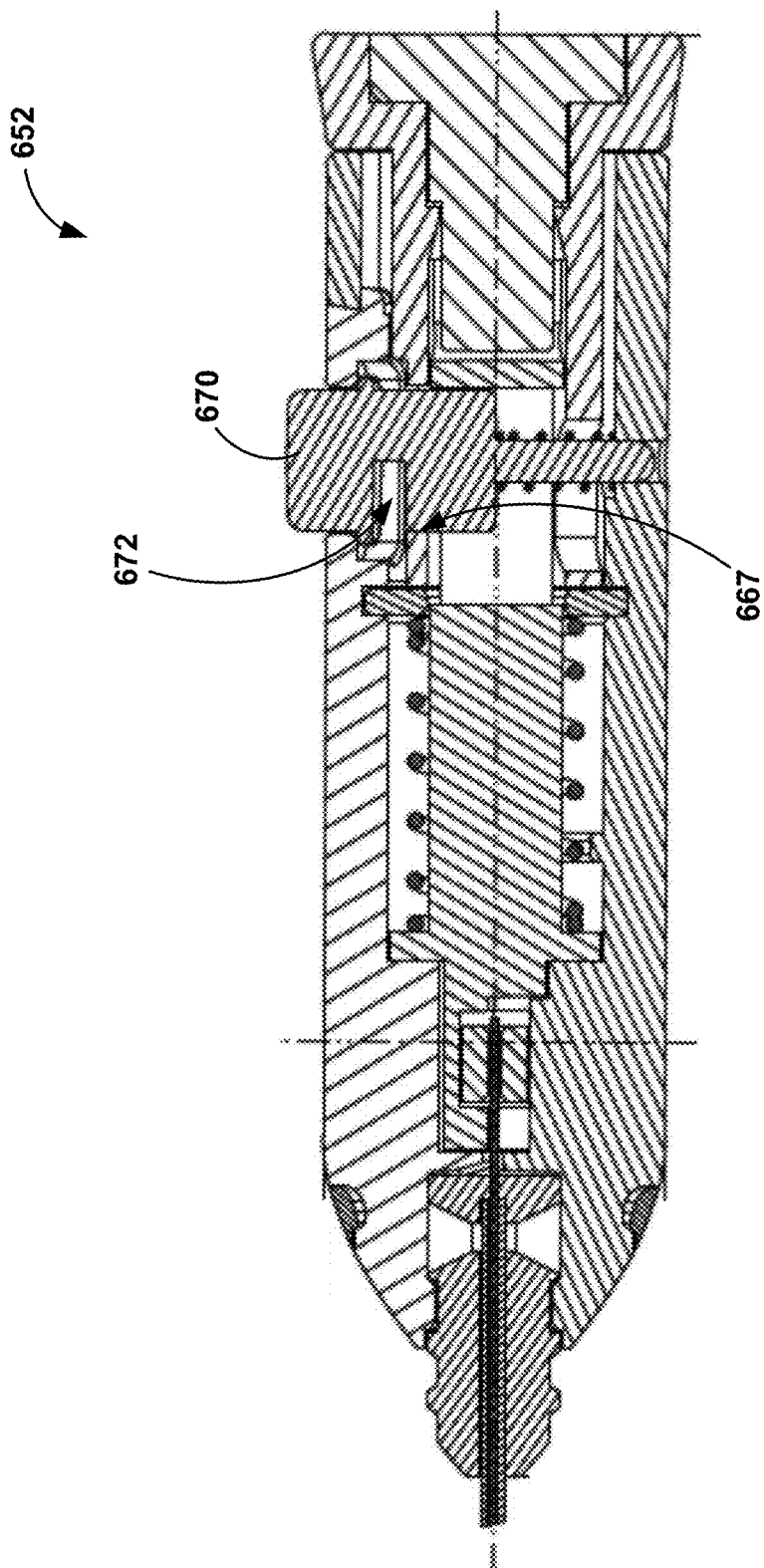
FIG. 16B is a cross-section view of the example tether handle assembly of FIG. 14A.

Plunger 660 differs from plunger 560 in that collar 664 defines an aperture 665. Removable housing portion 696 and slidable member 676 also define apertures 697 and 678, respectively. Apertures 697, 665, and 678 align to define a passageway to receive a lower portion of a lock member 670 of tether handle assembly 652 within housing 558. Lock member 670 includes a lower post 674 receivable within a longitudinal lumen defined by elastically-compressible member 675, which biases lock member 670 to a locked position. Lock member 670 further defines an inlet 672 that acts as a keyhole for lock member 670. When lock member 670 is pressed down and into the unlocked position, compressing elastically-compressible member 675, inlet 672 aligns with a distal edge 667 of aperture 665 defined by collar 664. The alignment of inlet 672 and distal edge 667 allows plunger 660 to be pulled proximally. FIG. 16B illustrates lock member 670 in the unlocked position, with inlet 672 and distal edge 667 not aligned, and plunger 670 prevented from being pulled proximally, e.g., to open a tether head member and release an IMD.

Figure 17A:
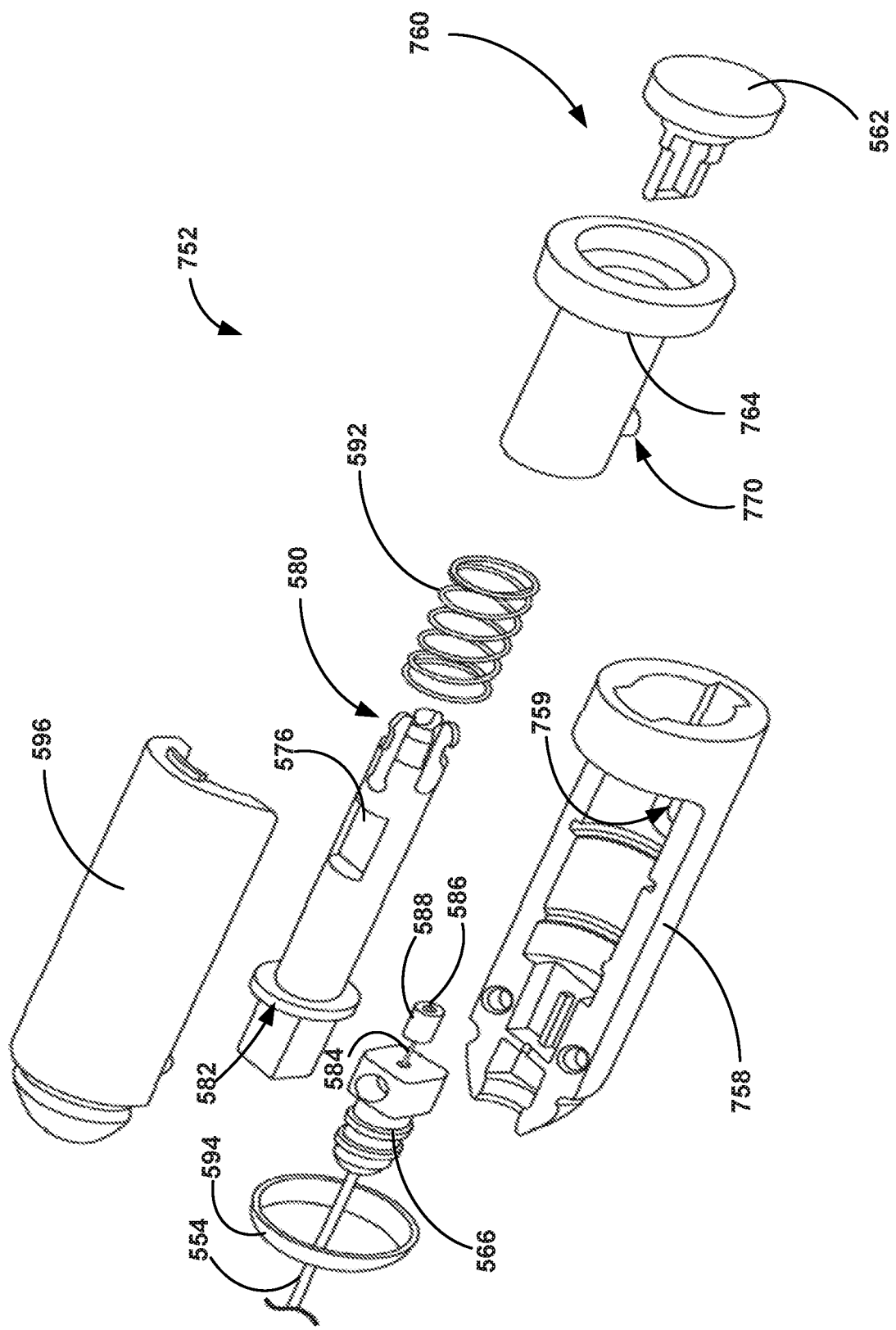
FIG. 17A is an exploded plan view of another example tether handle assembly.
Figure 17B:
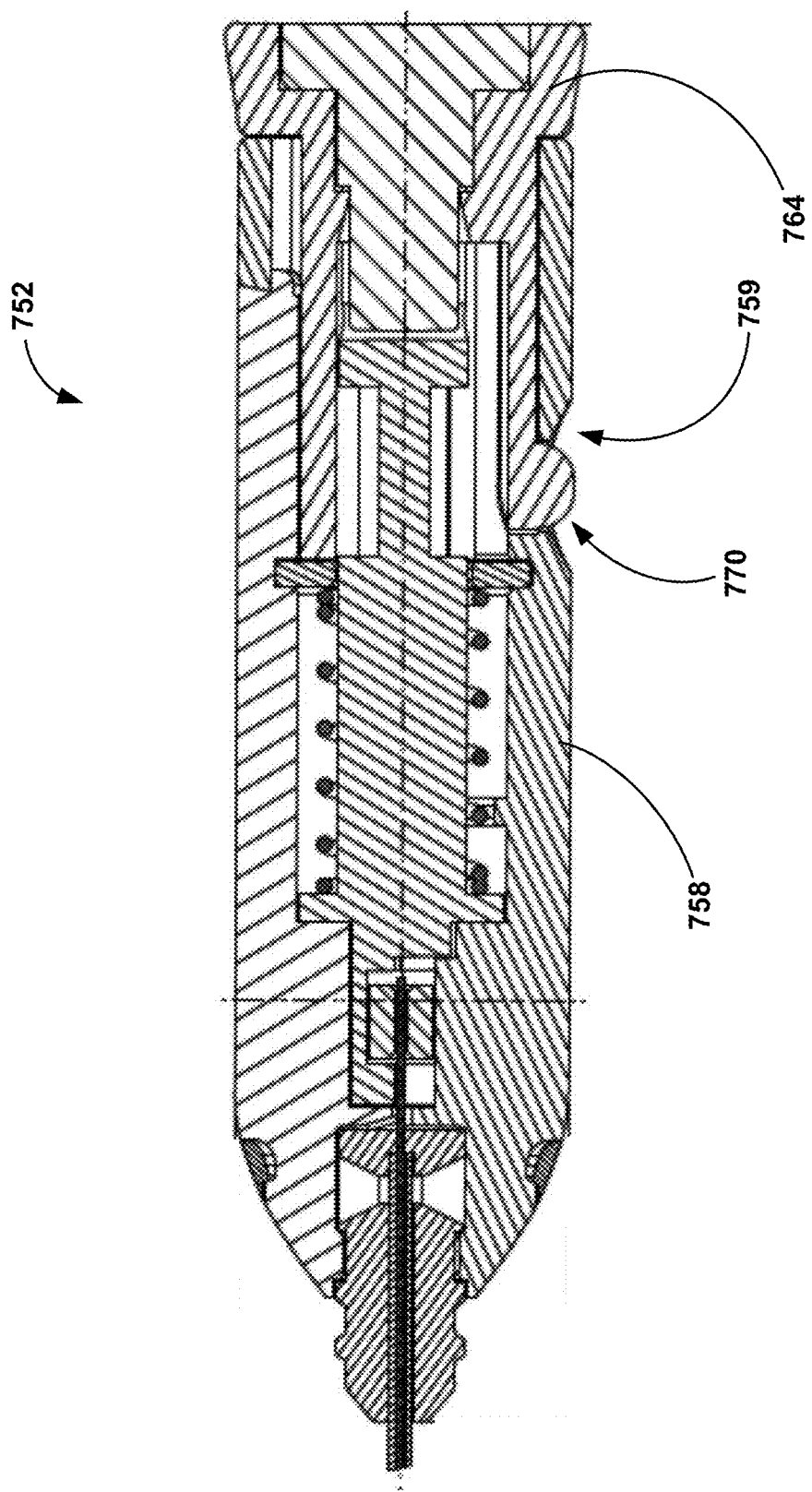
FIG. 17B is a cross-section view of the example tether handle assembly of FIG. 17A.
Figure 17C:
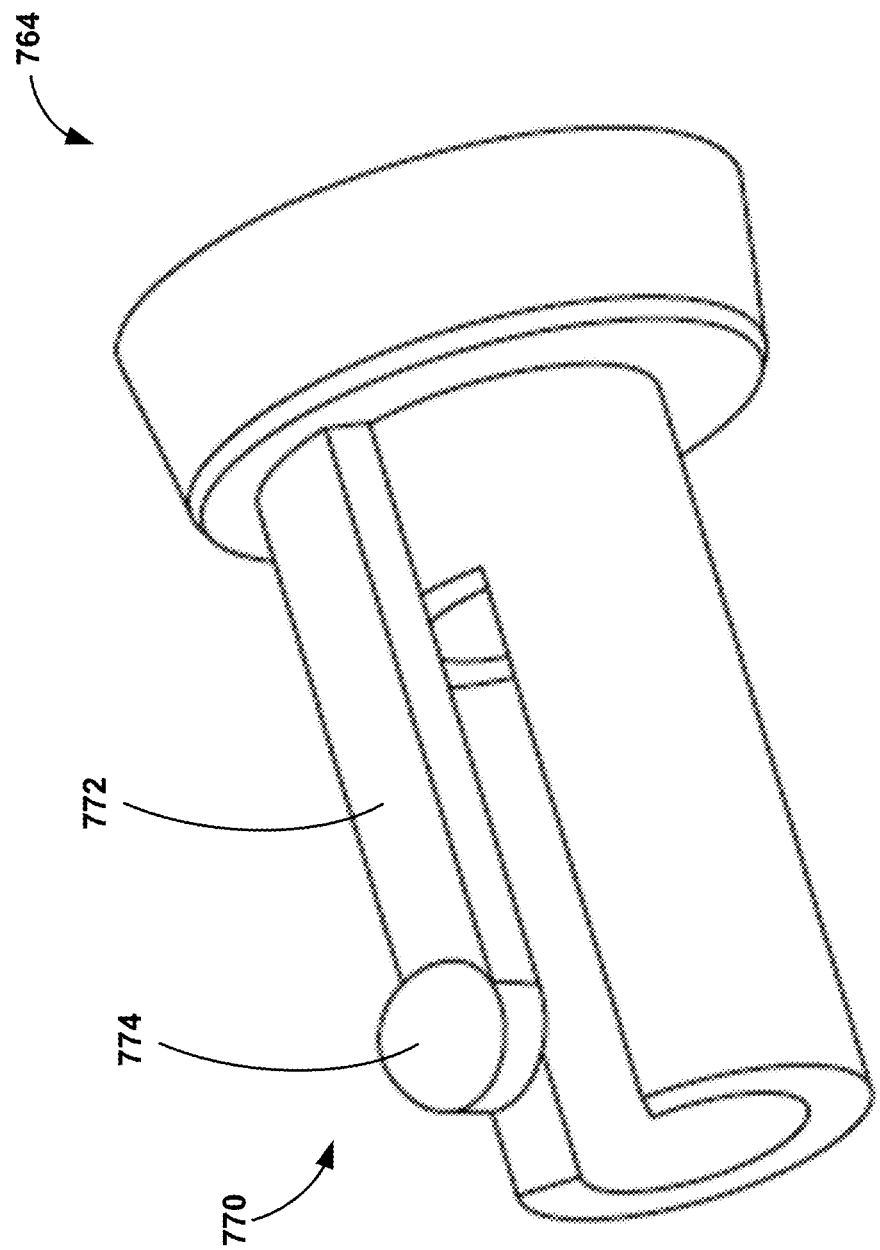
FIG. 17C is a plan view of the collar portion of the plunger of the example tether handle assembly of FIG. 17A.

FIG. 17A is an exploded plan view of another example tether handle assembly 752. FIG. 17B is a cross-section view of tether handle assembly 752. FIG. 17C is a plan view of a collar portion 764 of a plunger 760 of tether handle assembly 752. Except as noted herein, tether handle assembly 752 may be substantially similar to tether handle assembly 552 described above with respect to FIGS. 15A-15E. For example, components of tether handle assembly 752 having the same reference numbers as components in tether handle assembly 552 may be configured and function as described with respect to FIGS. 15A-15E.

Plunger 760 differs from plunger 560 in that collar 764 includes a cantilevered lock mechanism 770. Additionally, housing 758 defines an aperture 759 configured to receive a button portion 774 of lock mechanism 770 when in the locked position. Button portion 774 is coupled to collar 764 by an arm portion 772, which biases button portion 774 into the locked position, as illustrated in FIG. 17B. When button portion 774 is received in aperture 759 of housing 758, a user is prevented from proximally pulling plunger 760 and releasing IMD 10. The user may press button portion 774 into housing 758, unlocking cantilevered lock mechanism 770, and allowing the user to pull plunger 760 proximally (thus pulling pull wire 784) and release IMD 10.

The following examples are illustrative of the techniques described herein.

Example 1

A tether assembly of a medical device delivery system, the tether assembly comprising: a pull wire defining a proximal end and a distal end; and a tether head assembly. The tether head assembly comprises: an inner retainer comprising a proximal portion and a distal portion, wherein the inner retainer is coupled to and extends distally from the distal end of the pull wire; an outer retainer comprising a proximal portion defining a channel configured to receive the inner retainer and a distal portion defining an aperture. The aperture comprises: a receptacle configured to receive an attachment member of a medical device; a passageway extending from a distal end defined by the outer retainer proximally to the receptacle, wherein the passageway is narrower than the receptacle; and a groove extending from the distal end of the outer retainer proximally at least to the receptacle, wherein the groove has a depth that is less than a thickness of the distal portion of the inner retainer, wherein the inner retainer is movable between a first position wherein the distal portion of the inner retainer is partially received in the groove and extends into the passageway, thereby narrowing the passageway, and a second position wherein the distal portion of the inner retainer is positioned proximal to the passageway.

Example 2

The tether assembly of example 1, wherein the passageway is dimensioned to receive the attachment member of the medical device when the inner retainer is in the second position, and wherein the passageway is dimensioned to prevent passage of the attachment member when the inner retainer is in the first position.

Example 3

The tether assembly of example 2, wherein the passageway is dimensioned to retain the attachment member of the medical device within the receptacle when attachment member is received within the receptacle and the inner retainer is in the first position.

Example 4

The tether assembly of any of examples 1 to 3, wherein the distal portion of the inner retainer comprises: a first portion including a distal end of the inner retainer, the first portion having a first thickness; a second portion proximal to the first portion, the second portion having a second thickness that is greater than the first thickness; and a third portion extending between the first portion and the second portion, the third portion tapering in thickness from the first thickness to the second thickness.

Example 5

The tether assembly of example 4, wherein at least the third portion of the inner retainer is configured to contact the attachment member of the medical device when the inner retainer is in the first position.

Example 6

The tether assembly of any of examples 1 to 5, wherein the inner retainer and the attachment member of the medical device are electrically conductive.

Example 7

The tether assembly of any of examples 1 to 6, wherein the inner retainer is configured to move from the first position to the second position in response to proximal movement of the pull wire relative to the outer retainer.

Example 8

The tether assembly of any of examples 1 to 7, wherein the inner retainer is configured to move from the first position to the second position in response to an application of force to the inner retainer by the attachment member of the medical device.

Example 9

The tether assembly of example 8, further comprising a tether handle assembly attached to the proximal end of the pull wire, wherein the tether handle assembly comprises an actuator configured to cause the proximal movement of the pull wire.

Example 10

The tether assembly of example 9, wherein the tether handle assembly is configured such that the pull wire moves proximally in response to a distally-directed force applied to the actuator and moves distally in response to removal of the distally-directed force from the actuator.

Example 11

The tether assembly of any of examples 8 to 10, further comprising an elongate body defining a proximal end, a distal end, and a lumen, wherein a first portion of the pull wire is received within the elongate body.

Example 12

The tether assembly of example 11, wherein the tether head assembly further comprises an elastically-compressible member defining a lumen, wherein a second portion of the pull wire is received within the lumen defined by the elastically-compressible member such that the elastically-compressible member is positioned proximal to the inner retainer.

Example 13

The tether assembly of example 12, wherein the elastically-compressible member defines a longitudinal axis, and wherein the inner retainer is configured move from the second position to the first position in response to axial expansion of the elastically-compressible member relative to the longitudinal axis.

Example 14

The tether assembly of example 12 or 13, wherein the tether head assembly further comprises a sheath attached to the distal end of the elongate body, wherein the elastically-compressible member, the proximal portion of the inner retainer, and the proximal portion of the outer retainer are received within the sheath.

Example 15

The tether assembly of any of examples 12 to 14, wherein the elastically-compressible member is configured to apply a distally-directed force to the inner retainer that biases the inner retainer to the first position.

Example 16

The tether assembly of any of examples 12 to 15, wherein the elastically-compressible member comprises a polymer material.

Example 17

The tether assembly of example 16, wherein the tether handle assembly is attached to the proximal end of the pull wire at the proximal end of the elongate body, and wherein the tether handle assembly is configured to cause the proximal movement of the pull wire by translating a distally-directed force applied by a user to the actuator into the proximal movement of the pull wire.

Example 18

A method for using a tether assembly of a medical device delivery system, the method comprising: positioning a tether head assembly of the tether assembly at a treatment site of a patient with an attachment member of a medical device received within a receptacle of the tether head assembly, the tether head assembly configured to releasably retain the attachment member of the medical device. The tether head assembly comprises: an inner retainer comprising a proximal portion and a distal portion, wherein the inner retainer is coupled to and extends distally from the distal end of a pull wire of the tether assembly; an outer retainer comprising a proximal portion defining a channel configured to receive the inner retainer and a distal portion defining an aperture. The aperture comprise the receptacle configured to receive the attachment member of the medical device; a passageway extending from a distal end of the outer retainer proximally to the receptacle, wherein the passageway is narrower than the receptacle; and a groove extending from the distal end of the outer retainer proximally at least to the receptacle, wherein the groove has a depth that is less than a thickness of the distal portion of the inner retainer. Positioning the tether head assembly comprises positioning the tether head assembly with the inner retainer in a first position wherein the distal portion of the inner retainer is partially received in the groove and extends into the passageway, thereby narrowing the passageway, wherein the passageway is dimensioned to prevent passage of the attachment member when the inner retainer is in the first position. The method further comprises applying a force to an actuator of tether assembly to cause a proximal movement of the pull wire, the proximal movement of the pull wire moving the inner retainer from the first position to a second position wherein the distal portion of the inner retainer is positioned proximal to the passageway, wherein the passageway is dimensioned to receive the attachment member of the medical device when the inner retainer is in the second position, allowing the attachment member of the medical device to pass from the receptacle through the passageway; and proximally moving the tether assembly with the inner retainer in the second position to remove the attachment member of the medical device from the tether head assembly, thereby delivering the medical device to the treatment site.

Example 19

The method of example 18, further comprising, prior to positioning the tether head assembly, pressing the attachment member of the medical device against a distal end of the inner retainer to move the inner retainer from the first position to the second position, allowing passage of the attachment member of the medical device through the passageway and into the receptacle defined by the outer retainer.

Example 20

The method of example 18 or 19, wherein the inner retainer and the attachment member of the medical device are electrically conductive, the method further comprising: determining whether to apply the force to the actuator based on an impedance signal sensed via an electrical path including the medical device, the attachment member, and the inner retainer.

Example 21

The method of any of examples 18 to 20, wherein a tether handle assembly of the tether assembly comprises a housing defining a proximal end and a distal end, wherein the actuator comprises a button defining a proximal surface that is distal to the proximal end of the housing when the button is in the first position, and wherein the applying the force to the actuator comprises applying a distally-directed force to the proximal surface.

Example 22

The method of any of examples 18 to 20, wherein a tether handle assembly of the tether assembly comprises a lock member, and the method further comprises moving the lock member from a first position wherein the lock member restricts actuation of the actuator to a second position wherein the lock member does not restrict actuation of the actuator.

Various aspects of the disclosure have been described. These and other aspects are within the scope of the following claims.

What is claimed is:

1. A tether assembly of a medical device delivery system, the tether assembly comprising:
a pull wire defining a proximal end and a distal end; and
a tether head assembly comprising:
an inner retainer comprising a proximal portion and a distal portion, wherein the inner retainer is coupled to and extends distally from the distal end of the pull wire;
an outer retainer comprising a proximal portion defining a channel configured to receive the inner retainer and a distal portion defining an aperture, the aperture comprising:
a receptacle configured to receive an attachment member of a medical device;
a passageway extending from a distal end defined by the outer retainer proximally to the receptacle, wherein the passageway is narrower than the receptacle; and
a groove extending from the distal end of the outer retainer proximally at least to the receptacle, wherein the groove has a depth that is less than a thickness of the distal portion of the inner retainer,
wherein the inner retainer is movable between a first position wherein the distal portion of the inner retainer is partially received in the groove and extends into the passageway, thereby narrowing the passageway, and a second position wherein the distal portion of the inner retainer is positioned proximal to the passageway.

2. The tether assembly of claim 1, wherein the passageway is dimensioned to receive the attachment member of the medical device when the inner retainer is in the second position, and wherein the passageway is dimensioned to prevent passage of the attachment member when the inner retainer is in the first position.

3. The tether assembly of claim 2, wherein the passageway is dimensioned to retain the attachment member of the medical device within the receptacle when attachment member is received within the receptacle and the inner retainer is in the first position.

4. The tether assembly of claim 1, wherein the distal portion of the inner retainer comprises:
 a first portion including a distal end of the inner retainer, the first portion having a first thickness;
 a second portion proximal to the first portion, the second portion having a second thickness that is greater than the first thickness; and
 a third portion extending between the first portion and the second portion, the third portion tapering in thickness from the first thickness to the second thickness.

5. The tether assembly of claim 4, wherein at least the third portion of the inner retainer is configured to contact the attachment member of the medical device when the inner retainer is in the first position.

6. The tether assembly of claim 1, wherein the inner retainer and the attachment member of the medical device are electrically conductive.

7. The tether assembly of claim 1, wherein the inner retainer is configured to move from the first position to the second position in response to proximal movement of the pull wire relative to the outer retainer.

8. The tether assembly of claim 1, wherein the inner retainer is configured to move from the first position to the second position in response to an application of force to the inner retainer by the attachment member of the medical device.

9. The tether assembly of claim 8, further comprising a tether handle assembly attached to the proximal end of the pull wire, wherein the tether handle assembly comprises an actuator configured to cause the proximal movement of the pull wire.

10. The tether assembly of claim 9, wherein the tether handle assembly is configured such that the pull wire moves proximally in response to a distally-directed force applied to the actuator and moves distally in response to removal of the distally-directed force from the actuator.

11. The tether assembly of claim 8, further comprising an elongate body defining a proximal end, a distal end, and a lumen, wherein a first portion of the pull wire is received within the elongate body.

12. The tether assembly of claim 11, wherein the tether head assembly further comprises an elastically-compressible member defining a lumen, wherein a second portion of the pull wire is received within the lumen defined by the elastically-compressible member such that the elastically-compressible member is positioned proximal to the inner retainer.

13. The tether assembly of claim 12, wherein the elastically-compressible member defines a longitudinal axis, and wherein the inner retainer is configured move from the second position to the first position in response to axial expansion of the elastically-compressible member relative to the longitudinal axis.

14. The tether assembly of claim 12, wherein the tether head assembly further comprises a sheath attached to the distal end of the elongate body, wherein the elastically-compressible member, the proximal portion of the inner retainer, and the proximal portion of the outer retainer are received within the sheath.

15. The tether assembly of claim 12, wherein the elastically-compressible member is configured to apply a distally-directed force to the inner retainer that biases the inner retainer to the first position.

16. The tether assembly of claim 12, wherein the elastically-compressible member comprises a polymer material.

17. The tether assembly of claim 16, wherein the tether handle assembly is attached to the proximal end of the pull wire at the proximal end of the elongate body, and wherein the tether handle assembly is configured to cause the proximal movement of the pull wire by translating a distally-directed force applied by a user to the actuator into the proximal movement of the pull wire.

18. A method for using a tether assembly of a medical device delivery system, the method comprising:
 positioning a tether head assembly of the tether assembly at a treatment site of a patient with an attachment member of a medical device received within a receptacle of the tether head assembly, the tether head assembly configured to releasably retain the attachment member of the medical device, wherein the tether head assembly comprises:
  an inner retainer comprising a proximal portion and a distal portion, wherein the inner retainer is coupled to and extends distally from the distal end of a pull wire of the tether assembly;
  an outer retainer comprising a proximal portion defining a channel configured to receive the inner retainer and a distal portion defining an aperture, the aperture comprising:
   the receptacle configured to receive the attachment member of the medical device;
   a passageway extending from a distal end of the outer retainer proximally to the receptacle, wherein the passageway is narrower than the receptacle; and
   a groove extending from the distal end of the outer retainer proximally at least to the receptacle, wherein the groove has a depth that is less than a thickness of the distal portion of the inner retainer,
  wherein positioning the tether head assembly comprises positioning the tether head assembly with the inner retainer in a first position wherein the distal portion of the inner retainer is partially received in the groove and extends into the passageway, thereby narrowing the passageway, wherein the passageway is dimensioned to prevent passage of the attachment member when the inner retainer is in the first position;
 applying a force to an actuator of tether assembly to cause a proximal movement of the pull wire, the proximal movement of the pull wire moving the inner retainer from the first position to a second position wherein the distal portion of the inner retainer is positioned proximal to the passageway, wherein the passageway is dimensioned to receive the attachment member of the medical device when the inner retainer is in the second position, allowing the attachment member of the medical device to pass from the receptacle through the passageway; and proximally moving the tether assembly with the inner retainer in the second position to remove the attachment member of the medical device from the tether head assembly, thereby delivering the medical device to the treatment site.

19. The method of claim 18, further comprising, prior to positioning the tether head assembly, pressing the attachment member of the medical device against a distal end of the inner retainer to move the inner retainer from the first position to the second position, allowing passage of the attachment member of the medical device through the passageway and into the receptacle defined by the outer retainer.

20. The method of claim 18, wherein the inner retainer and the attachment member of the medical device are electrically conductive, the method further comprising:
 determining whether to apply the force to the actuator based on an impedance signal sensed via an electrical path including the medical device, the attachment member, and the inner retainer.

21. The method of claim 18, wherein a tether handle assembly of the tether assembly comprises a housing defining a proximal end and a distal end, wherein the actuator comprises a button defining a proximal surface that is distal to the proximal end of the housing when the button is in the first position, and wherein the applying the force to the actuator comprises applying a distally-directed force to the proximal surface.

22. The method of claim 18, wherein a tether handle assembly of the tether assembly comprises a lock member, and the method further comprises moving the lock member from a first position wherein the lock member restricts actuation of the actuator to a second position wherein the lock member does not restrict actuation of the actuator.

\* \* \* \* \*